United States Patent [19]

Ohno et al.

[11] Patent Number: 5,770,375
[45] Date of Patent: Jun. 23, 1998

[54] PROBE FOR DIAGNOSING STAPHYLOCOCCUS EPIDERMIDIS

[75] Inventors: Tsuneya Ohno, 15-16, Kita-Aoyama 3 chome, Minato-ku, Tokyo 107; Akio Matsuhisa, Nara; Hirotsugu Uehara, Kobe; Soji Eda, Higashi, all of Japan

[73] Assignees: Tsuneya Ohno, Tokyo; Fuso Pharmaceutical Industries, Ltd., Osaka, both of Japan

[21] Appl. No.: 920,827

[22] Filed: Aug. 29, 1997

Related U.S. Application Data

[62] Division of Ser. No. 362,577, Mar. 27, 1995.

[30] Foreign Application Priority Data

Jul. 7, 1992 [JP] Japan .................................... 4-179719

[51] Int. Cl.$^6$ .............................. C12Q 1/68; C07H 21/04
[52] U.S. Cl. ........................ 435/6; 536/24.32; 536/24.33; 935/8; 935/9; 935/78
[58] Field of Search .............................. 435/6; 536/24.32, 536/24.33; 935/8, 9, 78

[56] References Cited

PUBLICATIONS

Goering et al. Journal of Clinical Microbiology, 28(3): 426–429 Mar. 1990.

Alberts et al., *Molecular Biology of the Cell*, Second Edition, Garland Publishing Inc., New York, NY, pp. 182 and 188–193 (1989).

Bell, et al., "The Nucleotide Sequences of the rbsD, rbsA, and rbsC Genes of Escherichia coli K12", *The Journal of Biological Chemistry* 261(17):7652–7658 (Jun. 1986).

Betzl, et al., "Identification of Lactococci and Enterococci by Colony Hybridization with 23S rRNA–Targeted Oligonucleotide Probes", *Applied and Environmental Microbiology*: 56(9):2927–2929 (Sep. 1990).

Buckel, et al., "An Analysis of the Structure of the Product of the rbsA Gene of Escherichia coli D12", *The Journal of Biological Chemistry* 261(17):7659–7662 (Jun. 1986).

Cano et al., *Microbiology*, West Publishing Company, Minneapolis, MN, pp. 264–268, 279, 293, 296, 297, and 801 (1986).

Davis, et al., "Direct Identification of Bacterial isolates in Blood Cultures by Using a DNA Probe", *Journal of Clinical Microbiology* 29(10):2193–2196 (Oct. 1991).

De Buyser, et al., "Evaluation of a ribosomal RNA gene probe for the identification of species and subspecies within the genus *Staphylococcus*", *Journal of General Microbiology* 138:889–899 (1992).

Gerberding et al. Antimicrobial Agents and Chemotherapy 35(12):2574–2579 (1991).

Groarke, et al., "The Amino Acid Sequence of D–Ribose–binding Protein from Escherichia coli K12", *The Journal of Biological Chemistry* 258(21):12952–12956 (Jun. 1983).

Hall, et al., "Typing of Enterococcus Species by DNA Restriction Fragment Analysis", *Journal of Clinical Microbiology* 30(4):915–919, (Apr. 1992).

Hope, et al., "Ribokinase from Escherichia coli K12", *The Journal of Biological Chemistry* 261(17):7663–7668 (Jun. 1986).

Joffee, et al., "Epidemiologic Studies of Nosocomial Infections with Pseudomonas aeruginosa Using a DNA Probe", *Abstracts of the Annual Meeeting*:485 (1989).

Lehninger, A. L., *Principles of Biochemistry*, Worth Publishers, Inc., New York, pp. 809–811 (1982).

(List continued on next page.)

Watson et al., *Recombinant DNA: A Short Course*, Scientific American Books, USA, pp. 58–60 (1983).

*Primary Examiner*—Carla J. Myers
*Attorney, Agent, or Firm*—Marshall, O'Toole, Gerstein, Murray & Borun

[57] ABSTRACT

DNA probes for diagnosing infectious diseases involving *Staphylococcus epidermidis* and methods of using such probes are provided.

2 Claims, 6 Drawing Sheets

OTHER PUBLICATIONS

Maniatis et al., *Molecular Cloning: A Laboratory Manual*, Cold Spring Harbor Laboratory, Cold Spring Harbor, NY, pp. 309–330, 374 and 375 (1982).

Sambrook et al., *Molecular Cloning: A Laboratory Manual*, Second Edition, Cold Spring Harbor Laboratory Press, Cold Spring Harbor, NY, pp. 5.10, 5.11, and 12.21–12.23 (1989).

Smith et al., *Principles of Biochemistry: General Aspects*, Seventh Edition, McGraw–Hill Book Company, New York, NY, p. 723 (1983).

Tredget, et al., "Epidemiology of Infections with *Pseudomonas aeruginose* in Burn Patients: The Role of Hydrotherapy", *Clinical Infectious Diseases* 15:941–949, (1992).

Watson et al., *Molecular Biology of the Gene*, Fourth Edition, The Benjamin/Cummings Publishing Company, Inc., Menlo Park, CA, pp. 89, 208–210, and 608 (1987).

PROBE FOR DIAGNOSING STAPHYLOCOCCUS EPIDERMIDIS

This is a Divisional of U.S. application Ser. No. 08/362,577, filed Mar. 27, 1995.

TECHNICAL FIELD

The present invention relates to probes, prepared by making use of causative bacteria of infectious diseases, which are useful for detecting and identifying the causative bacteria.

BACKGROUND ART

In pathology, infection is defined as invasion and establishment of a foothold for growth in an organism by a pathogenic organism (hereinafter referred to as "bacteria"), then the outbreak of disease depends upon the interrelationship between the resistance of host and the virulence of bacteria.

In the infectious diseases, improvement in treatment methods of bateremia have been raised as an important issue. That is to say, bacteremia is not a disease caused by a particular bacterium, but is caused by emergence and habitancy of the various bacteria in blood, then onset thereof is clinically suspected when fever of about 40° C. persists for two or more days. If a patient is an infant or is suffering from terminal cancer with weakened resistance, the patient may die in one or two days, therefore, the bacteremia is a serious and urgent disease, and the improvement in treatment methods thereof have been awaited.

In the infectious disease, phagocytes including neutrophils, monocytes and macrophages primarily work in defense of the body. Emergence of bacteria in the blood is thought as invasion of predominant bacteria which have emerged from the tissue of the phagocyte.

Bacteremia is a state wherein the bacteria is emerged into the blood, and a large amount of antibiotic is administrated to treat it wherein the causative bacteria is sensitive to the antibiotic. Generally, since antibiotics lower the functions of the internal organs such as liver, it is necessary to pay an attention to reduce an administration of an ineffective antibiotic to a patient in a serious state.

When bacteremia is defined as a case wherein phagocytesis of cells can not overcome the virulence of bacteria, then the bacteria spread in the body through the blood, bacteremia with serious symptoms due to toxins produced by the bacteria is called as sepsis. Proof of sepsis, in the other word, establishment of the diagnosis requires a check on the items of 1) clinical symptoms, 2) culturing of specimen, 3) gram-staining of the bacteria contained in the specimen, and 4) shock state, then, upon completing the check of these items, the treatment method is determined. Accordingly, to quickly and reliably identify the bacteria have been awaited in the art.

In the present method for detecting and identifying bacteria in a bacteremia-specimen, it is a common procedure to identify in selective medium a specimen which have positive signal in a routine process of culture bottle. However, to successfuly culture the bacteria from these blood specimen is quite difficult, then, if a large dose of antibiotics is administrated when bacteremia was suspected, bacteria in the blood will not be cultured and grown in many cases, therefore, the rate of culture bottle positive case become extremely low.

Although available sub-routine methods include instrumental analysis of constituents and metabolic products of bacteria (Yoshimi Benno, "Quick identification of bacteria with gas chromatography", Rinsho Kensa, Vol. 29, No.12, November 1985, Igaku Shoin ed.), a method utilizing specific antibody (Japanese Patent Provisional Publication No. 60-224068), and a hybridization method utilizing specificity of DNA (Japanese Phase Patent Provisional Publication No. 61-502376) have been developed, any of which are required to separate the bacteria and culture it. On the other hand, as a method established based on the function of phagocytes in infectious diseases, there is a method to examine, under an optical microscope, a stained smear of buffy coat wherein leukocyte of the blood sample is concentrated. Generally speaking, although the rate of detection of bacteria in buffy coat specimens from adult bacteremia patients is 30% at most, which is similar to that in earlobe blood specimens, it was reported that bacteria had been detected in seven cases of ten cases (T70%) in newborn patients, therefore, an information concerning the presence of a bacteria in peripheral blood to be obtained by microscope examination on smear is an important for treatment. Since the conventional methods necessiate the pretreatment which requires at least three to four days in total containing one to two day(s) for selective isolation of bacteria from a specimen, one day for cultivation, and one or more day(s) for fixation, and the culture thereof is continued in practice until the bacteria grow, the culture will needs one week or more even for C.B.-positive cases, therefore, this was a factor in high mortality of C.B.-positive patients being treated by the conventional methods. For example, according to the a report published in "The Journal of the Japanese Association for Infectious Diseases", Vol.58, No.2, p.122, 1984, even though the blood culture positive rate was 28.6% (163 cases/569 cases), the mortality was as high as 84.6% (138 cases/163 cases).

Further, it may be impossible to distinguish contamination at the cultivation by indigenous bacteria. For example, *Staphylococcus epidermides*, which is one of Staphylococci and is the causative bacterium of bacteremia, stayed in the skin of the normal person, then, there is a risk on contamination of a specimen with this bacterium when a needle is inserted into the skin.

As an important matter, under such circumstances above, since many bacteria in a specimen to be cultured have been incorporated into said phagocyte and are dead or stationary immobilized, the number of growable bacteria is small even under appropriate conditions for cultivation, thereby, the actual detection rate of bacteria through culture specimen is as low as about 10%. In the other word, at this moment, 90% of the examined blood, which have been cultured for further one or more day(s), of the patient suspected clinically as suffering with bacteremia can not clarify the presence of bacteria.

In light of the situation above, the present practice depends on a treatment to be started when bacteremia is clinically suspected without awaiting the detection results, that is to say, a trial and error method wherein an antibiotic having broad spectrum is administrated first, and if the antibiotic is not effective after one or two day(s), another antibiotic will be tried.

According to the method to stain the bacteria in the specimen, the constituents of the living body are also stained together with bacteria, therefore, experience to quickly identify bacteria according to thier image through microscope is required, then there may be cases that can be hardly diagnosed as bacteremia.

Although bacteremia is a disease wherein a rapid and exact diagnosis have been required, the conventional diagnosis method can not respond to such requirements.

DISCLOSURE OF INVENTION

The present invention was established in view of the problems in the art, and is directed to a probe having a specific reactivity with DNA or RNA obtained from primary causative bacteria of the infectious diseases, then provide a genetic information by analyzing the base sequence of DNA in the probe.

By the probe of the present invention, for example, a causative bacteria of the infectious diseases is detected rapidly and exactly, without cultivating/proliferating the bacteria, through a detection of DNA held in the causative bacteria digested and incorporated gradually with the phagocyte. Then, if primers are designed by referring to an information on base sequence of these probes, causative bacteria can identify, without the hybridization, by amplifying the DNA with PCR technique.

When non-radioactive probe, for example, biotinylated probe is used for hybridization, since such probe can be detected with an optical microscope in a conventional laboratory without radio isotope handling facilities, the detection process would be rapid and simple.

Figure 1:
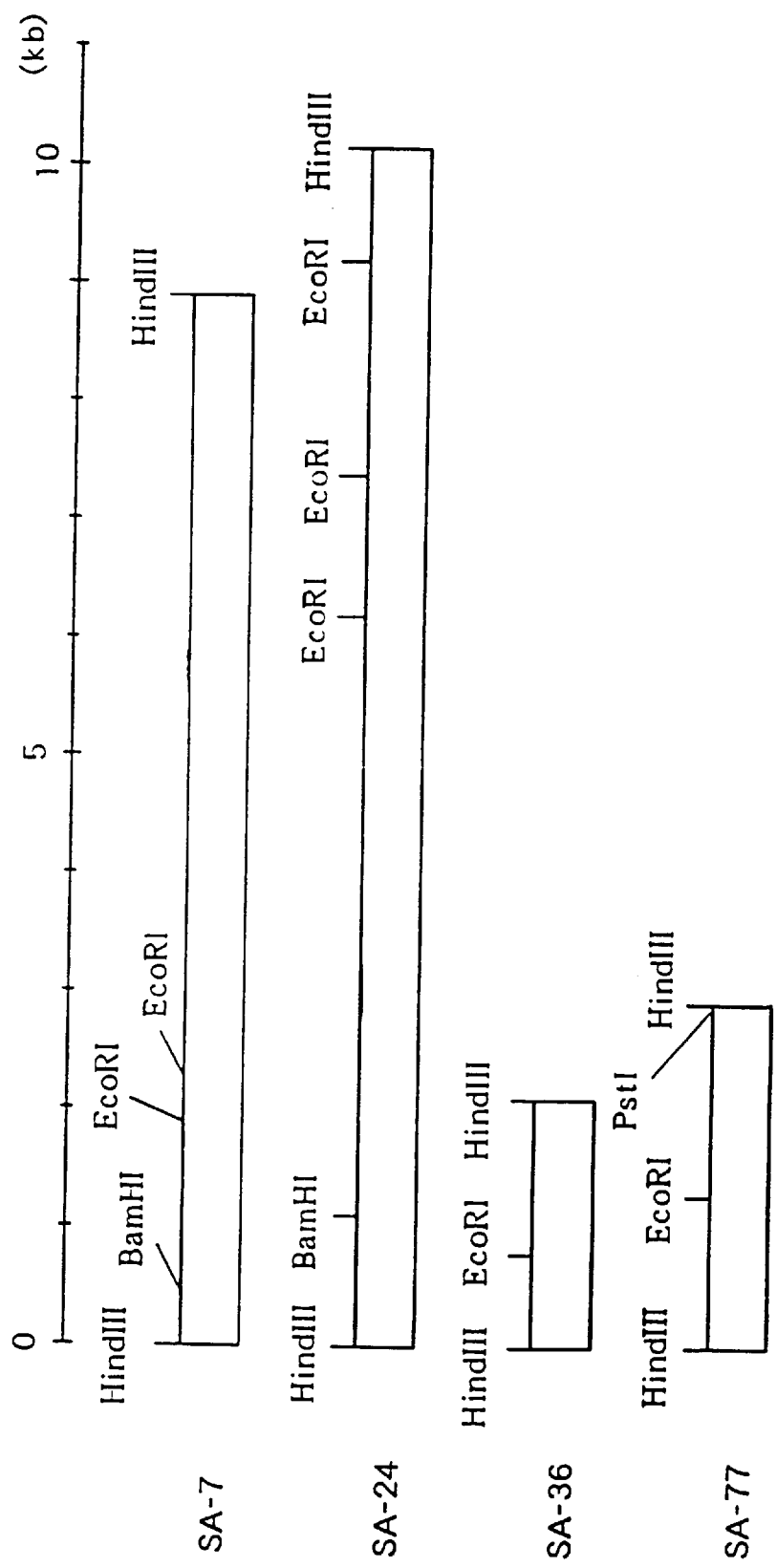
FIG. 1 is a restriction enzyme map of HindIII fragment on probe for detecting *Staphylococcus aureus*.

Best Mode for Carrying Out the Invention

Examples on probes prepared from *Staphylococcus aureus, Staphylococcus epidermidis, Enterococcus faecalis, Pseudomonas aeruginosa, Escherichia coli, Klebsiella pneumoniae* and *Enterobacter cloacae* (J. Infection, vol. 26, pp.159–170 (1993), J. Clin. Microbiol., vol.31., pp.552–557 (1993)), respectively listed as relatively popular causative bacteria of the infectious diseases, especially bacteremia were described as follows.

EXAMPLE 1

Preparation of DNA Probe from Causative Bacteria of Infectious Diseases (1) Isolation of Causative Bacteria of Infectious Diseases Blood collected from the patient who have been suffered with targeted diseases were applied to Blood Culture Method (BBC System: Blood Culture System; Roche) and to a conventional identification kit (Api 20, Apistaf, Apistlep 20: Bio-Nleryu), and the each causative bacterium was isolated and identified according to the manual of said kit.

(2) Extraction and Purification of Genomic DNA from Isolated Strain

Strains isolated in the above (1) was cultivated overnight in BHI (Brain Heart Infusion) medium, collected the cultivated bacteria, added thereto achromopeptidase in stead of lysozyme, then, Genomic DNA was extracted according to Saito-Miura Method ("Preparation of Transforming Deoxyribonucleic Acid by Phenol Treatment", Biochem. Biophys. Acta. vol. 79, pp.619–629), and extracted DNA was digested with restriction enzyme HindIII and was random cloned into vector pBR322.

(3) Selection of Probe having Specificity to Species of Origin Bacteria

*Escherichia coli* containing each clone prepared according to Manual of Maniatis (T. Maniatis, et al., "Molecular Cloning (A Laboratory Manual)", Cold Spring Harbour Laboratory (1982)) was cultivated with small scale culture, and obtained plasmids containing each clone.

These plasmids were digested with restriction enzyme HindIII, thereby inserts were separated completely from plasmids with 1% agarose-gel electrophoresis (Myupid: Cosmo-Bio), then, were transcribed to nylon membrane with Southern-Transfer Technique (Paul Biodine A: Paul), and were cross-hybridized with a probe prepared by labelling $^3_2$P-dCTP (Amersham) through nick-translation to chromosome DNA from each bacteria species aforelisted.

In this hybridization, a probe which did not cross-react with any insert except for a probe prepared from the origin species thereof was selected as a probe containing DNA fragment which is specific to causative bacteria of the infectious diseases.

With regard to probes prepared from *Escherichia coli, Klebsiella pneumoniae, Enterobacter cloacae*, since these bacteria are belonged to the same group (enteric bacteria; Gram negative aerobic bacillus) as a causative bacteria of bacteremia (See, J. Infection, vol. 26, pp.159–170 (1993), J. Clin. Microbiol., vol.31., pp. 552–557 (1993), supra), and the cross-reaction had been confirmed among said three bacteria in the foregoing series experiments on the specificity, each probe prepared from one of said three bacteria was designated as a probe for detecting all these bacteria as a relevant bacteria.

Probes (denotation) selected from each species through the foregoing methods are listed in the following Table 1.

TABLE 1

| SPECIES | DENOTATION |
|---|---|
| *Staphylococcus aureus* | SA-7, SA-24, SA-36, SA-77 |
| *Staphylococcus epidermidis* | SE-3, SE-22, SE-32, SE-37 |
| *Enterococcus faecalis* | S2-1, S2-3, S2-7, S2-27 |
| *Pseudomonas aeruginosa* | P2-2, P2-7, P2-17, P4-5 |
| *Escherichia coli* | EC-24, EC-34, EC-39, EC-625 |
| *Klebsiella pneumoniae* | KI-50 |
| *Enterobacter cloacae* | ET-12, ET-49 |

Figure 2:
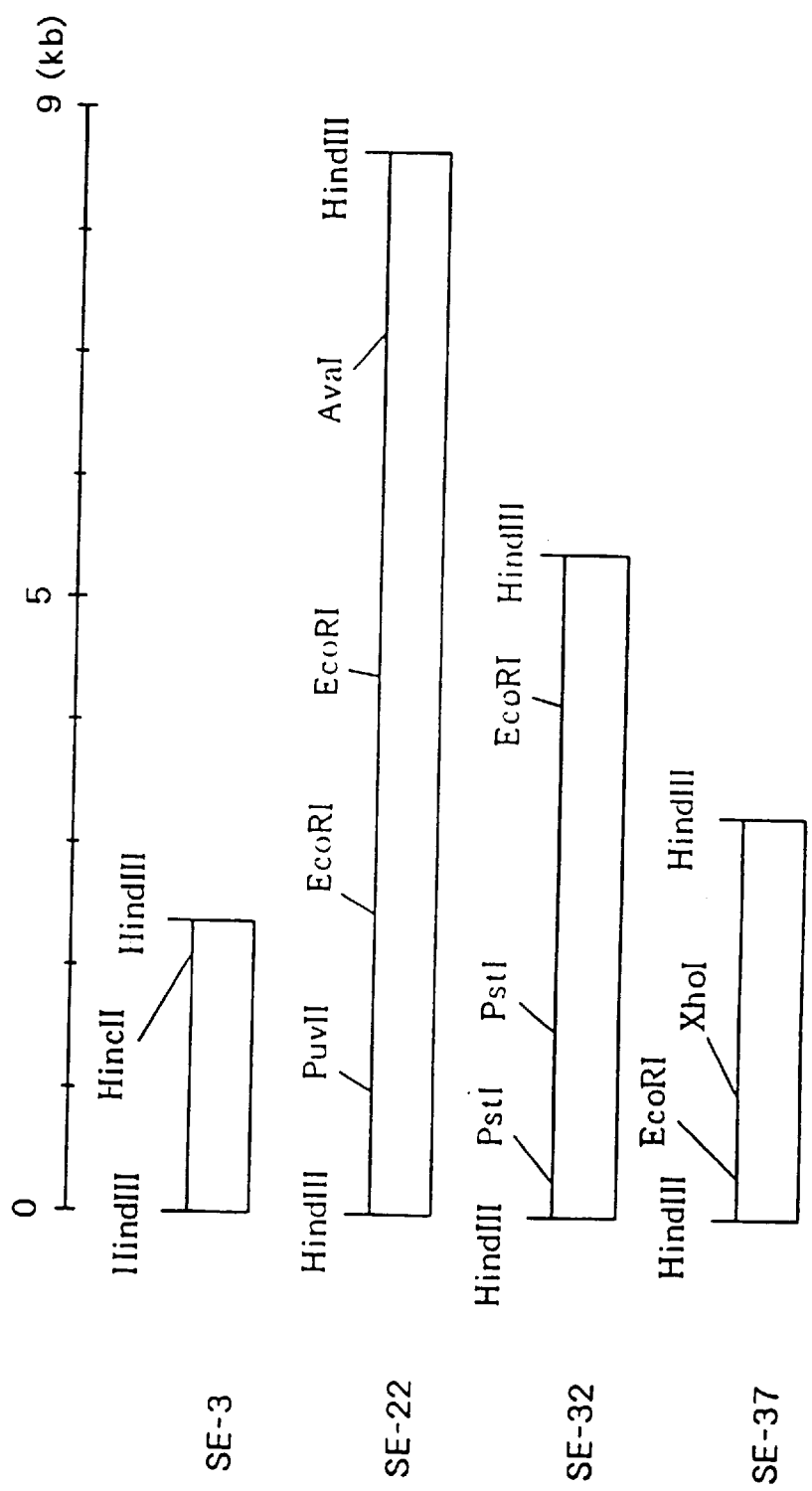
FIG. 2 is a restriction enzyme map of HindIII fragment on probe for detecting *Staphylococcus epidermidis*.
Figure 3:
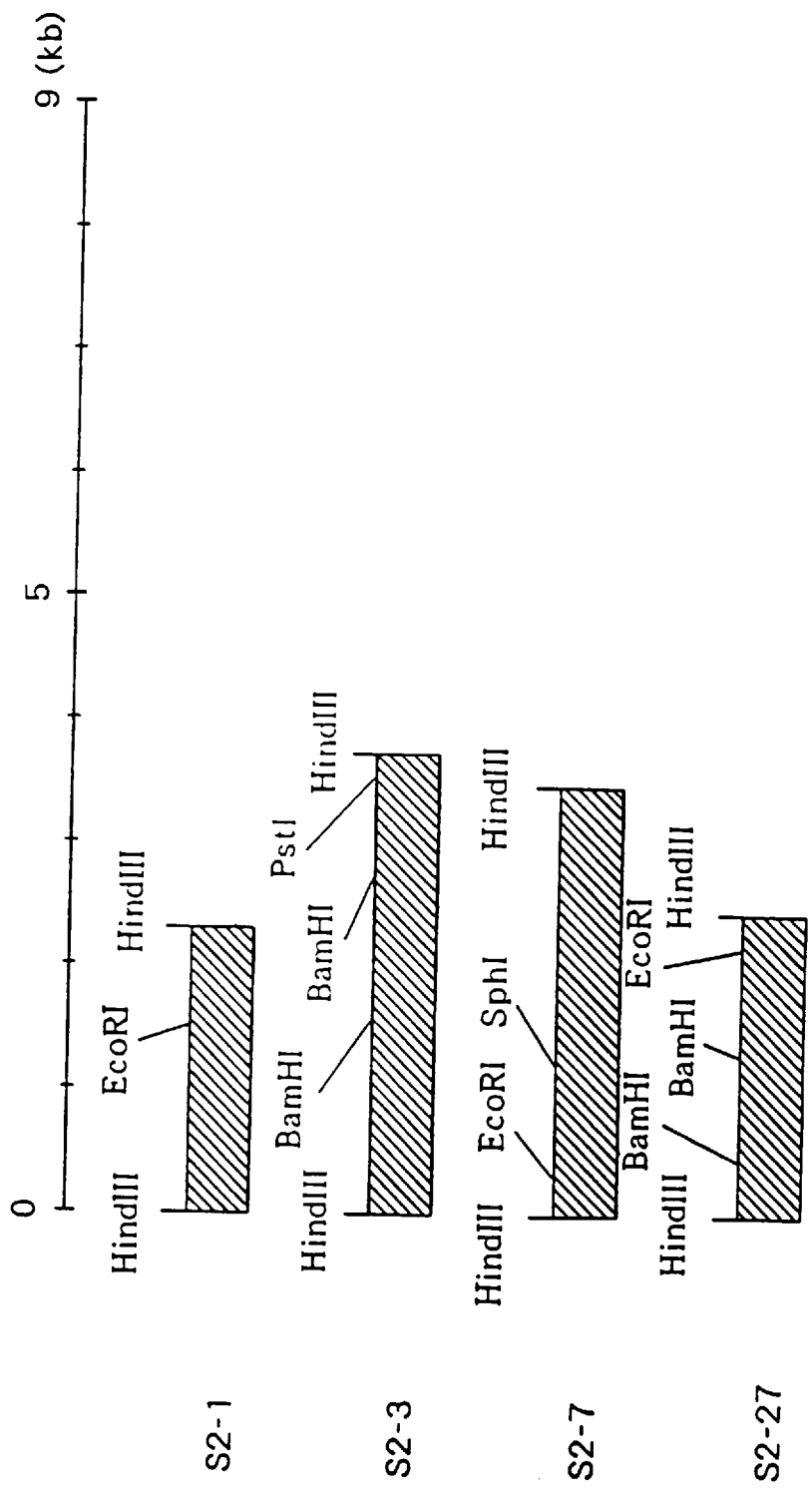
FIG. 3 is a restriction enzyme map of HindIII fragment on probe for detecting *Enterococcus faecalis*.
Figure 4:
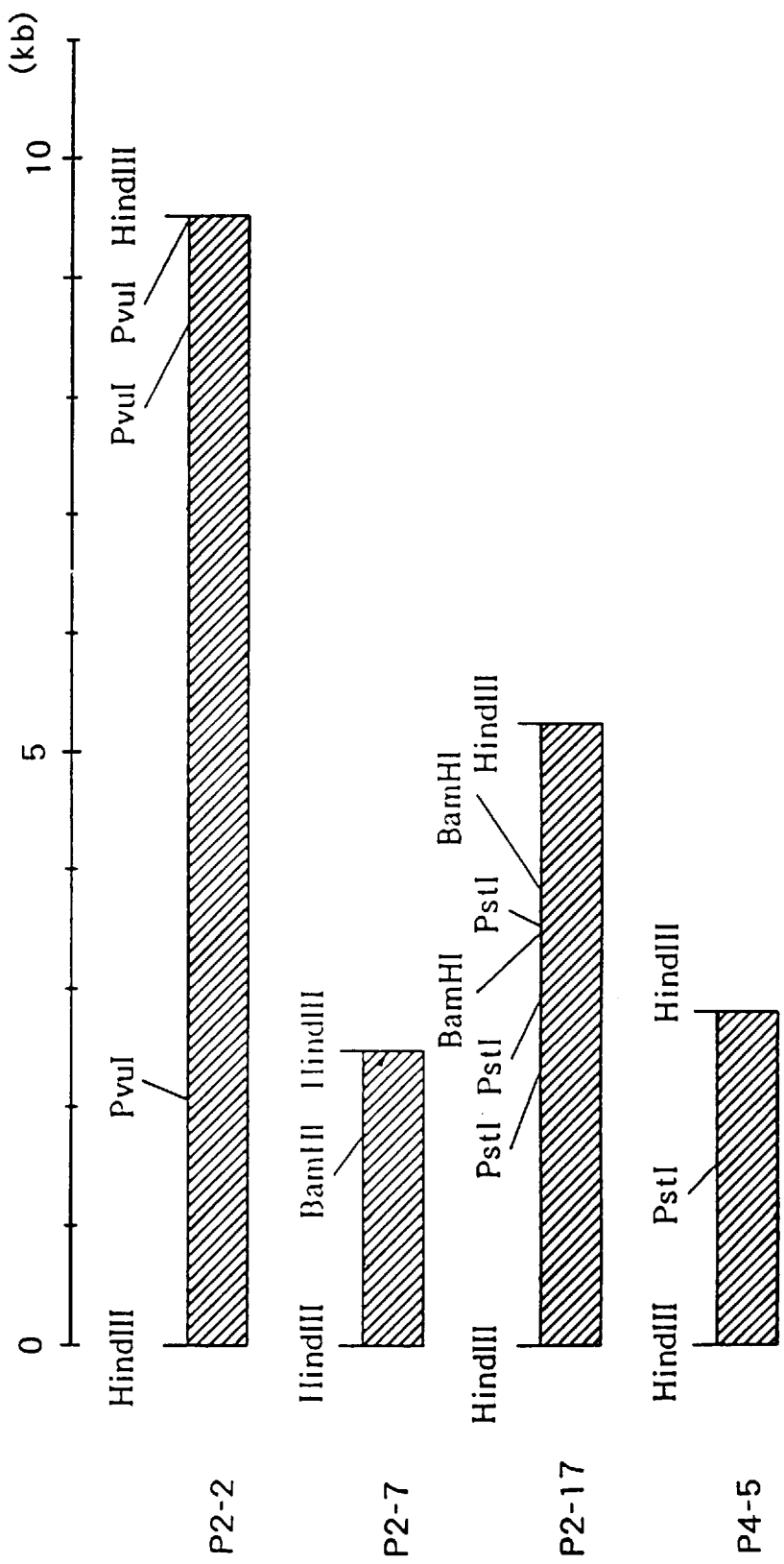
FIG. 4 is a restriction enzyme map of HindIII fragment on probe for detecting *Pseudomonas aeruginosa*.
Figure 5:
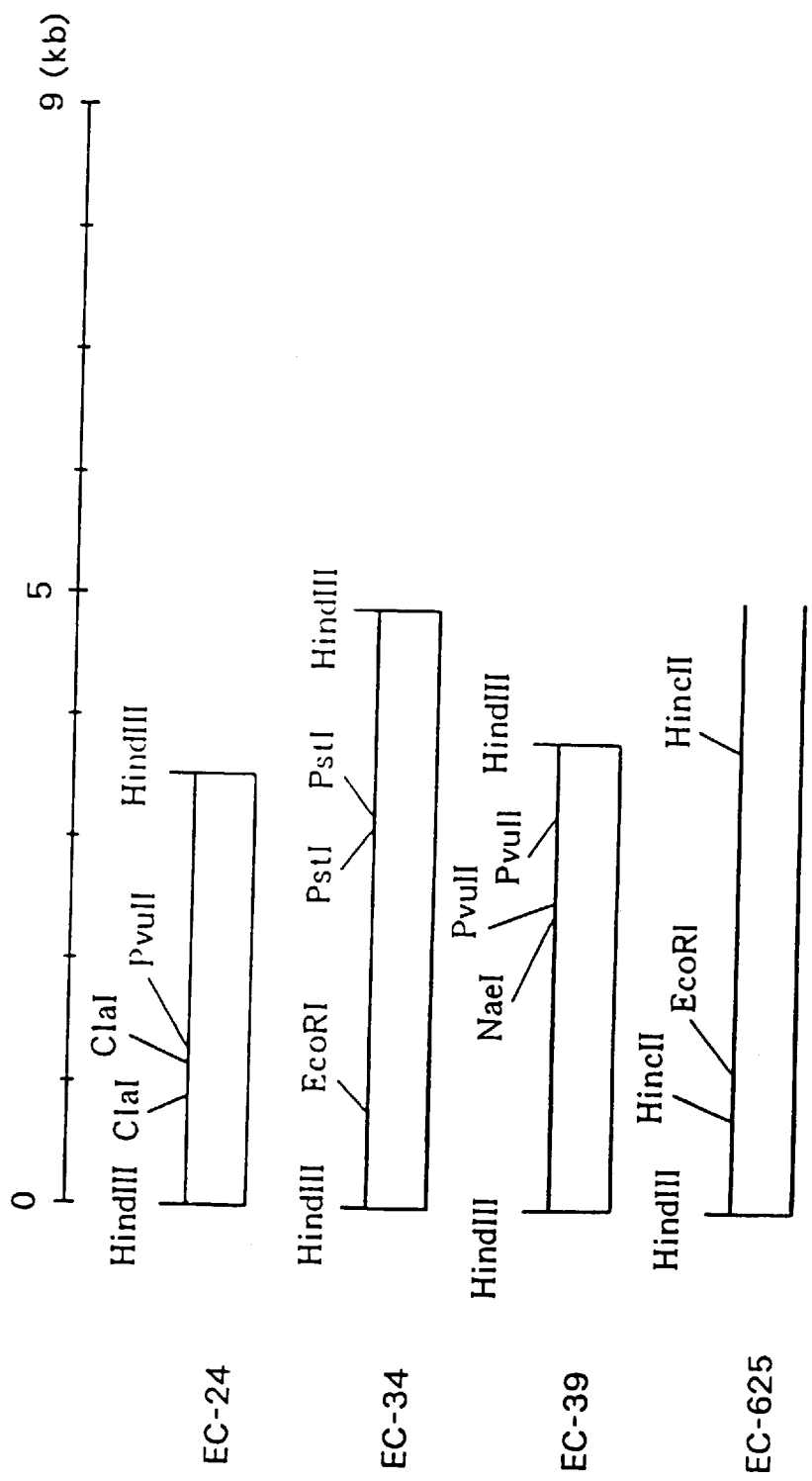
FIG. 5 is a restriction enzyme map of HindIII fragment on probe for detecting *Escherichia coli*.
Figure 6:
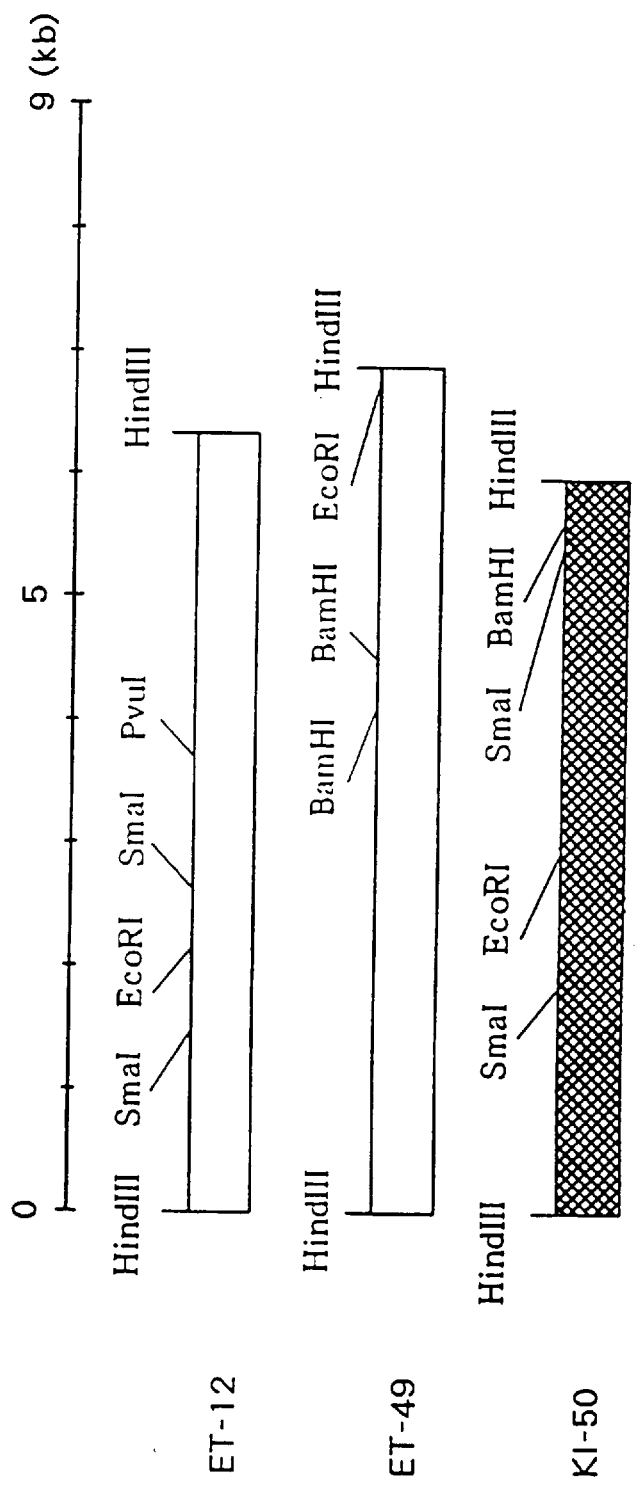
FIG. 6 is a restriction enzyme map of HindIII fragment on probe for detecting *Enterobacter cloacae* and *Klebsiella pneumonia*.

Restriction enzyme maps of each probe were also illustrated in FIGS. 1–6 respectively.

EXAMPLE 2

Evaluation on Species-Specificity of Each DNA Probe

Reactivity between each probe and DNA from causative bacteria of infectious diseases were examined acooding to the following method.

First of all, as subject strains for an examination, clinical isolates of *Staphylococcus aureus, Staphylococcus epidermidis, Enterococcus faecalis, Pseudomonas aeruginosa, Escherichia coli, Klebsiella pneumoniae*, and *Enterobacter cloacae* were isolated according to the method of Example 1 (1) above.

Then, DNA of each clinical isolate were extracted according to the method of Example 1 (2), and samples for dot-blot-hybridization were obtained by spotting certain amount (e.g., 5 µl) of DNA to nylon filter and selecting the isolates denatured with alkaline. Hybridization on DNA probes prepared from each subjected bacterium and labelled with biotin (Bio-dUTP; BRL) were performed overnight according to Manual of Maniatis, supra, under the condition of 45% formamide, 5xSSC, 42° C.

Samples obtained through overnight hybridization were washed twice with 0.1xSSC, 0.1% SDS for 20 minutes at 55° C., then, were detected the color reaction with Streptavidin-ALP conjugates (BRL), and evaluated the hybridization.

Experimental results on reactivity between each probe and DNA of each clinical isolate are illustrated in the following table 2 (i)–(vi). With regard to a denotation in the tables, denotation of "+" refers to the presence of a signal on hybridization, while that of "−" refers to the absence of a signal on hybridization.

TABLE 2

(i)

|  | SA-7 | SA-24 | SA-36 | SA-77 |
|---|---|---|---|---|
| Staphylococcus aureus | + | + | + | + |
| Staphylococcus epidermidis | − | − | − | − |
| Enterococcus faecalis | − | − | − | − |
| Pseudomonas aeruginosa | − | − | − | − |
| Escherichia coli | − | − | − | − |
| Klebsiella pneumoniae | − | − | − | − |
| Enterobacter cloacae | − | − | − | − |

(ii)

|  | SE-3 | SE-22 | SE-32 | SE-37 |
|---|---|---|---|---|
| Staphylococcus aureus | − | − | − | − |
| Staphylococcus epidermidis | + | + | + | + |
| Enterococcus faecalis | − | − | − | − |
| Pseudomonas aeruginosa | − | − | − | − |
| Escherichia coli | − | − | − | − |
| Klebsiella pneumoniae | − | − | − | − |
| Enterobacter cloacae | − | − | − | − |

(iii)

|  | S2-1 | S2-3 | S2-7 | S2-27 |
|---|---|---|---|---|
| Staphylococcus aureus | − | − | − | − |
| Staphylococcus epidermidis | − | − | − | − |
| Enterococcus faecalis | + | + | + | + |
| Pseudomonas aeruginosa | − | − | − | − |
| Escherichia coli | − | − | − | − |
| Klebsiella pneumoniae | − | − | − | − |
| Enterobacter cloacae | − | − | − | − |

(iv)

|  | P2-2 | P2-7 | P2-17 | P2-5 |
|---|---|---|---|---|
| Staphylococcus aureus | − | − | − | − |
| Staphylococcus epidermidis | − | − | − | − |
| Enterococcus faecalis | − | − | − | − |
| Pseudomonas aeruginosa | + | + | + | + |
| Escherichia coli | − | − | − | − |
| Klebsiella pneumoniae | − | − | − | − |
| Enterobacter cloacae | − | − | − | − |

(v)

|  | EC-24 | EC-34 | EC-39 | EC-625 |
|---|---|---|---|---|
| Staphylococcus aureus | − | − | − | − |
| Staphylococcus epidermidis | − | − | − | − |
| Enterococcus faecalis | − | − | − | − |
| Pseudomonas aeruginosa | − | − | − | − |
| Escherichia coli | + | + | + | + |
| Klebsiella pneumoniae | + | + | + | + |
| Enterobacter cloacae | + | + | + | + |

TABLE 2-continued (vi)

|  | ET-12 | ET-49 | KI-50 |
|---|---|---|---|
| Staphylococcus aureus | − | − | − |
| Staphylococcus epidermidis | − | − | − |
| Enterococcus faecalis | − | − | − |
| Pseudomonas aeruginosa | − | − | − |
| Escherichia coli | + | + | + |
| Klebsiella pneumoniae | + | + | + |
| Enterobacter cloacae | + | + | + |

Apparently from Table 2 above, each probe have reacted only with DNA obtained from origin strain (or relative strain thereof) and not reacted (hybridized) with any DNA obtained from strains except for strains from the origin strain, therefore, their specificity have been confirmed.

EXAMPLE 3

Analysis of Base Sequence

Base sequence of DNA probes (total 23 probes) of the present invention, which have been confirmed their specificity to the origin species in the Examples 1 and 2, were sequenced according to the following method.

(1) Preparation of Plasmid DNA

Escherichia coli K-12. JM109 transformants, wherein the subcloned insert fragments (to be seqeuenced) is contained in pGem-3Z (Promega), was inoculated in 5 ml of Luria-Bactani Medium (bacto-tryptone, 10 g/lL: bacto-yeast extract, 5 g/lL; NaCl, 10 g/lL; adjusted pH to 7.0 with 5N NaOH) and cultivated overnight.

Culture liquid was centrifuged (5,000 rpm, 5 min.) and collected the bacteria. 100 µl of solution of 50 mM glucose/ 50 mM Tris-HCl (pH8.0)/,10 mM EDTA containing 2.5 mg/ml of lysozyme (Sigma) was added to precipitate, and left at room temperature for five minutes. 0.2M NaOH solution containing 1% of sodium dodecyl sulfate (Sigma) was added to the suspension so obtained and mixed therewith. 150 µl of 5M pottasium acetate solution (pH 4.8) was further added thereto and mixed therewith, then iced for 15 minutes.

Supernatant obtained by centrifugation (15,000 rpm, 15 min.) was treated with phenol/CHCl$_3$ and added thereto ethanol of two times volume, then precipitate was obtained by centrifugation (12,000 rpm, 5 min.). This precipitate was dissolved in 100 µl of solution of 10 mM Tris-HCl (pH7.5) /0.1 mM EDTA and added thereto 10 mg/ml RNaseA (Sigma) solution, then left it at room temperature for 15 minutes.

300 µl of 0.1M sodium acetate solution (pH4.8) was added to this preparation and treated with phenol/CHCl$_3$, then precipitate was obtained by adding ethanol to supernatant. DNA samples were prepared by drying this precipitate and dissolving in 10 µl distilled water.

(2) Pretreatment for Sequencing

Pretreatment for sequencing was performed with Auto-Read ™ Sequencing Kit (Pharmasia).

Concentration of DNA to become a template was adjusted to 5–10 µg in 32 µl. 32 µl of template DNA was transferred to 1.5 ml mini-tube (Eppendolf), and added thereto 8 µl of 2M NaOH solution, then mixed gently therewith. After instant centrifugation, it was left at room temperature for 10 minutes.

7 µl of 3M sodium acetate (pH 4.8) and 4 µl of distilled water, then 120 µl of ethanol were added thereto then mixed therewith, and left for 15 minutes on dry ice. DNA which have been precipitated by centrifugation for 15 minutes were collected, and supernatant was removed carefully. The precipitate so obtained were washed with 70% ethanol and centrifuged for 10 minutes. Then, the supernatant was removed carefully again and dried the precipitate under the reduced pressure.

The precipitate was dissolved in 10 µl of distilled water, then 2 µl of fluorescent primer (0.42 $A_{2\,6\,0}$ unit/10 ml, 4–6 pmol) [M13 Universal Primer; 5'-Fluorescein-d[CGACGTTGTAAAACGACGGCCAGT]-3' SEQ ID No:24 (1.6 pmol/µl; 0.42 $A_{260}$ unit/ml); M13 Reverse Primer, 5'-Fluorescein-d[CAGGAAACAG CTATGAC]-3' SEQ ID No:25 (2.1 pmol/µl ; 0.42 $A_{2\,6\,0}$ unit/ml) ] and 2 µl of saline for annealing were added thereto, and mixed gently.

After instant centrifugation, they were heat-treated at 65° C. for 5 minutes and rapidly transferred it to a circumstance of 37° C. and kept the temperature for 10 minutes. After keeping the temperature, it was left at room temperature for 10 minutes or more and centrifugated instantly. Then, samples were prepared by adding thereto 1 µl of an elongation saline and 3 µl of dimethyl sulfoxide.

Four mini-tubes have been identified with one of marks of "A","C", "G" and "T", and, according to the mark, 2.5 µl of A Mix (dissolved ddATP with dATP, dCTP, $c^7$dGTP and dTTP), C Mix (dissolved ddCTP with dATP, dCTP, $c^7$dGTP and dTTP), G Mix (dissolved ddGTP with dATP, dCTP, $c^7$dGTP and dTTP), or T Mix (dissolved ddTTP with dATP, dCTP, $c^7$dGTP and dTTP) were poured into each identified tube. Each solution was preserved in freezed condition, and the solution was heated at 37° C. for one minute or more to use it.

2 µl of diluted T7DNA polymerase (Pharmacia; 6–8units/2 µl) was added to DNA sample, and completely mixed by pipetting or mixing it gently. Immediately after completing the mixing, these mixed solution was poured into 4.5 µl of four-types solution respectively which have kept the certain temperature. Fresh tips were used at the time of pouring.

The solution have been kept for five minutes at 37° C., then 5 µl of termination solution were poured into each reaction-solution. Fresh tips were used for pouring. Immediately after keeping the solution for 2–3 minutes at 90° C., it was cooled on ice. 4–6 µl/lane of the solution was applied to the electrophoresis.

(3) Sequencing on Base Sequence

Sequencing on each base sequence of probes, disclosed in Examples 1 and 2, having the specificity against *Staphylococcus aureus* or *Staphylococcus epidermidis* were performed with A.L.F. DNA Sequencer System (Pharmacia) under an electrophoresis condition of 45° C. for 6 hours.

Then, base sequences of the probes (SEQ ID.No.) prepared from each causative bacteria of the infectious diseases and listed in the following table 3 were disclosed in the sequence listing attached hereto.

TABLE 3

| SPECIES | Probes (SEQ ID. No.) |
|---|---|
| *Staphylococcus aureus* | SA-7 (1), SA-24 (2) |
|  | SA-36 (3), SA-77 (4) |
| *Staphylococcus epidermidis* | SE-3 (5), SE-22 (6) |
|  | SE-32 (7), SE-37 (8) |
| *Enterococcus faecalis* | S2-1 (9), S2-3 (10) |

TABLE 3-continued

| SPECIES | Probes (SEQ ID. No.) |
|---|---|
|  | S2-7 (11), S2-27 (12) |
| *Pseudomonas aeruginosa* | P2-2 (13), S2-7 (14) |
|  | P2-17 (15), P4-5 (16) |
| *Escherichia coli* | EC-24 (17), EC-34 (18), |
|  | EC-39 (19), EC-625 (20) |
| *Klebsiella pneumoniae* | KI-50 (23) |
| *Enterobacter cloacae* | ET-12 (21), ET-49 (22) |

Thereby, genetic information concerning the specific site of each causative bacteria of the infectious diseases (or relative bacteria thereof) have been clarified.

According to probes of the present invention, for example, causative bacteria of the infectious diseases which have incorporated into the phagocyte can be directly detected, and rapidly and exactly identified without proliferating the bacteria. That is to say, according to the diagnosis using the probe of the present invention, identification of the bacteria can be realized with single specimen, then, reduced the necessary time for diagnosis to about one to two day(s). while the conventional method (with low detection rate) required 3–4 days, and improved remarkably the detection rate. Therefore, this invention can provide an objective factors for the treatment of bacteremia, then realize the effective treatment in the early stage of the infectious diseases, and expect to reduce the mortality.

Then, by clarifying the base sequences of probes which specifically react with primary bacteria of the infectious diseases, these probes can be prepared artifically. Further, a part of information on the analyzed base sequences may be used for rapidly diagnosing the causative bacteria by amplifying DNA of causative bacteria of the infectious diseases in the clinical specimen with PCR technique and primers prepared by making use of said information.

Further, by comparing base sequences of Genomic DNA in the clinical specimen with that of the present invention, rapid identification of the species of the causative bacteria of infectious diseases can be realized.

As stated above, the present invention provide desirable probes for diagnosing the infectious diseases, then expect utilities as a factor to prepare primers for PCR and standard sequence for a comparison with Genomic DNA in the clinical specimen, and further expect an effect to provide valuable hints for preparing and developing the other probes which specifically react with causative bacteria of the infectious diseases.

Then, since the base sequences disclosed in the present application was obtained by random-cloning the Genomic DNA of clinical isolates, utilities of the base sequences of the present invention should be extended to the complementary strands thereof.

Further, although it may be thought that DNA obtained from the wild strains contain the mutated portion, apparently from the disclosure of the Examples above, said mutated DNA portion would not affects the utilities to be derived by the present invention comprising the specificity of the probes of the present invention in the hybridization for a diagnosis of the infectious diseases, and an usage of the information on the base sequences disclosed in the present application to design the primers for PCR technique to realize a rapid diagnosis of the infectious diseases.

We claim:

1. A probe composition for detecting *Staphylococcus epidermidis*, wherein the probe composition consists essentially of (a) the DNA of any one of SEQ ID NOS:5 through 8, or
(b) the complement of (a).

2. A method for detecting the presence of *Staphylococcus epidermidis* in a sample comprising the steps of contacting nucleic acid from said sample with the probe composition of claim 1 and detecting hybridization of the nucleic acid from said sample with DNA in said probe composition as an indication of the presence of *Staphylococcus epidermidis*.

* * * * *

UNITED STATES PATENT AND TRADEMARK OFFICE
CERTIFICATE OF CORRECTION

PATENT NO.   : 5,770,375
DATED        : June 23, 1998
INVENTOR(S)  : Ohno et al.

It is certified that error appears in the above-identified patent and that said Letters Patent is hereby corrected as shown below:

Title page,
Item [75], Inventors, please delete "Kobe" and insert -- Hyogo -- and please delete "Higashi" and insert -- Osaka --, therefor.

Item [30], Foreign Application Data, please insert -- July 7, 1993 PCT/JP93/00936 --, therefor.

Item [56], References Cited, OTHER PUBLICATIONS, please delete "aeruginosein" and insert -- aeruginose in --, therefor.

Column 2,
Line 16, please delete "(T70%)" and insert -- (70%) --, therefor.
Line 19, start new paragraph beginning with "Since the…", therefor.

Column 3,
Line 59, please delete "Bio-Nleryu" and insert -- BioMeryu", therefor.

Column 4,
Lines 17-18, please delete "$^{3}_{2}$P-dCTP" and insert -- $^{32}$P-dCTP --, therefor.
Line 58, please delete "acooding" and insert -- according --, therefor.

Column 6,
Line 31, please delete "seqeuenced" and insert -- sequenced --, therefor.
Line 43, please delete "pottasium" and insert -- potassium --, therefor.
Line 61, please delete "Pharmasia" and insert -- Pharmacia --, therefor.

UNITED STATES PATENT AND TRADEMARK OFFICE
CERTIFICATE OF CORRECTION

PATENT NO.   : 5,770,375
DATED        : June 23, 1998
INVENTOR(S)  : Ohno et al.

It is certified that error appears in the above-identified patent and that said Letters Patent is hereby corrected as shown below:

Column 7,
Line 13, insert -- ( -- before "SEQ" and insert -- ) -- after "24", therefor.
Line 16, insert -- ( -- before "SEQ" and insert -- ) -- after "25", therefor.

Signed and Sealed this

Tenth Day of September, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 8959 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA- 7

( x i ) SEQUENCE DESCRIPTION: SEQ ID NO:1:

```
AAGCTTTATC TGCTGAATAT ACCGCATTTT TTATCTTGTT AATTGTCGGC ACATTTCTT     60
CAATAGTTAA ACCTGCTTTG TTAGCTTCTT CTAATAATGC TCGAGTTACT GTTTATTAAA   120
TGTTCATTCG CTTTTCAACG ACAACTGACG AACCAGTATC TGTTAGCTTA GACGCAACAG   180
CGTTAATCTT CTGATTCACC TTAAATTCTA CATCTGCTTT TTGAGGCTGC TTACGTAGTG   240
TCCCGGTAAT TTCATGTGTA AACTTAGATG GGATGTAAAT ACCTGCAAAA TATTTACCCA   300
TTTTTATCTC ATGATCAGCT TTCTCTCTAC TTACAAACTG CCAATCAAAA CTTTTATTTT   360
TCTTGAGTGT ATTAACCATC GTATTACCGA CATTAACTTT TTTCCCTCTG ATTGTGTCGC   420
CTTTATCTTC ATTAACGACT GCGACCTTGA TGTGTCCCGT GTTGCCATAT GGATCCCACA   480
TTGCCCATAA GTTAAACCAA GCGTAGAACG ATGGCAAAAT AGCTAAGCCT GCTAAGATAA   540
TCCACACAGC TGGCGTCTTA GCTACTTTCT TCAGATCCAT TTTAAATAAT TTAAATGCGT   600
TCTTCATTGT CACACTCCTA TGTAGGAATT ATTCATATTT TTTATATATT TTTTGTAAAT   660
TAATTTATTT TTGCGTTGTG AATTAGTATA ATCAATTTAC TGGAAGATAT TTAGTCGATT   720
GATACCTATC AACTATTTTC AGCATACGAT AAATTATAAC AAATCATAGT TTATTATCAC   780
ACTTAATTAT TATATTTTTC AAGGGAGAAT ACGAAATATG CCTAAAAATA AAATTTTAAT   840
TTATTTGCTA TCAACTACCC TCGTATTACC TACTTTAGTT TCACCTACCG CTTATGCTGA   900
TACACCTCAA AAAGATACTA CAGCTAAGAC AACATCTCAT GATTCAAAAA AATCTAATGA   960
CGATGAAACT TCTAAGGATA CTACAAGTAA AGATACTGAT AAAGCAGACA ACAATAATAC  1020
AAGTAACCAA GACAATAACG ACAAAAAATT TAAAACTATA GACGACAGCA CTTCAGACTC  1080
TAACAATATC ATTGATTTTA TTTATAAAGA ATTACCACA AACCAATATA AACCAATTGC   1140
TAACCAAAAA TAAATACGAT GATAATTACT CATTAACAAC TTTAATCCAA AACTTATTCA  1200
ATTTAAATTC GGATATTTCT GATTACGAAC AACCTCGTAA TGGCGAAAAG TCAACAAATG  1260
ATTCGATAAA AACAGTGACA TAGCATCAAA AATGACACTG ATACGCAATC ATCTAAACAA  1320
GATAAAGCAG ACAATCAAAA AGCACCTAAA TCAAACAATA CAAAACCAAG TACATCTAAT  1380
AAGCAACCAA ATTCGCCAAA GCCAACACAA CCTAATCAAT CAAATAGTCA ACCAGCAAGT  1440
GACGATAAAG CAAATCAAAA ATCTTCATCG AAAGATAATC AATCAATGTC AGATTCGGCT  1500
TTAGACTCTA TTTTGGATCA ATACAGTGAA GATGCAAAGA AAACACAAAA AGATTATGCA  1560
TCTCAATCTA AAAAAGACAA AAATGAAAAA TCTAATACAA AGAATCCACA GTTACCAACA  1620
CAAGATGAAT TGAAACATAA ATCTAAACCT GCTCAATCAT TCAATAACGA TGTTAATCAA  1680
```

| | | | | | | |
|---|---|---|---|---|---|---|
| AAGGATACAC | GTGCAACATC | ATTATTCGAA | ACAGATCCTA | GTATATCTAA | CAATGATGAT | 1740 |
| AGCGGACAAT | TTAACGTTGT | TGACTCAAAA | GATACACGTC | AATTTGTCAA | ATCAATTGCT | 1800 |
| AAAGATGCAC | ATCGCATTGG | TCAAGATAAC | GATATTTATG | CGTCTGTCAT | GATTGCCCAA | 1860 |
| GCAATCTTAG | AATCTGACTC | AGGTCGTAGT | GCTTTAGCTA | AGTCACCAAA | CCATAATTTA | 1920 |
| TTCGGTATCA | AAGGTGCTTT | TGAAGGGAAT | TCTGTTCCTT | TTAACACATT | AGAAGCTGAT | 1980 |
| GGTAATAAAT | TGTATAGTAT | TAATGCTGGA | TTCCGAAAAT | ATCCAAGCAC | GAAAGAATCA | 2040 |
| CTAAAGATT | ACTCTGACCT | TATTAAAAAT | GGTATTGATG | GCAATCGAAC | AATTTATAAA | 2100 |
| CCAACATGGA | AATCGGAAGC | CGATTCTTAT | AAAGATGCAA | CATCACACTT | ATCTAAAACA | 2160 |
| TATGCTACAG | ATCCAAACTA | TGCTAAGAAA | TTAAACAGTA | TTATTAAACA | CTATCAATTA | 2220 |
| ACTCAGTTTG | ACGATGAACG | CATGCCAGAT | TTAGATAAAT | ATGAACGTTC | TATCAAGGAT | 2280 |
| TATGATGATT | CATCAGATGA | ATTCTGTTCC | TTTTAACACA | TTAGAAGCTG | ATGGTAATAA | 2340 |
| ATTGTATAGT | ATTAATGCTG | GATTCCGAAA | ATATCCAAGC | ACGAAAGAAT | CACTAAAAGA | 2400 |
| TTACTCTGAC | CTTATTAAAA | ATGGTATTGA | TGGCAATCGA | ACAATTTATA | AACCAACATG | 2460 |
| GAAATCGGAA | GCCGATTCTT | ATAAAGATGC | AACATCACAC | TTATCTAAAA | CATATGCTAC | 2520 |
| AGATCCAAAC | TATGCTAAGA | AATTAAACAG | TATTATTAAA | CACTATCAAT | TAACTCAGTT | 2580 |
| TGACGATGAA | CGCATGCCAG | ATTTAGATAA | ATATGAACGT | TCTATCAAGG | ATTATGATGA | 2640 |
| TTCATCAGAT | GAATTCAAAC | CTTTCCGCGA | GGTATCTGAT | AGTATGCCAT | ATCCACATGG | 2700 |
| CCAATGTACT | TGGTACGTAT | ATAACCGTAT | GAAACAATTT | GGTACATCTA | TCTCAGGTGA | 2760 |
| TTTAGGTGAT | GCACATAATT | GGAATAATCG | AGCTCAATAC | CGTGATTATC | AAGTAAGTCA | 2820 |
| TACACCAAAA | CGTCATGCTG | CTGTTGTATT | TGAGGCTGGA | CAATTTGGTG | CAGATCAACA | 2880 |
| TTACGGTCAT | GTAGCATTTG | TTGAAAAAGT | TAACAGTGAT | GGTTCTATCG | TTATTTCAGA | 2940 |
| TCAATGTTAA | AGGATTAGGT | ATCATTTCTC | ATAGAACTAT | CAATGCAGCT | GCCGCTGAAG | 3000 |
| AATTATCATA | TATTACAGGT | AAATAAGTAT | TATTAAACCC | GCAAAATTTA | TAAGTATAAA | 3060 |
| CAAGGAGTTC | GGACTTAAAC | ATATTTCTGT | TCATAAGTCC | GATTTCTTAT | TCAATTAAAC | 3120 |
| CCGAGGTATT | CAGTTCGAAC | GCCTCGGGTC | ATTTTATATA | AATATATTAT | TTTATGTTCA | 3180 |
| AATGTTCCTC | ATCATATCCG | TTTCAATTGT | CATCTCACAC | ATTTTATAAA | TATGAGCAAA | 3240 |
| TGTACTTATT | TTCAAACATT | ACTGCCTAGC | TTTAATTGAC | GTTATATTAA | CTATAAACTA | 3300 |
| CTTTTCCATG | ACTCTACGGA | TTCAATGTCA | CATGAGCGTG | ATAAATTTG | TTCAATAATA | 3360 |
| AAGTCATGTT | TATCATCTGA | TCTATCACCA | ACAGCATCTT | CTAAAACAGT | AATATAATAG | 3420 |
| TCTTTATCTA | CACTTTCTAA | TGCCGTGCTC | AATACAGCTC | CACTCGTAGA | GACACCCGTT | 3480 |
| AATACTAAAT | GATTAATATC | ATTTGCACGT | AAATAAACTT | CCAAGTAACT | ACCTGTAAAT | 3540 |
| GCGCTAAAGC | GTCGCTTAGA | AATAATCGGC | TCATCTTCTA | GTGGTGCTAA | ATCTTCAAGT | 3600 |
| ATTCGTGTAG | ATGCATCTGC | TTCAGTAATC | GCATATCCTT | GAGCTTAAT | TGTTGAAAAC | 3660 |
| ACTTTATTAC | TCGAGGAGAC | ATCATTAAAA | TGCTTATCTA | ACACTAAACG | TATGAAAATG | 3720 |
| ACTGGTATTC | GATGTTGTCT | TGCTGCTTCA | ATTGCTCTCT | GATTCGCTTT | AATAATATTT | 3780 |
| TTATTCTAG | GTACACTACT | CGCTATACTT | CTTGCATATC | CAAACTAATA | GCGCCGTTTT | 3840 |
| TCGAGACATC | TTCATTCTCC | TTTACTTCTG | TAGTTCTAAG | TCGTTAAATT | CATTATAACG | 3900 |
| TTAAAATGAT | GGACAATCTA | TTCATTGCAT | TTTGCATATA | CTTCACAATA | ATTTAAGGGG | 3960 |
| GAAATAAGAC | GTCTTATATA | CTTAAAAAAA | TATATAGATG | CTCTTCCCCC | AATATAATTA | 4020 |
| TGCTTTATTT | TTCAACTTAT | TGCGTCGTGA | TAACCAAATC | ATTAGTACAC | CCATTGCACC | 4080 |

| | | | | | |
|---|---|---|---|---|---|
| AACAATTACA | GATATCGGCA | ACCAATGTTC | TTTTATCGTT | TCCCCGCTTT | AGGCAAGATA 4140 |
| CATTACCATC | AGCATTTAAT | AATCCACTTA | ACAATCCATT | ACCTTTACCA | AGTGTTACGT 4200 |
| CTTTTCTGGC | TTTGGTGTGG | GTATATCTGG | AATACTGTCT | AATAAATTTG | ATCCTTGATT 4260 |
| CATTAAATTT | GCTAACTTAT | TTAAATCCGT | TGTTTTCCCA | TTTTTATTCA | ATCGATCTAG 4320 |
| TAAACTTGGA | CGATTACTA | TTGGTGATAA | AATATAGTCT | ATATCTTTTT | TCGTTTGATT 4380 |
| GAGTCTCTTT | TGTAAATTCA | ATAAATCATC | CGCTTTACCA | TTCAATGCCG | ATTAACTAA 4440 |
| ATTAAAAATT | TTATTTTGAT | CTGTTTCTAT | TTAGTAATT | AAATCTGCCA | GTAATTTGC 4500 |
| CTTTTGTCTT | TCTATACGTG | TTGCTAAAAT | CGTTTCAATT | GCTTGCTTTT | TATCTTTGGC 4560 |
| ATTATTCAAA | ATTGCTTTTA | ATATATCATC | TGAAGACGTG | TCGCCAGTTG | ATGCAAAATG 4620 |
| TTTCTTCAAT | TGGTCAACGA | TTTGGCGATT | TGATAATCCT | TTATTCGTCC | AATCTTTAGC 4680 |
| CAATTTATCT | GCTTCAGCTT | TTCCTAATTT | CGTTTGTAAG | ATTTGAGAAA | TCAATAGCGA 4740 |
| CTTATCTTGT | GATTGATCAA | TCAATGACGT | TAATAAATCA | TCACTCGTTG | TCAGAGATAG 4800 |
| TTGATCAATA | TGACGAGTAA | TTTGATCTGC | AATTTGTTGA | TCTGTTTTAC | CATCAACACG 4860 |
| TATATCTTTT | AGAATTTTAT | CTGCCTCGTC | TTTATTAAAT | ATACTTTCTA | AAATGCTTTG 4920 |
| TGTAGCATAC | TTTTTATCAT | CAGTACGTGC | AAGTTCTTCC | AAAATAATAT | TTCGTTGACT 4980 |
| TTTTATACGC | TCTTTCGTCT | TATTTACTTC | GCTCATTAAG | TCTGATTTTT | GATTTTAGG 5040 |
| AAGTTGCGTA | TTTGCAATAC | GTTGATCTAA | AGATTGTAAC | GTATTCAGTT | TATGATATGT 5100 |
| GTAATGTTGC | GTTGAGGCAT | TACTTTAGC | CAATTTTCA | ATCATAGCAT | GATTAATTTT 5160 |
| ATCGCTTCCT | TGTAATTTAT | CAGTGAGTTG | ATTACTATGG | CTTTGATTCT | CTTCATTTGA 5220 |
| AAGAAATTTA | TTTAACACAA | CATGTCCAGA | ACCATCATTA | TTTGGCGTTT | TAGCTACTTC 5280 |
| ATGATTACTA | TCTGTTGTAG | ACACTGCCGG | ATCTTTCGAT | GCATCTTTCA | ATGCATCTTT 5340 |
| CGATTTGTGT | ATTTGCTGAT | TCAAATGGTC | TAGGTCTTCT | AACGCCTTAT | TTACCATTGC 5400 |
| TTCATCATTT | TTATCATCTT | TTTCTCCATA | TTTTGTTGTA | GCCGTTTGTG | ACATATCATT 5460 |
| TTTCATTGCA | TTAAGATCGT | CCTCGCCACT | TTGTTGACCC | CTATCAACAT | TGAAGAAAC 5520 |
| CTCATTTAAA | TCTTTAAGCA | ATTGATCTAA | TTACTGTCT | ATATCACTTT | GACCGTTCAT 5580 |
| TTCAGTGTGA | GAACTTTTAT | TTTCTTTGCT | ATCCAACTCA | TTAGCTCGTT | TTATGATTTC 5640 |
| ATCTATTTGC | GATGCTGTTT | TCGCTTCATT | TAGTTGTGCT | TTATAATGTG | CTTTAGATGA 5700 |
| AGCCGATAAC | TGTTTTAATT | GCTCAATTTG | ACGAATTGCT | TTGTCAACTT | TGTCTAATAA 5760 |
| ATCTTGCTTA | GATAATATCT | CTTTTGAAAT | TTCAGTATCC | TTTTCAGATG | CAGCTTGGGC 5820 |
| ATCGTACGGC | AAGATATTCG | TTAAAATGAT | ACTTGACGCC | ATCATTGTCG | AACACGATAA 5880 |
| CTTTACATAT | AATTGAAACG | GTTTCCCTCG | ATATTTAGCC | ATCAACATAC | TCCTTTCTCA 5940 |
| CTTACTTCCT | TCAAAGAATT | ACATACTATT | ATATACCTGT | TTACAAGAAA | TTTACACTTA 6000 |
| TCTATCTAGT | TATTGTTGTT | AGTAATTATC | AACTTATTAC | TTAGCTTATA | TTTAAGTAAA 6060 |
| CAAAAAAGCA | TGACGTAATA | TCATATTGTC | CATGTCGCTA | ACATCATATT | ACGTCAAATC 6120 |
| TTTTAAATTA | AATGATGCTT | TATTTAGAC | TGCTTTTTCT | TTTTAGCTTT | CGAGCGCCTG 6180 |
| TTTAAAAACT | TGCTCGAATT | GTTCACGCGA | GATTTCGTGT | GCATGTGCTT | TTTGTGCTAA 6240 |
| TAAAGCATCT | CGAAACTGTT | GTTGATCTTT | CAAACTTTCT | AACATTTGTA | TTAATTGGTC 6300 |
| TTTACTTTCC | ATTGTTATCT | CATCATTATG | CTCAAATAAG | TGCTCTGATA | ATGTTACTTT 6360 |
| AGCATGGTGT | GCGGTTTGAC | GATAACCTAA | AATCAACAAC | TCATAGTCAA | ACGCTTGTTC 6420 |
| CACCGCATTT | AAAATTTCAT | TACCCTCATT | GATATCAAGA | TAAATATCAC | ATAACTGGTA 6480 |

```
TAGTTCATTT ACCCTGTCAA TATAATAGAT GGTATAAGTG CACATTAGCA TATTGATCAA  6540
GTTGCATTAG CTTATCAGAC ATCTCTGTAA TAGCAGCGAT GTGAAAATTA AAATCTGGTA  6600
AAGTTTCAAC CAATACCTTG ATGTTACGAA GTTGATCCGA GTTAGTTAAT ATTACAATTT  6660
CTTTAGTATA TCTATTACGA CTACGATAGT TATATAGATA TCCGCCTTGT AAAATACGAG  6720
ATTGAACCTT TGCGTCTGCT ATATTGAGCA TCGTTTCATA TTCGTTTTTA TCTGGAATAA  6780
TAATATTACA ATGTCGTTTC ATATCACCTT TACACATCAA TTGCATATTT CCCGGGACAT  6840
TACCATTACA GTGTTCTTGC CATACCAAAA CATCACTACC TTTTGATGGC AAATTATATA  6900
ACACTGAAAA TGGTAGGGCT AGTGAGTTAA TAACGAAATG ATGTTCCGTA ATTTCAAGTT  6960
GCTTGATAAA AAATAATACG AATGCGAGCT TGAAGGGAA AAAGTAAGAC TTCCCTTGCC  7020
AATCCAATAT GACATCAGAT GTTACAAAAT TTTCATAAAT CACTTCTTTA CCTTCTGCTG  7080
TCATATATTT CTTCAAGATC GCTTTACGAT TTAAATCGTA ACAGTTTGTG CAATTTAATA  7140
CCATTCTTAG AATAATAATC GACAAATCGG ACACGTTGTT GGTCATCAAA CCATTCGACA  7200
CGACTAACAA TTCTAGGGCG CTCTCCACTT TGATAAAATA TTTTGCCTCG TAGACGTCCC  7260
ATATCATTAA TTGTAGCCGA ATTGTTGTTA CCTTTAATTT CCCAAAAAGC TGGTACAGTA  7320
ACCTGATTAA AAAATCGTGG TTTCATATTT TCTGTATTAT GATTATCTGC AAAAAATTGA  7380
TACGGTGATA TAACATCGTC CGGTAAAAAG CCATTGTCAT TGAGTACAAT TGTTAAATCT  7440
TCTTCCAACT TACTGGCTTT AAAAGACTCA TATAACTTTC GTGAATGATC GTTAAAGTAA  7500
TCAAATAATT TAATCATGTA GCACCTCTTG AACTAATGTT TCCCATTTTA AAATAATATC  7560
TTGAGTCATA AATTGCTGTG CCACTTCATA AGAGATGTCA TGTGGTGCCT GGGGACCATT  7620
GTTAAAATAC ATTACAATGG CATGAGCTAG TTTTGCGATA ACATCATCCA CACTATCTTC  7680
GTCGGTATCA AAAGGTACCA AGTAGCCATT TTCCCCATCT CGAATAAAGG TTGGGTTACC  7740
ATAATTCACA TTTAATCCAA TCATACCTAG TCCTGAGCCT ACCGCTTCCA TTAGTGTTAA  7800
CCCAAAACCT TCGCTAGTTG ATGCAGAAAG AAATAACTCA TAATCATTAT AAATTTCATC  7860
AAGTTTAACA TGCCCTTAGT AAACCGAATA TAATCTTGTG CGCGGTGTGT ATCAATAATT  7920
TTACGCAGTC GCGTCTTCTC GCTACCTTCT CCATAAATAT CAAATGTTAA TTCTGGCACT  7980
TGTCGTTTAG CCACGATAAC CGCCTTGACA AGCCAATCAA TATGTTTCTC ATTTGCTAAA  8040
CGAGATGCAC TAATCATCGC ATATGGCTTT CTTGATAATT TAGGATATGA TAACGCATCA  8100
ATGCTTCCCA CCGGDATAGT ATAGACACGT GGACGATAAC CTTGATATTG CTCAAATTGT  8160
CGACAAACCA TATGATTTTG AATATCTGTT GCTGTAATAA AGAAATCAAT GTATTTAGCT  8220
TTTGAAAATT GATATTCATA ATAATTGTTC CATAGTATAT GCTGCTCGCT CATCATATTA  8280
TTACTATAAT GATCAGCATG AATCACAACA CCAACTTTAC TATCACCTTT ATGCTGCAAA  8340
ACAGCCTGAC CAATATCAGA AGCGCGGTCT AATATGACAA TATCGTCTCG GGTTAAATTC  8400
AATCGTTGTA AAAGTATGC AATAAATTCC GTTTTGTTAT ACAACACCGC ATCTTCAAAC  8460
ACATATATAG AGCTGTCTCC ATCAATATAT TCGTTATAAG CGATGGAACC ATCTTCATTA  8520
TAGAATTGTC GCATATATAA TTTCGCTTTA TTATCAGCTG GTGCATAATA CTCAGAAAAT  8580
ATACGCGTAT AACTATAAAA ATCTTTACGT ACTAACATAC TATTAATTAC AATTCTGCAC  8640
GATCCACAAC ATCTTTTTGT TCATTTTGTA GATAACATGT TACAAATGAT GATTTCCCAT  8700
TAAAATATAG ACGGACTATC TTACCATTTC TTTCTCTAAA ACTAATTTCA TGACCAAGCT  8760
CACGTTCAAT GTCATCTAAC GTGTACGTTG TTGGTGCTAT AGAAATATCA CTAAAAATAC  8820
TGATACAACC AAATAACTTC TTGATCTTTA AACCCAATGT TTTGCGTTAA TGTCTGTATG  8880
```

-continued

| TTCTCTGACT | GTATAAAATC | TAAAAACACA | AATTTAGTGT | CTTGATTTGT | ACGTCTCAAT | 8940 |
| AATTTAGCAC | GGTAAGCTT | | | | | 8959 |

( 2 ) INFORMATION FOR SEQ ID NO:2:

( i ) SEQUENCE CHARACTERISTICS:
        ( A ) LENGTH: 10207 base pairs
        ( B ) TYPE: nucleic acid
        ( C ) STRANDEDNESS: double
        ( D ) TOPOLOGY: linear ( i i ) MOLECULE TYPE:Genomic DNA ( v i ) ORIGINAL SOURCE:
        ( A ) ORGANISM: Staphylococcus aureus
        ( B ) STRAIN: Clinical Isolate SA- 24

( x i ) SEQUENCE DESCRIPTION: SEQ ID NO:2:

| AAGCTTATGG | ACCTATTTTA | GGTATATTGA | TTAGTTGGCT | TGGATTAATT | TCTGGAACAT | 60 |
| TTACAGTCTA | TTTGATCTGT | AAACGATTGG | TGAACACTGA | GAGGATGCAG | CGAATTAAAC | 120 |
| AACGTACTGC | TGTTCAACGC | TTGATTAGTT | TTATTGATCG | CCAAGGATTA | ATCCCATTGT | 180 |
| TTATTTTACT | TTGTTTTCCT | TTTACGCCAA | ATACATTAAT | AAATTTGTA | GCGAGTCTAT | 240 |
| CTCATATTAG | ACCTAAATAT | TATTTCATTG | TTTTGGCATC | ATCAAAGTTA | GTTTCAACAA | 300 |
| TTATTTAGG | TTATTTAGGT | AAGGAAATTA | CTACAATTTT | AACGCATCCT | TAAGAGGGA | 360 |
| TATTAATGTT | AGTTGTGTTG | GTTGTATTTT | GGATTGTTGG | AAAAAAGTTA | GAACAGCATT | 420 |
| TTATGGGATC | GAAAAAGGAG | TGACATCGTG | AAAAAAGTTG | TAAAATATTT | GATTTCATTG | 480 |
| ATACTTGCTA | TTATCATTGT | ACTGTTCGTA | CAAACTTTTG | TAATAGTTGG | TCATGTCATT | 540 |
| CCGAATAATG | ATATGTCACC | AACCCTTAAC | AAAGGGACGT | GTTATTGTAA | ATAAAATTAA | 600 |
| AGTTACATTT | AATCAATTGA | ATAATGGTGA | TATCATTACA | TATAGGCGTG | GTAACGAGAT | 660 |
| ATATACTAGT | CGAATTATTG | CCAAACCTGG | TCAATCAATG | GCGTTTCGTC | AGGGACAATT | 720 |
| ATACCGTGAT | GACCGACCGG | TTGACGCATC | TTATGCCAAG | AACAGAAAAA | TTAAAGATTT | 780 |
| TAGTTTGCGC | AATTTTAAAG | AATTAGATGG | AGATATTATA | CCGCCTAACA | ATTTTGTTGT | 840 |
| GCTAAATGAT | CATGATAACA | ATCAGCATGA | TTCTAGACAA | TTTGGTTTAA | TTGATAAAAA | 900 |
| GGATATTATT | GGTAATATAA | GTTTGAGATA | TTATCCTTTT | TCAAAATGGA | CGATTCAGTT | 960 |
| CAAATCTTAA | AAAGAGGTGT | CAAAATTGAA | AAAAGAATTA | TTGGAATGGA | TTATTTCAAT | 1020 |
| TGCAGTCGCT | TTTGTCATTT | TATTTATAGT | AGGTAAATTT | ATTGTTACAC | CATATACAAT | 1080 |
| TAAAGGTGAA | TCAATGGATC | CAACTTTGAA | AGATGGCGAG | CGAGTAGCTG | TAAACATTAT | 1140 |
| TGGATATAAA | ACAGGTGGTT | TGGAAAAAGG | TAATGTAGTT | GTCTTCCATG | CAAACAAAAA | 1200 |
| TGATGACTAT | GTTAAACGTG | TCATCGGTGT | TCCTGGTGAT | AAAGTAGAAT | ATAAAAATGA | 1260 |
| TACATTATAT | GTCAATGGTA | AAAACAAGA | TGAACCATAT | TTAAACTATA | ATTTAAAACA | 1320 |
| TAAACAAGGT | GATTACATTA | CTGGGACTTT | CCAAGTTAAA | GATTTACCGA | ATGCGAATCC | 1380 |
| TAAATCAAAT | GTCATTCCAA | AAGGTAAATA | TTTAGTTCTT | GGAGATAATC | GTGAAGTAAG | 1440 |
| TAAAGATAGC | CGTGCGTTTG | GCCTCATTGA | TGAAGACCAA | ATTGTTGGTA | AAGTTTCATT | 1500 |
| TAGATTCTGG | CCATTTAGTG | AATTTAAACA | TAATTTCAAT | CCTGAAAATA | CTAAAAATTA | 1560 |
| ATATGAAACA | AATACAACAT | CGTTTGTCGG | TTTTAATACT | GATAAACGAT | GTTTTATTTT | 1620 |
| GTTAGTACCA | CAATAAAAGC | TAAGTTCGAA | ATGAACTTAT | AATAAATCAA | TCACAATCAC | 1680 |
| TTTGTGTTAA | AATATGTGTC | AAAGGAAGTG | AGGGTTTGTC | ATGACATTAC | ATGCTTATTT | 1740 |
| AGGTAGAGCG | GGAACAGGTA | AGTCTACGAA | AATGTTGACC | GAAATAAAAC | AAAAAATGAA | 1800 |

```
AGCAGATCCG  CTTGGAGATC  CAATCATTTT  AATTGCGCCA  ACTCAAAGTA  CATTTCAATT  1860

AGAACAAGCC  TTTGTCAATG  ATCCGGAATT  AAATGGTAGT  TTAAGAACAG  AAGTGTTGCA  1920

TTTTGAACGA  TTAAGTCATC  GTATTTTCCA  AGAAGTTGGT  AGTTATAGCG  AACAAAAGTT  1980

ATCTAAAGCT  GCAACGGAAA  TGATGATTTA  TAACATTGTT  CAAGAACAAC  AAAAGTATTT  2040

AAAACTTTAT  CAATCACAAG  CAAAATATTA  TGGGTTTAGT  GAAAAATTAA  CAGAACAAAT  2100

TCAAGATTTT  AAAAAATATG  CAGTAACGCC  TGAACATTTA  GAACACTTTA  TTGCTGATAA  2160

AAATATGCAA  ACTCGAACTA  AAAATAAGTT  AGAGGATATT  GCTTTAATAT  ACCGTGAGTT  2220

CGAACAACGC  ATTCAAAACG  AGTTTATTAC  TGGTGAGGAT  TCATTACAAT  ATTTTATTGA  2280

TTGTATGCCG  AAATCAGAGT  GGCTAAAACG  TGCTGATATA  TATATTGATG  GTTTTCACAA  2340

CTTTTCAACG  ATTGAGTATT  TAATAATCAA  AGGATTAATT  AAATATGCGA  GAGTGTCACA  2400

ATTATATTGA  CGACAGATGG  TAACCACGAT  CAATTTAGTT  TTTTAGAAAA  CCATCGGAAG  2460

TGTTACGACA  TATTGAAGAA  ATAGCAAATG  AACTCAATAT  TTCTATTGAA  CGTCAATATT  2520

TCAACCAATT  ATATCGCTTC  AATAATCAAG  ATTTAAAGCA  TCTTGAACAA  GAATTTGATG  2580

TACTTCAAAT  CAATCGAGTG  GCATGTCAAG  GTCATATCAA  TATTTTAGAA  TCTGCGACTA  2640

TGAGAGAGGA  AATAAATGAA  ATTGCGCGAC  GTATCATCGT  TGATATTCGT  GATAAGCAAT  2700

TACGATATCA  AGATATTGCA  ATTTTATATC  GTGACGAGTC  TTATGCTTAT  TTATTTGATT  2760

CCATATTACC  GCTTTATAAT  ATTCCTTATA  ACATTGATAC  AAAGCGTTCG  ATGACACATC  2820

ATCCGGTCAT  GGAAATGATT  CGTTCATTGA  TTGAAGTTAT  TCAATCTAAT  TGGCAAGTGA  2880

ATCCAATGCT  ACGCTTATTG  AAGACTGATG  TGTTAACGGC  ATCATATCTA  AAAAGTGCAT  2940

ACTTAGTTGA  TTTACTTGAA  AATTTTGTAC  TTGAACGTGG  TATATACGGT  AAACGTTGGT  3000

TAGATGATGA  GCTATTTAAT  GTCGAACATT  TTAGCAAAAT  GGGGCGTAAA  GCGCATAAAC  3060

TGACCGAAGA  TGAACGTAAC  ACATTTGAAC  AAGTCGTTAA  GTTAAAGAAA  GATGTCATTG  3120

ATAAAATTTT  ACATTTTGAA  AAGCAAATGT  CACAAGCGGA  AACTGTAAAA  GACTTTGCAA  3180

CTGCTTTTTA  TGAAAGTATG  GAATATTTCG  AACTGCCAAA  TCAATTGATG  ACAGAGCGAG  3240

ATGAACTTGA  TTTAAATGGT  AATCATGAAA  AGGCGGAGGA  AATTGATCAA  ATATGGAATG  3300

GCTTAATTCA  AATCCTTGAC  GACTTAGTTC  TAGTATTTGG  AGATGAACCA  ATGTCGATGG  3360

AACGTTTCTT  AGAAGTATTT  GATATTGGTT  TAGAACAATT  AGAATTTGTC  ATGATTCCAC  3420

AAACATTAGA  TCAAGTTAGT  ATTGGTACGA  TGGATTTGGC  TAAAGTCGAC  AATAAGCAAC  3480

ATGTTTACTT  AGTTGGAATG  AACGACGGCA  CCATGCCACA  ACCAGTAACT  GCATCAAGTT  3540

TAATTACTGA  TGAAGAAAAG  AAATATTTTG  AACAACAAGC  AAATGTAGAG  TTGAGTCCTA  3600

CATCAGATAT  TTTACAGATG  GATGAAGCAT  TTGTTTGCTA  TGTTGCTATG  ACTAGAGCTA  3660

AGGGAGATGT  TACATTTTCT  TACAGTCTAA  TGGGATCAAG  TGGTGATGAT  AAGGAGATCA  3720

GCCCATTTTT  AAATCAAATT  CAATCATTGT  TCAACCAATT  GGAAATTACT  AACATTCCTC  3780

AATACCATGA  AGTTAACCCA  TTGTCACTAA  TGCAACATGC  TAAGCAAACC  AAAATTACAT  3840

TATTTGAAGC  ATTGCGTGCT  TGGTTAGATG  ATGAAATTGT  GGCTGATAGT  TGGTTAGATG  3900

CTTATCAAGT  AATTAGAGAT  AGCGATCATT  TAAATCAAGG  TTTAGATTAT  TTAATGTCAG  3960

CATTAACGTT  TGACAATGAA  ACTGTAAAAT  TAGGTGAAAC  GTTGTCTAAA  GATTATATG   4020

GTAAGGAAAT  CAATGCCAGT  GTATCTCGTT  TTGAAGGTTA  TCAACAATGC  CCATTTAAAC  4080

ACTATGCTTC  ACATGGTCTG  AAACTAAATG  AACGAACGAA  ATATGAACTT  CAAAACTTTG  4140

ATTTAGGTGA  TATTTTCCAT  TCCGTTTTAA  AATATATATC  TGAACGTATT  AATGGCGATT  4200
```

```
TTAAACAATT AGACCTGAAA AAAATAAGAC AATTAACGAA TGAAGCATTG GAAGAAATTT    4260
TACCTAAAGT TCAGTTTAAT TTATTAAATT CTTCAGCTTA CTATCGTTAT TTATCAAGAC    4320
GCATTGGCGC TATTGTAGAA ACAACACTAA GCGCATTAAA ATATCAAGGC ACGTATTCAA    4380
AGTTTATGCC AAAACATTTT GAGACAAGTT TTAGAAGGAA ACCAAGAACC AAATGTACGA    4440
ATTAATTGCA CAAACATTAA CGACAACTCA AGGTATTCCA ATTAATATTA GAGGGCAAAT    4500
TGACCGTATC GATACGTATA CAAAGAATGA TACAAGTTTT GTTAATATCA TTGACTATAA    4560
ATCCTCTGAA GGTAGTGCGA CACTTGATTT AACGAAAGTA TATTATGGTA TGCAAATGCA    4620
AATGATGACA TACATGGATA TCGTTTTACA AAATAAACAA CGCCTTGGAT TAACAGATAT    4680
TGTGAAACCA GGTGGATTAT TATACTTCCA TGTACATGAA CCTAGAATTA AATTTAAATC    4740
ATGGTCTGAT ATTGATGAAG ATAAACTAGA ACAAGATTTA ATTAAAAGT TTAAGCTGAG     4800
TGGTTTAGTG AATGCAGACC AAACTGTTAT TGATGCATTG GATATTCGTT TAGAACCTAA    4860
ATTCACTTCA GATATTGTAC CAGTTGGTTT GAATAAAGAT GGCTCTTTGA GTAAACGAGG    4920
CAGCCAAGTG GCAGATGAAG CAACAATTTA TAAATTCATT CAGCATAACA AAGAGAATTT    4980
TATAGAAACA GCTTCAAATA TTATGGATGG ACATACTGAA GTGCACCATT AAAGTACAAA    5040
CAAAAATTGC CATGTGCTTT TTGTAGTTAT CAATCGGTAT GTCATGTAGA TGGCATGATT    5100
GATAGTAAGC GATATCGAAC TGTAGATGAA ACAATAAATC CAATTGAAGC AATTCAAAAT    5160
ATTAACATTA ATGATGAATT TGGGGGTGAG TAATAGATGA CAATTCCAGA GAAACCACAA    5220
GGCGTGATTT GGACTGACGC GCAATGGCAA AGTATTTACG CAACTGGACA AGATGTACTT    5280
GTTGCAGCCG CGGCAGGTTC AGGTAAAACA GCTGTACTAG TTGAGCGTAT TATCCAAAAG    5340
ATTTTACGTG ATGGCATTGA TGTCGATCGA CTTTTAGTCG TAACGTTTAC AAACTTAAGC    5400
GCACGTGAAA TGAAGCATCG TGTAGACCAA CGTATTCAAG AGGCATCGAT TGCTGATCCT    5460
GCAAATGCAC ACTTGAAAAA CCAACGCATC AAAATTCATC AAGCACAAAT ATCTACACTT    5520
CATAGTTTTT GCTTGAAATT AATTCAACAG CATTATGATG TATTAAATAT TGACCCGAAC    5580
TTTAGAACAA GCAGTGAAGC TGAAAATATT TTATTATTAG AACAAACGAT AGATGAGGTC    5640
ATAGAACAAC ATTACGATAT CCTTGATCCT GCTTTTATTG AATTAACAGA ACAATTGTCT    5700
TCAGATAGAA GTGATGATCA GTTTCGAATG ATTATTAAAC AATTGTATTT CTTTAGCGTT    5760
GCAAATCCAA ATCCTACAAA TTGGTTGGAT CAATTGGTGA CACCATACGA AGAAGAAGCA    5820
CAACAAGCGC AACTTATTCA ACTACTAACA GACTTATCTA AAGTATTTAT CACAGCTGCC    5880
TATGATGCTT TAAATAAGGC GTATGATTTG TTTAGTATGA TGGATGGCGT CGATAAACAT    5940
TTAGCTGTTA TAGAAGATGA ACGACGTTTA ATGGGGCGTG TTTTAGAAGG TGGTTTTATT    6000
GATATACCTT ATTTAACTGA TCACGAATTT GGCGCGCGTT TGCCTAATGT AACAGCGAAA    6060
ATTAAAGAAG CAAATGAAAT GATGGTCGAT GCCTTAGAAG ATGCTAAACT TCAGTATAAA    6120
AAATATAAAT CATTAATTGA TAAAGTGAAA AATGATTACT TTTCAAGAGA AGCTGATGAT    6180
TTGAAAGCTG ATATGCAACA ATTGGCGCCA CGAGTAAAGT ACCTTGCGCG TATTGTGAAA    6240
GATGTTATGT CAGAATTCAA TCGAAAAAAG CGTAGCAAAA ATATTCTGGA TTTTTCTGAT    6300
TATGAACAAT TTGCATTACA AATTTTAACT AATGAGGATG GTTCGCCTTC AGAAATTGCC    6360
GAATCATACC GTCAACACTT TCAAGAAATA TTGGTCGATG AGTATCAAGA TACGAACCGG    6420
GTTCAAGAGA AAATACTATC TTGCATCAAA ACGGGTGATG AACATAATGG TAATTTATTT    6480
ATGGTTGGAG ATGTTAAGCA ATCCATTTAT AAATTTAGAC AAGCTGATCC AAGTTTATTT    6540
ATTGAAAAGT ATCAACGCTT TACTATAGAT GGAGATGGCA CTGGACGTCG AATTGATTTG    6600
```

```
TCGCAAAACT CCGTTCTCGA AAAGAAGTAC TGTCAACGAC TAACTATATA TCAAACATAT    6660
GATGGATGAA CAAGTCGGTG AAGTAAAATA TGATGAAGCG GCACAGTTGT ATTATGGTGC    6720
ACCATATGAT GAATCGGACC ATCCAGTAAA CTTAAAAGTG CTTGTTGAAG CGGATCAAGA    6780
ACATAGTGAT TTAACTGGTA GTGAACAAGA AGCGCATTTT ATAGTAGAAC AAGTTAAAGA    6840
TATCTTAGAA CATCAAAAAG TTTATGTATA TGAAAACAGGA AGCTATAGAA GTGCGACATA    6900
CAAAGATATC GTTATTCTAG AACGCAGCTT TGGACAAGCT CGCAATTTAC AACAAGCCTT    6960
TAAAAATGAA GATATTCCAT TCCATGTGAA TAGTCGTGAA GGTTACTTTG AACAAACAGA    7020
AGTCCGCTTA GTATTATCAT TTTTAAGAGC GATAGATAAT CCATTACAAG ATATTTATTT    7080
AGTTGGGTTA ATGCGCTCCG TTATATATCA GTTCAAAGAA GACGAATTAG CTCAAATTAG    7140
AATATTGAGT CAAATGATGA CTACTTCTAT CAATCGATTG TAAATTACAT TAATGACGAA    7200
GCAGCAGATG CTATTTTAGT TGATAAATTA AAAATGTTTT TATCAGATAT TCAAAGTTAC    7260
CAACAATATA GTAAAGATCA TCCGGTGTAT CAGTTAATTG ATAAATTTTA TAATGATCAT    7320
TATGTTATTC AATACTTTAG TGGACTTATT GGTGGACGTG GACGACGTGC AAACCTTTAT    7380
GGTTTATTTA ATAAAGCTAT CGAGTTTGAG AATTCAAGTT TTAGAGGTTT ATATCAATTT    7440
ATTCGTTTTA TCGATGAATT GATTGAAAGA GGCAAAGATT TTGGTGAGGA AAATGTAGTT    7500
GGTCCAAACG ATAATGTTGT TAGAATGATG ACAATTCATA GTAGTAAAGG TCTAGAGTTT    7560
CCATTTGTCA TTTATTCTGG ATTGTCAAAA GATTTTAATA AACGTGATTT GAAACAACCA    7620
GTTATTTTAA ATCAGCAATT TGGTCTCGGA ATGGATTATT TTGATGTGGA TAAAGAAATG    7680
GCATTTCCAT CTTTAGCTTC GGTTGCATAT AAAGCTGTTG CCGAAAAAGA ACTTGTGTCA    7740
GAAGAAATGC GATTAGTCTA TGTAGCATTA ACAAGAGCGA AGAACAACT TTATTTAATT    7800
GGTAGAGTGA AAAATTGATA AATCGTTACT AGAACTAGAG CAATTGTCTA TTTCTGGTGA    7860
GCACATTGCT GTCAATGAAC GATTAACTTC ACCAAATCCG TTCCATCTTA TTTATAGTAT    7920
TTTATCTAAA CATCAATCTG CGTCAATTCC AGATGATTTA AAATTTGAAA AAGATATAGC    7980
ACAAGTTGAA GATAGTAGTC GTCCGAATGT AAATATTTCA ATTATATACT TGAAGATGT    8040
GTCTACAGAA ACCATTTTAG ATAATAATGA ATATCGTTCG GTTAATCAAT TAGAAACTAT    8100
GCAAAATGGT AATGAGGATG TTAAAGCACA AATTAAACAC CAACTTGATT ATCAATATCC    8160
ATATGTAAAT GATACTAAAA AGCCATCCAA AACAATCTGT TTCTGAATTG AAAAGGCAAT    8220
ATGAAAGAAG AAAGTGGCAC AAGTTACGAA CGAGTAAGAC AATATCGTAT CGGTTTTCAA    8280
CGTATGAACG ACCTAAATTT CTAAGTGAAC AAGGTAAACG AAAAAGCGAA TTGAAATTGG    8340
TACGTTAATG CATACAGTGA TGCAACATTT ACCATTCAAA AAGAACGCA TATCTGAAGT    8400
TGAGTTACAT CAGTATATCG ATGGATTAAT CGATAAACAT ATTATCGAAG CAGATGCGAA    8460
AAAAGATATC CGTATGGATG AAATAATGAC ATTATCAATA GTGAGTATAT TCGATTATTG    8520
CTGAAGCAGA GCAAGTTTAT CGTGAATTAC CGTTTGTAGT TAACCAAGCA TTAGTTGACC    8580
AATTGCCACA AGGAGACGAA GACGTCTCAA TTATTCAAGG TATGATTGAC TTAATCTTTG    8640
TTAAAGATGG TGTGCATTAT TTTGTAGACT ATAAAACCGA TGCATTTAAT CGTCGCCGTG    8700
GGATGACAGA TGAAGAAATT GGTACACAAT TAAAAAATAA ATATAAGATA CAGATGAAAT    8760
ATTATCAAAA TACGCTTCAA ACGATACTTA ATAAAGAAGT TAAAGGTTAT TTATACTTCT    8820
TCAAATTTGG TACATTGCAA CTGTAGTATT TTGATTTTCA AAAGAATAAA AAATAATTTC    8880
GATTAAGTGC AAAGTCCTTG TAGCAGAATG AACACAACTC ATTTTCAAAA TTGTCTTACT    8940
TATTTATTTG TTATTTGATA ACGAAAAAAG TTATAATGTG AATTAAGATA AAGATGAGGA    9000
```

| | | | | | |
|---|---|---|---|---|---|
|GTTGAGAATG|AATGAAATTC|TTATCATTCA|AGTATAATGA|CAAAACTTCA|TATGGCGTTA 9060|
|AAGTAAAACG|CGAAGATGCT|GTATGGGATT|TAACACAAGT|ATTTGCTGAC|TTTGCAGAAG 9120|
|GAGATTTCCA|TCCTAAAACA|TTGTTAGCTG|GTTACAACA|AAATCATACT|TTAGATTTTC 9180|
|AAGAACAAGT|ACGTAAAGCA|GTTGTAGCAG|CAGAAGATAG|CGGCAAAGCT|GAAGACTATA 9240|
|AAATTTCATT|TAATGACATT|GAATTCTTAC|CACCAGTAAC|ACCTCCGAAT|AATGTGATTG 9300|
|CTTTTGGTAG|AAATTACAAA|GATCATGCGA|ACGAATTAAA|TCATGAAGTA|GAAAAATTAT 9360|
|ATGTATTTAC|AAAAGCAGCG|TCATCTTTAA|CAGGAGATAA|TGCAACAATT|CCAAATCATA 9420|
|AAGATATTAC|TGATCAATTA|GATTATGAAG|GTGAATTAGG|TATTGTTATT|GGTAAGTCTG 9480|
|GTGAAAAGAT|TCCAAAAGCA|TTAGCTTTAG|ATTATGTTTA|CGGCTATACA|ATTATTAACG 9540|
|ATATCACTGA|TCGCAAAGCA|CAAAGTGAAC|AAGATCAAGC|ATTTTTATCA|AAAAGTTTAA 9600|
|CTGGCGGTTG|CCCAATGGGT|CCTTATATCG|TTACTAAAGA|CGAACTACCA|TTACCTGAAA 9660|
|ATGTAAATAT|TGTTACAAAA|GTTAACAATG|AAATTAGACA|AGATGGTAAC|ACTGGCGAAA 9720|
|TGATTCTTAA|AATTGATGAA|TTAATAGAAG|AAATTTCAAA|ATATGTTGCA|CTACTACCGG 9780|
|GAGATTATTA|TTGCAACTGG|TACACCAGCT|GGCGTTGGTG|CAGGTATGCA|ACCACCTAAA 9840|
|TTTTTACAAC|CAGGTGATGA|AGTTAAAGTG|ACTATTGATA|ATATTGGAAC|GCTGACAACT 9900|
|TATATCGCTA|AATAATTATC|ATTTAAAAG|CTAACCAGGT|CTTTATATAG|ATTGGTTAGT 9960|
|TTTTTCTTGC|TTTTCTAAAA|AGGTGTTAAA|GATAAATTAT|TTATAATGTT|ACCATTTGA 10020|
|GATGAAAGTG|AAATATTGAT|ATTAAGAAGT|AGTTGATTAT|TTTACAGCAG|ATTCACAATA 10080|
|TTCTAATAAG|GGCAATGCAA|ATGTCATGTT|CTTCCTCTCA|AATATAGAAG|TGTGGTAGAA 10140|
|TATATATTCG|TGTATAATCA|AATCTAGATT|AAATTACAAG|CAAGTGGGTA|TTAATCCCAA 10200|
|GAAGCTT| | | | |10207|

(2) INFORMATION FOR SEQ ID NO:3:

( i ) SEQUENCE CHARACTERISTICS:
        ( A ) LENGTH: 2082 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA- 36

( x i ) SEQUENCE DESCRIPTION: SEQ ID NO:3:

| | | | | | |
|---|---|---|---|---|---|
|AAGCTTTCTA|ATCTATCGTT|AATGATTTGC|TTTAAAATTG|GGTCGAAGTT|AATTGAAGGT 60|
|GTGAAGTGTA|TATCTGTATT|AATAACCATG|TCATTCATTT|GCTGCTTCAC|TTTGTTAACA 120|
|AGTCTTCCGT|CATATAAAAA|TAATGGTACG|ACAATCAATT|TTTGATACCG|TTTCGAGATG 180|
|CTTTCTAAAT|CATGTGTAAA|ACTAATCTCT|CCATATAGCG|TTCTCGCATA|AGTAGGTTTA 240|
|TTAATCTGCA|AATGTTGAGC|GCATATTTGT|AACTCTTCGT|GTGCCTTAGT|AAAATTTCCA 300|
|TTAATATTGC|CGTGTGCAAC|AACCATAACT|CCAACTTGTT|GTTCGTCACC|TGCTAATGCG 360|
|TCACAAATAC|GTTGTTCAAT|TAATCGTCTC|ATTAAGGAT|GTGTGCCAAG|TGGCTCGCTT 420|
|ACTTCTACCT|TTATGTCTGG|ATACCGTCGT|TTCATTTCAT|GAACGATATT|CGGTATATCC 480|
|TTGAGATAAT|GCATTGCACT|AAAGATTAGC|AATGGTACAA|TTTTAAAATG|GTCAACCCCA 540|
|CTTTGAATCA|ACGTCGTCAT|TACCGTCTCT|AAATCCTGAT|GCTCACTTTC|TAAAACGCA 600|

| | | | | | | |
|---|---|---|---|---|---|---|
| ATATCATAGT | GATGTATATC | ATCTTTTACT | AATTCAGAAA | TAAATGCTTC | TAACGCTTGA | 660 |
| TTCTGTCGTC | CGTGCCTCAT | GCCATGTGCA | ACAATGATAT | TCCCATTCAC | ATTTACCAAC | 720 |
| CCTTTCACAC | GTATTGTATA | CCAAATCATT | TTGTTTTTGT | GAAAAGAATC | ACATTATAAT | 780 |
| GTAAAATCAG | GGAATTCCCT | GATGCCTGTA | GTCATGCATA | TTCCTTATAC | ATTTTCCTT | 840 |
| TTTGTTAAAT | CAAAAAAAGC | GACCGATATA | TGAATCCCTA | CTCAACATTT | ATTTGAGCAA | 900 |
| GCATCAATAT | ATCGGTCGCT | TGTAGTGTAT | ATTATTATCT | TAAAATGGTG | GTTGGCCTAA | 960 |
| TATTGTTTCG | TCAAAGCGCT | CGGGTATCAA | TACTTTGCGC | ATGATCACAC | CTAAATCGCC | 1020 |
| ATCATCATTT | TCATGTTCGC | TGTATATTTC | ATAACCTCTT | TTTTCATAAA | TTTTAAGTAA | 1080 |
| CCACGGATGC | AATCTTGCAG | ATGTACCTAA | AGTAACTGCC | GCTGACTTTA | ACGTATCTCG | 1140 |
| CAAAATGCT | CTTCAACATA | AGTAAGTAAT | TGGCTACCAT | AGCCTTCCC | TTCATACTCA | 1200 |
| GGATTTGTCG | CAAACCACCA | GACAAAGGA | TAGCCCGAAA | TACTTTTCAC | ACTTCCCCAA | 1260 |
| GGATATCTAA | CCGTAATCGT | AGATATAATT | TCATCATCAA | TTGTCATGAC | AAATGTAGTA | 1320 |
| TTTTTATCTA | TATTTTCTTT | AACAGCATCT | AAATTAGCAT | TAACTGAAGG | CCAATCAATA | 1380 |
| CCTAGTTCTC | TTAGAGGCGT | AAATGCTTCA | TGCATGAGTT | GTTGCAATTT | TTCTGCATCT | 1440 |
| TGTTCACTTG | CGAGTCGAAT | CATCGTTTTT | GTCATATTAA | TCCCCACTCT | TTTTTAAATG | 1500 |
| ATTTAACCAT | ATTTTATTTT | TAAATAAAT | ATCCATCAAA | GTGTATCAAT | AAATTTATCA | 1560 |
| CATGTCAGAA | AGTATGCTTC | ATCTGAATAC | ACCAATACTC | TCATGAAACT | TATTAAAAAT | 1620 |
| TACTCTCTCA | ACGTAAAAAA | ACCATTCAAA | TTCATGAATG | GTTTGGAAGA | ATGATTCATT | 1680 |
| GTTACGCTAT | TTAATCACTA | CATCTTAATT | ATTGTTGCTC | TAAACGATTA | CGCTTACCAT | 1740 |
| TTAAGAAAGC | ATAAACGAGA | CCTACAAAAA | TACCGCCACC | GACAAAGTTA | CCTAAGAAAG | 1800 |
| CAAAAACGAT | ATTTTTAAA | ACATGTAACC | ATGAAACTGC | ATCAAGGTTA | AAGAATACCA | 1860 |
| TACCTGCATA | TAGACCTGCA | TTGAACACAA | CGTGCTCATA | TCCCATGTAT | ACAAAGACCA | 1920 |
| CGACACCACA | AGCTATGAAG | AATGCCTTTG | TTAAGCCGCC | TTTGAATTGC | ATAGAGATGA | 1980 |
| AAATACCAAT | ATTAATAAG | AAGTTACAGA | AAATACCTTT | TGTAAAAATA | TTCAACCATG | 2040 |
| TTGAATCAAC | AGTCTTTTTC | TGAACTAAAG | CTGTTAAAGC | TT | | 2082 |

( 2 ) INFORMATION FOR SEQ ID NO:4:

( i ) SEQUENCE CHARACTERISTICS:
        ( A ) LENGTH: 2885 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA- 77

( x i ) SEQUENCE DESCRIPTION: SEQ ID NO:4:

| | | | | | | |
|---|---|---|---|---|---|---|
| AAGCTTTTGA | TTAATTTGGG | CTTTAAAGTA | TTCCCAATTA | TAATTCTTCA | TGATTTTCTT | 60 |
| ATTGGATTTC | GAATTTGGTT | TCATGCATTG | TTGCCTCAAA | GAACATGCTG | AACAGTCATC | 120 |
| GCATTCATAT | AGCTTGAAGT | CACGTTTAAA | ACCATATCTA | TCATTACGGT | ATGCATATCT | 180 |
| TTTAAAACCT | ATTCTTTTGT | TATTAGGACA | TATAAATTCA | TCATTAAGTT | CGTCATATTT | 240 |
| CCAATTTTGA | GTGTTAAAAA | TGTCACTTTT | AAACTTTCTA | GTTTTATCTT | TAATAAACAT | 300 |
| GCCATACGTA | ATAAGTGGCG | TTTTATTAAA | ACATCTATAA | TAGCCATATA | GTTTGCTCA | 360 |
| CTATCATAAC | TGCATCAGCT | ACATTAACTC | TGGTAATACC | GAGGATTTGA | ATCATTGTTA | 420 |

```
AAAATGGAAT  TAAAGTTCTA  GTATCTGTTG  GGGTTTGAAA  TAGGTCATAG  GATAAAAAAA    480

TTGAGAATTT  GTCGCTATTT  GTAAATTGTA  TCCTGGCTTA  AGTTGGCCAT  TTTTCATATG    540

GTCTTCCTTC  ATTCTCATAA  AAGTTGCATC  ATGATCAGCC  CAGAAAGCTA  TTTCTATCTT    600

TAAGAATCCA  TTTTTGTTCT  TCATATTTAT  TTTTTCTTTC  GGAATAATCA  TCAAATTTCT    660

TTTTGAACTT  CTTAATCTCA  GTTCTTTTTT  ACGGGTCTGT  TTTCTAATTT  GAGCACTCTT    720

CGTTCTAAAT  AGAATGATTT  AAATCTTCGA  TTTCTTTTAT  CTAAATGACT  ACCAATTAAA    780

TCTATTTCTT  CTCGTGATTT  TGAATACTTT  TCTTCCACAC  AAATGTATAT  CTATTGGCAT    840

TAGCTTCTAC  TTATGTACCA  TCAATAAAAA  TTGAATTATT  ATCAATAAGA  TTTTGCTTTA    900

AACATTGACT  ATGGAACTGA  ATAAATAAAG  ATTCAATTAA  CGCATCAGTA  TTAGGATTCA    960

CTCTAAAACG  ATTAATAGTT  TTATAAGAAG  GTGTTTGATC  TTGAGCTAAC  CACATCATTC   1020

GAATACTGTC  ATGAAGTAAT  TTCTCTATTC  TACGACCAGA  AAATACAGAT  TGAGTATATG   1080

CATATAAGAT  GATTTTTAAC  ATCATTTTTG  GATGATAGGA  TGTTGCGCCA  CGATGATGTC   1140

TGAATTCATC  GAATTCGCTA  TCAGGTATCG  TTTCAACAAT  TTCATTTACA  TATCGCGAAA   1200

TATCATTTTA  AGGAATTCTA  ACAGAAGTTT  CTATTGGTAG  TGTAAGTTGG  GCAAAGTGTC   1260

TTATTTTTTT  AAAGTATGTA  AAAGTAAAAT  TACATGTTAA  TACGTAGTAT  TAATGGCGAG   1320

ACTCCTGAGG  GAGCAGTGCC  AGTCGAAGAC  CGAGGCTGAG  ACGGCACCCT  AGGAAAGCGA   1380

AGCATTCAAT  ACGAAGTATT  GTATAAATAG  AGAACAGCAG  TAAGATATTT  CTAATTGAA    1440

AATTATCTTA  CTGCTGTTTT  TTTAGGGATT  TATGTCCCAG  CCTGTTTTAT  TTTCGACTAG   1500

TTTGGAGAAT  TTATTGACAT  TCACATTATT  TAAACGGCAA  CAAAGATTGT  TTTATTTTGA   1560

TAGGCATTAT  ATGGTGTTAA  AAAATTTGCA  TGAAAATTAA  AAAATGCTTC  GTTCAGGAAG   1620

GTGTCGTAAT  TTACCTATTT  GCTGAATGAA  GCATTTTATT  TTTAAATATG  ATAGCCAATA   1680

TAACAAGCTA  TAAATCCAAT  GATGAATTGT  AAAAGTGAAT  AATTGAGAAA  AAGGTTAATA   1740

TCAAATTTTG  GTGTCATCAT  TAATGTAAGT  TCCTTGGCTA  ACGTTGAGAA  AGTTGTTAAG   1800

CCACCTAAAA  AAACCGGTGA  CAAAGAACGC  AGGGAACCAT  GAGATTGAAA  TTGATAGGCC   1860

TATAGTTAAT  CCAATTAAAA  AACTACCAAC  TAGATTTACT  ATCAATGTTG  CGATAGGTAA   1920

CTTTGAAGTA  AATTTATGAT  TAAAATAATC  AGTAATGGCA  CTTCTAGCAA  TTGCGCCAAA   1980

ACCGCCGCCA  ATCATGACTA  AAATGATTGA  TATCATGATA  AACCACCACC  TAGTTTTATA   2040

CCGACGTAAC  ATAACAAAAT  ACCAAAGACA  TAACTTGTTA  CAGCATATAG  TAGTAAAGTT   2100

ATAAATTGTT  GATGATCAAA  CATATGTATT  AATTCTAATT  GAAATGTTGA  AAAAGTCGTT   2160

AAAGCACCAA  GAAAACCAGT  CGTAATAGCT  TTTTTAGGG   TCGGATGGTT  TGAAAAAAAT   2220

GCAATTGTTA  AGGCTGTTAG  CAATCCCATT  ACAAAGGCAC  CAGTCAAATT  GGCTATCAGT   2280

GTTCCGATTG  GAAAACCTCC  GTCAGTATTC  AGAAAGAAA   TGAGGTAACG  TAATAAAGCG   2340

CCTAAAGCAC  CACCGATAAA  AATATATACA  TATTGCATTT  GGTTCACCTC  GAAAAGAAGT   2400

AGTTTGAATT  TAAAAAGAG   GTTTTGGCAA  CACGACGACA  AAAATTGTCG  ATGCATTATC   2460

AAACCTCATT  ATATGTTATA  TCTTGTTGTA  TAACTATAGC  GATTAGATGC  ATAGTTATGA   2520

TTTCGAAAAT  CTAATATTTT  TTATACGCAA  CAACGTCATC  AAATTGTTTT  ACTCATTATA   2580

GCATGATACA  TTGTATTGTT  TTGTATTAAC  GCTACATTGA  CATTTTATCT  TTTTTAAATA   2640

AAACCGAATG  TACGACAATT  GAAAAGATAT  GTACTAAAAT  AACAATTAGA  ATAATCCAAG   2700

GCAAACTTTT  ACTCGCAATT  CTAATCCAAT  CTGCATCAGG  CTTTAGTGAT  TTAATTGAAC   2760

GATCTGCAAA  AATTATAGAC  AAAATTAGTA  CAATTGAGTT  AATAACACTG  CAGAAAAGTA   2820
```

| | | | | | |
|---|---|---|---|---|---|
| TTAATTTAAT | AAAAGAATTA | AAAAATCCAC | TTAGGAAAAC | GTTATTTGTA | TTAAAGAAAA | 2880
| AGCTT | | | | | 2885

( 2 ) INFORMATION FOR SEQ ID NO:5:

( i ) SEQUENCE CHARACTERISTICS:
        ( A ) LENGTH: 2362 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 3

( x i ) SEQUENCE DESCRIPTION: SEQ ID NO:5:

| | | | | | |
|---|---|---|---|---|---|
| AAGCTTCACA | ACTTGAAAAT | ATAGCACAAA | CATTAAAGGA | TTTAGGTAGA | AAACGAGCAA | 60
| TTTTAATTCA | TGGTGCAAAT | GGGATGGATG | AGGCCACGCT | TTCTGGTGAA | AATATCATTT | 120
| ATGAAGTTAG | CAGCGAAAGA | GCATTAAAAA | AATATAGTTT | AAAAGCAGAA | GAAGTCGGTT | 180
| TAGCTTATGC | AAATAATGAC | ACGTTGATAG | GTGGTTCACC | TCAAACAAAT | AAACAAATTG | 240
| CATTGAATAT | CCTAAGTGGC | ACGGATCACT | CAAGTAAACG | AGATGTAGTT | TTGTTAAATG | 300
| CTGGAATTGC | TTTATATGTT | GCTGAGCAAG | TGGAAAGTAT | CAAACATGGC | GTAGAGAGAG | 360
| CGAAATATCT | CATTGATACA | GGTATGGCAA | TGAAACAATA | TTTAAAAATG | GGAGGTTAAG | 420
| TAATGACTAT | TTTAAATGAA | ATTATTGAGT | ATAAAAAAC | TTTGCTTGAG | CGTAAATACT | 480
| ATGATAAAAA | ACTTGAAATT | TTACAAGATA | ACGGAAATGT | TAAGAGGAGA | AAGCTGATTG | 540
| ATTCACTTTA | ACTATGATAG | AACATTATCA | GTTATTGCTG | AAATAAAATC | GAAAAGCCCA | 600
| TCTGTACCTC | AATTACCGCA | ACGTGATCTT | GTTCAACAAG | TTAAAGATTA | TCAAAATAT | 660
| GGTGCTAATG | CTATTTCAAT | ATTAACTGAT | GAAAAATACT | TTGGCGGTAG | TTTTGAACGA | 720
| TTAAATCAGT | TATCAAAGAT | AACATCGTTA | CCAGTTTTAT | GTAAAGATTT | TATTATTGAT | 780
| AAAATTCAAA | TAGATGTTGC | AAAACGAGCT | GGTGCATCTA | TTATTTATT | AATAGTAAAT | 840
| ATTTTAAGTG | ATGACCAATT | AAAAGAATTG | TATTCATATG | CAACAAACCA | TAATTTAGAA | 900
| GCTCTAGTAG | AAGTTCATAC | AATTAGAGAA | CTTGAACGTG | CACACCAAAT | TAACCCTAAA | 960
| ATTATTGGTG | TTAATAATCG | TGATTTAAAA | CGATTTGAAA | CCGATGTTCT | ACATACAAAT | 1020
| AAATTACTTA | AGTTAAAAA | GTCTAATTGC | TGCTACATTT | CAGAGAGTGG | CATTCATACA | 1080
| AAAGAAGATG | TTGAGAAAAT | AGTAGATTCA | AGTATTGACG | GTTTACTTGT | AGGGGAGGCA | 1140
| TTAATGAAAA | CAAATGACTT | AAGTCAGTTT | TTTGCCTAGT | TTAAAGTTAA | AGAAGAATCT | 1200
| CTATGATAGT | TAAATTTTGT | GGTTTTAAAA | CCGAAAGTGA | TATTAAGAAA | ATTAAAAAAT | 1260
| TAGAAGTTGA | TGCAGTAGGG | TTTATACATT | ATCCCGATAG | TAAGAGACAT | GTCTCACTGA | 1320
| AACAATTAAA | ATATTTGGCT | AAAATAGTGC | CAGATCATAT | AGAGAAAGTA | GTGTCGTAGT | 1380
| AAATCCTCAA | ATGTCCACCA | TAAAGAGAAT | AATTAATCAA | ACTGATATTA | ACACAATCCA | 1440
| ATTACATGGA | AATGAAAGCA | TTCAATTAAT | TAGAAATATT | AAGAAACTTA | ATTCAAAAAT | 1500
| AAGAATCATA | AAAGCAATTC | CAGCAACAAG | AAATTTAAAT | AATAACATTC | AAAAGTATAA | 1560
| AGATGAGATA | GACTATGTTT | ATTATAGATA | CACCATCAAT | CACATACGGA | GGGACAGGTC | 1620
| AAAGTTTTGA | CTGGAAATTA | TTAAAAAAAA | TAAGGCGTT | GATTTTCTCA | TTGCGGTGGT | 1680
| TTGGATTTTG | AAAAGATAAA | ACGATTAGAA | ATATATTCAT | TTGGACAATG | TGGTTATGAC | 1740

```
ATCTCAACTG GCATTGAGTC ACATAATGAA AAAGATTTTA ATAAGATGAC TCGAATATTA   1800

AAATTTTTGA AAGGAGACGA ATGATTAATG AAAATTCAAA CAGAAGTAGA TGAATTGGGC   1860

TTTTTCGGTG AATATGGTGG CCAATATGTA CCTGAAACAT TGATGCCAGC TATTATTGAA   1920

CTTAAAAAAG CATATGAGGA CGCGAAATCA GATACTCACT TCAAGAAAGA ATTTAATTAT   1980

TATTTAAGTG AATATGTTGG TAGAGAAACG CCTTTAACAT TTGCTGAATC ATACACAAAA   2040

TTGTTAGGTG GTGCCAAAAT ATATCTTAAA AGAGAAGACT TAAATCACAC TGGTGCTCAT   2100

AAAATTAATA ACGCGATAGG ACAGGCACTA TTAGCTAAAA GGATGGGGAA AACTAAATTA   2160

GTAGCCGAAA CAGGTGCTGG TCAACATGGT GTAGCAAGTG CCACCATCGC TGCTTTATTC   2220

GATATGGATC TTATTGTTTT CATGGGAAGT GAAGATATCA AACGTCAACA ACTTAACGTA   2280

TTTAGAATGG AATTGCTAGG AGCTAAAGTA GTGTCTGTGT CAGATGGGCA AGGAACACTA   2340

TCAGATGCTG TAAATAAAGC TT                                           2362
```

( 2 ) INFORMATION FOR SEQ ID NO:6:

( i ) SEQUENCE CHARACTERISTICS:
        ( A ) LENGTH: 8654 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 22

( x i ) SEQUENCE DESCRIPTION: SEQ ID NO:6:

```
AAGCTTGTTT TATTGCTTAG TTATATTTCC AATAACACTC ATTTTATATG TACGTATTGC     60

CAAAAAAAT TATCTATACA GTAATAAGTA TGAAATGAGA ACTGGAATAA TCATTGGTAT    120

TATTGCTTTA ATTCTAGTAA TTATGCAAGG GTTTCACTTT AACTGGGCTA TTATTCCTAT    180

TTCTATCTAT GGTCATCAGT TTGTATTTTT CGCTGGAATT ATTTAAGTC TTGTTGGTAT     240

ATTCTTTAAA CGTATAGAAT TTGTAGGAGT TGGCTTACTA TTTTGTCAAA AACATAGATG    300

CAATGGTAAC TGACCCGGAA ATTGCACAGT TTTTCTCTTT AGCAATTTGG ATTATACTTG    360

TTGTGCTAAT CATTTTTTAT ACGATACGTT TATCTGAACG CACTAAATCA TCATCATATA    420

CAAAGATTTA AACTCAGAAA ATATGCTAGA CATATCTTTC TGAGTTTTTT AATTTATTAA    480

AATATATCAT TTGTTTACCA TATAAGTTTG TTTAGAAAA TGAATCACTA TTTTAATATA     540

CAAATAATTT AATTACACTG AAAATAACCT AAAAGCGTAA CACTATTTTA ATATGGGTAT    600

ATAAATGACT AAAGGGAGGT GCCAAGATGA ATAAAATTCA AATTTGTAAT CAGATTGAAC    660

TTAACTATAT TGATGAAGGC GAAGGCATCC CCATCATTTT AATTCATGGA TTAGATGGAA    720

ACTTGGCAGG ATTTAAAGAT TTAAAAAATG AACTCAAGAA GCAGTATAGA GTAATTACTT    780

ATGATGTCAG AGGTCATGGA AAATCTTCAC GAACAGAATC ATATGAATTA AAAGATCATG    840

TTGAAGATTT AAATGATTTA ATGGGAGCAT TAAATATCGA TTCTGCACAT ATTTTAGGAC    900

ATGATATGGG GGGCATCATT GCGAGTGAAT TTACTGAAAA ATATCAATAT AAAGTGATTA    960

CATTGACAAT TGTTTCGGCC AAAAGTGAAG ACATTGCAAA TGGTTTCAAC AAATTAATGG   1020

TTGATTACCA AGAAGAATTA GCAGGCTTTA ATAAATCTGA GGCAATGATT ATTTTATTCT   1080

CTAAATTATT TAAAGAGAAA GATAAAGCAA TGAAATGGGT ATCAAAGCCA AAAATTATAC   1140

AATAGACCAA CTCCGGAAGA AAGTGCAATT GCAGTACGTG CATTGCTTAA TATTAAAGAT   1200

TTAACTCGTG TTCATCATAA TGTGTCCATA CCTACTTTAA TTGTGAATGG TAAGTATGAC   1260
```

| | | | | | | |
|---|---|---|---|---|---|---|
| CCACTCATAC | AAAATAAAAG | TCATTATGAT | ATGGATCAAT | ATTATGATCA | AGTTACAAAA | 1320 |
| ATTGTATTTG | ATAATTCAGG | ACATGCACCA | CATATCGAGG | AACCAGAAAA | ATTCCTGAAA | 1380 |
| CTCTACTTAG | ATTTTGTTAG | TTAAAAAATA | AGAACATAAA | TAAAACCCT | TAAATGATTA | 1440 |
| TTGTCGGAAA | ATCATTTGAG | GGTTTTGTAG | TAGCAGTAAA | GTTTGGACTC | AGATCACTAT | 1500 |
| CGTATTAACT | TAATAAAAGA | GTAAACAGT | CTTATCTTTC | ATAAGTGAAA | GAAATATCTG | 1560 |
| TTTNACTCCC | TAGCCATTAT | ACTTCATTTC | ATTATTTGCT | TCTGTGATAC | GGTTGTTTAC | 1620 |
| TCGTTTAAGT | AAATCATCGA | TTTTTTTACG | CTGCTTAGAA | TCTACTAAGA | TTAAAACAGT | 1680 |
| TCTTTCATCG | TGTTCATTAC | GTTTTTTATT | AAAGTAATTT | TCTTGAGATA | AATTTTTAAC | 1740 |
| AGCTTTAACA | ACTTGAGGTT | GTTATAATT | TAAGTGATTG | ATAATATCTT | TAAGATAATA | 1800 |
| TTCCTCTTCT | TTATTCTCAC | TAATATAAGT | TAATACTGCA | AATTCTTCAA | AGCTGATTGA | 1860 |
| GAATTCTTTT | TTAATTATTC | CTTTTAATCT | GTCAGCATAA | GTGACCATAG | CTAATAATTC | 1920 |
| AAAGCAGTCA | TTGATTTTTG | AAATAGCCAT | TAATGAAACC | TCCCTATTTA | TATCATATCC | 1980 |
| ATAAATCTTA | AAACCCATCT | TTTTAAATTT | AAAGATAGTT | AATTATATTA | TTGAATTAAG | 2040 |
| ATTACTTGGA | TACTATACCC | TAATTTATTA | ATTTATATCT | ATTTTTCTTA | TGAAAATACG | 2100 |
| AAAGTGTCCG | TCATAATATA | GTATTAATTT | AAATTTAAAG | AATATATTTA | ATGCTATATT | 2160 |
| ATTAGTTAA | TTATAACTAA | ATAAAATTAA | GAAGTAAACA | AATAAGTGTT | TATAAACAA | 2220 |
| ATTATCTTTT | AAAGTTTATA | CTTGAATTAG | CAATGTAGCA | TTTGCTATAT | TCAAAAAAT | 2280 |
| AAGATTGTTT | CTAATTTTCC | TTAATTTAAT | AAAAATTATA | CTAAAAGAA | TACTTTTTGG | 2340 |
| AAAGAATTTT | ACTAACATTT | TTATATATA | AATGTTTATT | AATTTAGAAG | TAGGATTTTT | 2400 |
| AACAACTTTT | TCATCTATCA | ATAAGCCTTT | AGTTATATTA | ATATACCCAC | TTTTTAAACT | 2460 |
| CTTTTTGTAT | GTTACTTCTC | TTTTTGTAGA | ATTAAAACAT | AGCGTTTTG | AACAATAGCT | 2520 |
| GACGTAGGTA | ACTCTATGTC | ATTTGAGGCT | AATTTGATTT | TAAAGTGTGT | TCCAATTTGA | 2580 |
| TGATTGGGTT | GTGTAGAAAG | TAAAATGTCG | TAATATGAGA | CGCCATTTTT | TATTTTTGAT | 2640 |
| GGTATATTCG | AAATTTCTTT | AATTTTACTA | GTAAATTGAG | TGTTGTCACT | AGATGTTACA | 2700 |
| GAAATATTTT | GATTTATTTT | TAATAAATTC | AACTCAGATT | CTGATATATT | AGCACGAATA | 2760 |
| ATACGTTCGT | TGCTATTAAT | TTGCACTATC | TTTTCGTTTG | GTTTGAAGG | GATAGAATTA | 2820 |
| ATATATGAAA | TACTTCCATT | AATTGGTGAA | AATAAAGTGG | ATTTAATTGA | GGATTTAGTT | 2880 |
| TGAATCATTT | GTAATTTTAG | CTGATTAAGG | AATGAATAAT | AATGTAAATC | ATTTTTAGAA | 2940 |
| TTTAAAGTTT | TGTTGTTACG | TTCATTACTA | AGTGTATTTT | GGAGTTCCTC | ATATAAATGA | 3000 |
| TCTTTTTCAT | AATTGTAATA | TTCTAACACT | GGAGTGTTTT | TAGATACTTT | GCTATGATTT | 3060 |
| TTTACTAAAA | GTTTTTGGAG | TTGTCCTAAA | GTGGGAGTGT | AGTAGAAAAT | ATAGCTGTTA | 3120 |
| AGAGGGCTT | GTATACCAGT | TGTTGAAAGG | AGTAATTTGG | GCTTTGCTTT | TATAGTTTTT | 3180 |
| ATATTTTAA | TATCTTCTGT | TTTAGAAGTT | AATTTAGAGA | AAGTAATGTA | ACTAAAACTA | 3240 |
| CAAGTTGTGA | GAATGAAAAT | GAATAGTAAT | GAAGAAATAA | CGATGCGTTG | CTTGGTCATG | 3300 |
| GATGTTCACC | TCATAATATT | ATTGTGAGGT | TATTATACAC | TATTATTTTA | AATGAAATAT | 3360 |
| ATTAATTTTA | AATAAGCATT | ACTTTGGTT | TGTATATTGT | TTTATTTCAA | AAAATAAAGT | 3420 |
| AAATCAATTT | AATAAATTGA | AAAATAGAAG | GCTATCTTTA | ATTTTAAAAT | ATATGATTCT | 3480 |
| ACATAAATGT | TACTATAAGA | AGAATCACTC | ATAAAAACTG | CCAACAAAGA | CAAAATCTTT | 3540 |
| GTTGGCAGTT | CGAAATAGAC | ATTTATTTGT | ATGAGGAATC | TACATTAATA | TAAGCGGATA | 3600 |
| ATTTTTATTC | AGAATAAGGA | ATTTAAAATA | ATCGTAATAA | AATAATACCT | ATAGCTATAC | 3660 |

```
ATAATAATCC ACCTAACTTA CGTGATGTTA TTTTGTTTTT AGGTGAACCC AACAAACCGA    3720
AATGATCGAT AATAATACCC ATAATCATTT GGCCCATCAT AGCAATTATA GTAGTTAAAG    3780
CTGCTCCTAA GAAAGGCATT AAAATAATAT TAGATGTTAC GAATGCCATT CCTAGTATCC    3840
CTCCAATAAA ATAAATAGAT TTAATCTTAC CTAGTGTTTT ATGAGTAGAT GATATTTTCA    3900
GACTACGATT AAATACTAAT GTTAATATAA ATAACGCTAT TGTACCAACG CTAAATGATA    3960
TGAGTGAAGC AAATATGGAT GAGTGTGTGT GTTGAGCCAG TGTGCTGTTG ATTGTTGTTT    4020
GGATTGGCGG ACGAAACCAA ATACGAATCC AATAAGCAAC CAGAATACTA TTGGTGTATT    4080
CTTATGTCTA TTAACAGGAT GTCTACGAAC ATAATTCATA AATATAATTC CAGTAATTAA    4140
AAATATAATT CCAACACCTT TAAATAATGT AAAAGATTGT TGATGGGCGC CCAATAATCC    4200
AAATGTATCA ATGATTACAC CCATAATAAT TTGCCCTGTA ACCGTAATAA CAACAGTAAG    4260
TGCTGCGCCT AATCTTGGTA ATAATAATAA GTTCCAGTT AAATAGATAA CACCTAATAG     4320
TCCTCCTAGG ACCCAAGTAT AGTTAAGTGT TTGCTTAGAA AAGAATTCTG GTGTTAATAC    4380
TTGTGGATGA ATAATGATAT TAAGCACAAG TAAGCATATT GTTCCGACAG CAAAAGATAT    4440
GGTTGAAGCA TAAAAGATG AACGGGTAAA TTGGCTTAGC CTTGAGTTGA TTGAAGTTTG     4500
AATAGGAAGT AACATGCCAA CAAAAATTCC TAAAAGATAT AGAAAAAACA ATGATAAAAA    4560
CCAACTTTCT CAATTTAATA TGATTATCAT ACCATTCATA ATCATGTTTC TAAAATGATT    4620
GAGCCATAAG CAAAGTATAG AAATAAGTTG TGAATGTTCC GAGGTGTCAT ACAGCCGATA    4680
CTATTTGAT GAATCATTAT AATAAATGC ACATTAAACA AGTTTTAGAA TTAAAAAAG       4740
CGAGACATCA TTTTGAATTT GATATCTCAC TTCATATTAA TAAAGAACA ATGTAAATTA     4800
AGTTCTTTTT TAGACTTGAA CAATTTAAA AAATTTGTTC TTCGATAAGT CTTTTTTATG     4860
ATTTTAGTAC TTTAAATAAA GCGTCAAAAA TAATGTTTTA TGAATTAATT TTTATCTTCA    4920
AATATAACAG TTGTCCTTTT ATCAATAAGT TGTGCAGCAT AAATTTGAC AGGCTTTCCC     4980
AAACTAAATC TTAAAATGTC TAATTCTAAA ATGTCTAATT CTAAAAGTTG GTTCATACTT    5040
TCTTTAATTA ATTGTTCTGT AGTAATAGCG TTAAAATCGG GTAATAGTAA TTTGACGGGT    5100
TTATTAAGAT TTGATTTAAA TACGAGTTCC AAAGTTTTG ACATACTGAT GTATCCTCCT     5160
TAAATTAAAG ATTCTGTTTT AACGATCTCG ACTTTGTCAT ACTCTTCGCC ACTGAACGTT    5220
CAATGATGGA ACGAAAAGAT TTGATTTGAT CATTAGAAAC AAGCGGATTA ATGTTAGAAA    5280
AACGACGCTT ATGTTCGACT ACTTTACCTT CAGAATTATG TTTGATTTGA GTAAAGATAA    5340
TCGTCACTTG ATTGACTTCA TTCATAATAA AACCTCCTTT CACTATATAT ATCGAAATAG    5400
ATTGAAAAAA AAGGACACAT TTTTTGAAAA ATATAGGCAA ATGCCTTTGA TGTGATACAA    5460
ACGTCATTTA TCATTAATTA TGAAACCTGT TTTAGAAGGT ATATGAGGTA AGTAGAATTG    5520
TTAAGTTGTA AAAGAAAAA TTGGAACCTG ATATTTAAAA TAACCAACTT AAAAGATTGA     5580
TCAGTGTCTA AAATTACTAT TTATATATGA ATTAAAATAT TAAGATCTCC CAATATGAGA    5640
ATGAATTAGT TTAAGTTTAT CGATGATTGA AAAATTATAG CCTCATGGAT TCTATCTTAT    5700
ATAAAATAAA GTTCTATTCC CTTTTGGATA TAAATAAGAA TAGTTACCTT TTTGTGATAT    5760
GCCAATTCAG AAAAAAAGCG ACAGTGCTTG AATCTATGTA TGCTCAATAA ACTCATTCAA    5820
ATCAACTAGC AATATCAAAT CATAAATCGT GTTGCACCAT AATAAGGATT AAAACCTGTT    5880
AGTTAACTA ATTTAAGAAA AACATTTGAT TATCTTCTCT TTCAATCGGG AATATTAATT     5940
TCTATCATTC AACAATATTT TGGATATCAG ATAACTTAAG AAATATTGAG ATTTATTGAA    6000
ATACGATATG TTTCAAATCG CCATACAATG ATTACACTTA ATAAATGATT ACACTTAATA    6060
```

| | | | | | |
|---|---|---|---|---|---|
| TAAATGTAAA | AAGAAAAGGA | GGGGTTAAAT | GAGTTTAGTA | TATCTTATGG | CGACTAATTT | 6120
| ATTAGTCATG | CTCATAGTTT | TATTCACTCT | GAGTCATCGT | CAACTAAGAA | AGGTTGCGGG | 6180
| CTATGTTGCA | TTAATAGCTC | CTATTGTGAC | ATCTACATAT | TTTATTATGA | AAATACCAGA | 6240
| TGTGATTCGA | AATAAGTTTA | TTGCTGTTCG | ATTACCATGG | ATGCCTTCAA | TTGATATTAA | 6300
| TTTAGATTTA | AGATTAGATG | GTTTAAGTTT | AATGTTCGGC | TTAATTATTT | CGCTAATAGG | 6360
| TGTGGGTGTA | TTTTTTTATG | CTACGCAATA | TTTATCCCAC | AGTACGGACA | ATCTTCCTAG | 6420
| ATTTTTCATC | TATTTACTAT | TATTTATGTT | CAGTATGATT | GGCATTGTAA | TAGCTAATAA | 6480
| TACCATCTTA | ATGTATGTAT | TTTGGGAACT | CACAAGTATT | TCCTCATTCT | TGCTTATATC | 6540
| CTATTGGTAC | AATAATGGTG | AAAGTCAATT | AGGCGCCATT | CAATCTTTCA | TGATTACAGT | 6600
| GTTTGGTGGG | CTAGCGTTAT | TAACAGGATT | TATCATTTTA | TATATCATTA | CAGGAACAAA | 6660
| CACAATTACT | GATATCTTAA | TCAACGCAAT | GCAATTTCAC | GACATCCTTT | ATTTATACCA | 6720
| ATGATTTTGA | TGCTATTATT | AGGTGCTTTT | ACCAAATCTG | CACAATTTCC | GTTTCATATT | 6780
| TGGTTACCAA | AGGCCATGGC | AGCACCTACA | CCAGTAAGTG | CTTATCTTCA | TTCGGCAACA | 6840
| ATGGTAAAGG | CTGGAATCTT | TTTACTATTT | AGATTACAC | CTTTATTGGG | ACTTAGTAAT | 6900
| GTTTATATTT | ATACAGTGAC | ATTTGTTGGT | CTAATAACTA | TGTTATTTGG | ATCTTTAACT | 6960
| GCTTTACGAC | AATACGACTT | AAAAGGTATA | CTCGCTTATT | CTACAATAAG | TCAATTAGGT | 7020
| ATGATTATGA | CAATGGTAGG | TCTAGGTGGC | GGTTATGCTC | AGCACACATC | AGATGAATTG | 7080
| TCTAAGTTTT | ATATTTTAGT | TTTATTTGCT | GGCTTATTCC | ATTAATGAA | TCATGCGGTT | 7140
| TTTAAATGTG | CATTATTTAT | GGGCGTTGGT | ATCATTGATC | ACGAGTCCGG | AACACGTGAT | 7200
| ATTCGTTTGC | TAAATGGTAT | GCGTAAAGTC | TCCCCTAAAA | TGCATATTGT | CATGTTGCTC | 7260
| GCTGCATTAT | CTATGGCAGG | TGTTCCTTTT | TTAAATGGCT | TTTTAAGTAA | GGAAATGTTT | 7320
| TTAGATTCGT | TAACTAAAGC | AAACGAACTT | GATCAATATG | GCTTCGTATT | AACGTTTGTG | 7380
| ATTATTTCAA | TAGGTGTCAT | CGCGAGTATA | TTGACTTTTA | CTTATGCACT | TACATGATA | 7440
| AAAGAAACAT | TCTGGGGAAA | TTACAATATA | GAAAAATTTA | AACGTAAACA | AATACATGAA | 7500
| CCATGGCTAT | TTAGTTTACC | AGCTGTGATT | TTAATGTTAC | TCATTCCAGT | TATCTTCTTT | 7560
| GTTCCAAACG | TTTTTGGCAA | CTTTGTTATT | TTGCCCGCAA | CCAGATCTGT | ATCTGGGATA | 7620
| GGGCGGAGGT | TGATGCATTT | GTGCCACATA | TTTCTCAGTG | GCATGGTGTG | AATCTCCATT | 7680
| AATTTTAAGA | TAGTGTATAT | ATTGGACTAT | TTTAGCTCTA | GTGTGATTGG | AAAGAGGTTA | 7740
| CGCATCAAAT | AATCAAAAGT | GCTCGATTAC | AGTGGCTATC | GGAAATTTAT | AGAGAATTTG | 7800
| AATTATACTC | AGCCCGTGGT | ATACGTGCAT | TGATGAATAA | TAAATTGAAT | TATTACATCA | 7860
| TGATTACATT | ATTTATTTTT | GTAGCTATTG | TAGTTATGGA | TATTTGACTG | TGGGTTTTCC | 7920
| TCATGTACTC | AGCTTCATAT | TAGTTCTTTC | GGACCGTTGG | AAGTTATCTT | ATCAGTTGTA | 7980
| ACATTGATTA | TCGGCATTTC | ATTAATCTTT | ATTCGTCAAC | GACTAACGAT | GGTGGTATTG | 8040
| AATGGAATGA | TTGGATTCGC | AGTTACATTA | TATTTTATTG | CAATGAAAGC | TCCAGATTTA | 8100
| GCTTTAACAC | AGTTAGTTGT | TGAAACTATT | ACGACAATCT | TATTTATTGT | TAGTTTTTCG | 8160
| AGACTACCTA | ACATCCCTCG | AGTTAAGGCA | AATTTAAAAA | AAGAGACCTT | CAAAATCATT | 8220
| GTGTCACTTG | TTATGGCATT | GACGGTGGTA | TCACTTATTT | TTGTTGCTCA | ACAAGCAGAT | 8280
| GGTATGCCTT | CAATTGCTAA | ATTTTATGAA | GATGCATATG | AACTTACAGG | TGGAAAAAAT | 8340
| ATTGTCAATG | CTATACTAGG | TGACTTCAGA | GCTTTAGATA | CTATGTTTGA | AGGACTAGTG | 8400
| TTAATCATAG | CTGGATTAGG | TATTTATACG | TTACTTAATT | ACAAAGATAG | GAGGGGGCAA | 8460

-continued

| | | | | | |
|---|---|---|---|---|---|
| GATGAAAGAG | AATGATGTAG | TACTTAAATC | AGTTACAAAA | ATTGTAGTGT | TTATTTTGTT | 8520
| AACATTTGGA | TTTTATGTAT | TTTTTGCTGG | CCATAATAAT | CCAGGTGGTG | GCTTTATTGG | 8580
| TGGCTTGATT | TTTAGCTCGG | CATTTATCTT | AATGTTTCTT | GCCTTTGATG | TAAATGAAGT | 8640
| GTTGAAAAAA | GCTT | | | | | 8654

( 2 ) INFORMATION FOR SEQ ID NO:7:

( i ) SEQUENCE CHARACTERISTICS:
        ( A ) LENGTH: 5024 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 32

( x i ) SEQUENCE DESCRIPTION: SEQ ID NO:7:

| | | | | | |
|---|---|---|---|---|---|
| AAGCTTTTTG | ATTTTTAAAG | AAAAAATTAA | ACAAGGGGC | ATTGCTTATG | GTCAATAGAA | 60
| GAAAGATATC | AATTATTGGC | GCGGGACATA | CAGGTGGGAC | TCTAGCATTC | ATTCTTGCAC | 120
| AAAAGGAATT | AGGAGATATT | GTGTTGATTG | AACGCCAGCA | ATCAGAGGGT | ATGGCTAAAG | 180
| GAAAGGCGTT | AGATATTTTA | GAAAGCGGAC | CCATTGGGG | GTTTGACACA | TCTGTACATG | 240
| GTTCAGTAAA | TATAGAAGAT | ATTAAAGATT | CAGACATAGT | GGTGATGACT | GCAGGTATAC | 300
| CTAGGAAATC | AGGAATGACA | AGGAGAAGAA | TTAGTTCAAA | CTAATGAACA | AATAGTACGA | 360
| GAAACTGCAT | TACAAATTGC | AACGTATGCA | CCTCATTCAA | TAATTATTGT | ATTGACTAAT | 420
| CCGGTTGATG | TTATGACATA | TACTGCATTT | AAAGCATCAG | GTTTTCCTAA | AGAACGTATT | 480
| ATTGGTCAAT | CTGGAATTTT | AGACGCTGCA | AGATATCGAA | CTTTTATTGC | TCAAGAACTT | 540
| AACGTGTCTG | TCAAAGATGT | AAATGGGTTT | GTTTTAGGTG | ACATGGTGA | TACGATGTTA | 600
| CCTTTGATTA | ATAACACACA | CATTAATGGG | ATTCCAGTTA | AGCATCTTAT | TTCTGAAGAA | 660
| AAGATTGATC | AAATTGTTGA | ACGTACACGT | AAGGGTGGTG | CAGAAATTGT | TGCATTACTA | 720
| GGTCAAGGCT | CAGCATATTA | TGCACCAGCA | ACTGCTATAT | ATGAAACTAT | AGATGCAATT | 780
| TTTAATGATC | GGAAACGGTT | ATTACCAAGT | ATTGCTTATC | TAGAGGGAGA | ATACGGTTGT | 840
| TCAGATATTT | GTTTCGGAGT | TCCTACTATA | ATAGGATATC | AAGGAATAGA | AAAGATTATA | 900
| GAGGTAGATA | TGAATAATGA | TGAGTATCAA | CAACTACAAC | ACTCTGCGCA | AGATGTGAGT | 960
| GAAGTCAAAA | ACTCACTAAA | ATTCAAATAA | ATAATTATGA | AGTTCTACAT | CTTAAATTGT | 1020
| TAGATTTTTG | TGAAAATTGT | GTAAAGGGTA | TTTTTTCGTT | GATTTATAAA | AGCGCTTTCT | 1080
| TGATATAATG | AACATATATT | CATAGAATAA | GGAGACGATT | AAAATGGCTA | AAGGGGACCA | 1140
| ATATCAAGCT | CATACTGAAA | AATATCATGA | GTAAAAGTC | TAAAAAAGT | TATAAACCTG | 1200
| TGTGGATTAT | CATTAGTTTT | ATTATTTAA | TTACAATCTT | GTTATTACCC | ACACCAGCAG | 1260
| GATTACCTGT | AATGGCTAAA | GCAGCACTAG | CTATTTAGC | TTTCGCTGTA | GTTATGTGGG | 1320
| TTACAGAAGC | AGTTACTTAT | CCAGTTTCTG | CAACATTAAT | TTTAGGATTA | ATGATACTTT | 1380
| TACTAGGTTT | AAGTCCAGTT | CAAGATTTAT | CCGAAAAACT | TGGAAACCTA | AAAGTGGCGA | 1440
| CATAATACTA | AAAGGTAGCG | ATATTTTAGG | AACGAATAAC | GCGCTTAGTC | ACGCTTTTAG | 1500
| TGGTTTTTCA | ACCTCAGCCG | TAGCACTTGT | AGCTGCAGCA | TTATTTTAG | CAGTAGCTAT | 1560
| GCAGGAAACC | AATTTACATA | AACGACTTGC | ATTATTTGTG | CTATCAATTG | TTGGAAATAA | 1620

```
AACTAGAAAT  ATAGTCATTG  GTGCTATTTT  AGTATCTATT  GTTCTAGCAT  TCTTTGTACC   1680
ATCAGCTACA  GCACGTGCTG  GTGCAGTTGT  CCCAATATTA  CTGGGAATGA  TTGCTGCATT   1740
TAATGTGAGT  AAGGATAGTA  GACTTGCTTC  ATTATTAATT  ATTACTGCTG  TACAAGCAGT   1800
TTCGATATGG  AATATAGGTA  TTAAAAACGG  CTGCAGCACA  AAATATTGTA  GCCATCAATT   1860
TTATTAACCA  AAATTTAGGA  CATGATGTAT  CATGGGGAGA  GTGGTTTTTA  TATCTGCGCC   1920
GTGGTCAATC  ATTATGTCTA  TAGCTCTTTA  TTTTATAATG  ATTAAGTTTA  TGCCACCTGA   1980
ACATGATGCA  ATTGAAGGTG  GAAAAGAGTT  AATTAAAAAG  GAACTTAATA  AATTAGGACC   2040
AGTCAGTCAT  AGAGAATGGC  GACTAATTGT  GATTTCAGTG  CTTTTATATT  CTCTGGTCGA   2100
CTGAGAAAGT  ATTGCATCCG  ATTGATTCAG  CTTCGATTAC  ACTAGTTGCT  CTAGGTATTA   2160
TGCTAATGCC  AAAGATTGGT  GTTATTACTT  GGAAAGGTGT  TGAAAAGAAG  ATTCCTTGGG   2220
GGACGATTAT  AGTATTTGGT  GTAGGAATCT  CACTTGGTAA  TGTATTACTT  AAAACAGGAG   2280
CCGCTCATGG  TTAGTGATCA  ACATTTGTTT  GATGGGTCTT  AAACATTTAC  CGATCATAGC   2340
AACTATTGCG  TTAATTACCT  TATTTAATAT  ATTAATACAT  TTAGGTTTTG  CAAGTGCAAC   2400
GAGCTTAGCC  TCTGCGTTAA  TACCTGTGTT  TATTTCTTTG  ACTTCAACGC  TAAATTTAGG   2460
TGATCATGCT  ATTGGTTTTG  TATTAATACA  ACAATTTGTG  ATTAGTTTTG  GTTTCCTACT   2520
ACCTGTCAGT  GCACCACAAA  ATATGCTTGC  ATATGGTACT  GGGACTTTTA  CCGTAAAGGA   2580
TTTTTTAAAG  ACAGGTATAC  CTTTAACGAT  AGTAGGTTAT  ATTTAGTTA   TCGTATTTAG   2640
TTTAACGTAT  TGGAAATGGC  TTGGTTTAGT  GTAAGTAAAA  GATTAGGTA   TTAAAATGAT   2700
AATTATAAAT  GTCTCGTAAA  GTTTAATATT  TTAACTTTAC  GACACATTTT  TTATAAACTC   2760
GTGGCAAGTT  AATCTTAATA  GTTGAAATGT  ATCGTATAAA  AATATATGA   ATGTAAATAG   2820
AATTTAGTAT  TAGAGAATAA  CAAAAAATTG  ATGTTAGGTG  GTAAAATCTA  ATGGCTATAG   2880
GTGTCATATT  AAATAGAGTT  TTTAGGCTAA  ATAATAATCC  ATTATTTGAT  TATATATATA   2940
GTAATAAAGA  ATCTATAAAT  CATTGTTATT  TTATTATTCC  AACTGAAGAG  TTTGAAGAAG   3000
AAGCAAAAAA  GAAAGCACAA  TACTATTATG  GGTCCATACA  GAAGTTTATG  TATGAACTAC   3060
AACGATATGA  TATAGAACCC  TTTTTGATGT  CTTATGATAA  ATTAATAGAC  TTTTGTAAAA   3120
AACAAGCTAT  AGACAAGTT   GTTGTTGCAG  GTGATATTAT  GAGTTATCAT  CACGAAGAAT   3180
ATGACATTTT  ACATCAAAGG  AAACGATTTA  AACAAGCTAA  TATTCAAGTA  ATATCATTAA   3240
GAGCAAATCA  TTATTTTAAC  CCCCGCAAAA  CACATAATAA  ACAAGGGGAA  CCATATAAAG   3300
TATTTACCAG  TTTTTATAGA  AAATGGCGTC  CTTACTTAAT  GATTAGAGAT  GAATATGACT   3360
ATCATTTAGA  AGATATTTCA  AAGGTTGTAG  TGAAATCTCA  ACATAAAATT  AAAGAAGATT   3420
ATCATTCATA  TGGTATAAGT  GAACGTGATG  TTCAAAATCG  TTGGTCTGAA  TTTTTATCTC   3480
AAGATATCGA  AAATTATAAA  GAAAACAGGG  AATACTTGCC  TGAAGTATTA  ACAAGCCAAC   3540
TAAGTATTTA  CTTAGCTTAT  GGAATGATAG  ATATTATACA  ATGTTTCAA   CGATTACTT   3600
CAAAATTATG  ATAAAAATGA  ACAAAATTAC  GAAACTTTTA  TACGTGAATT  GATTTTTAGA   3660
GAGTTTTATT  ATGTATTAAT  GACCAATTAT  CCCGAAACAG  CTCATGTTGC  TTTTAAAGAA   3720
AAATACCAAC  AATTGAAATG  GTCTTATAAT  GAAGAGAATT  TTAAACTGTG  GAAAGATGGG   3780
AATACTGGTT  TTCCAATTAT  TGATGCAGCA  ATGGAGGAAC  TTAAAACAAC  TGGATTTATG   3840
CATAATCGCA  TGAGAATGGT  AGTTTCTCAA  TTTTTAACTA  AAGATTGTT   TATTGACTGG   3900
ATTTGGGGTG  AGTCATTTTT  CAAACAAAAA  TTAATAGATT  ATGATGCAGC  TTCAAATGTT   3960
CACGGATGGC  AGTGGTCAGC  TTCTACTGGA  ACAGATGCTG  TACCATACTT  TAGAATGTTT   4020
```

|            |            |            |            |            |            |      |
|------------|------------|------------|------------|------------|------------|------|
| AATCCTATAA | GACAAAGCGA | GCGTTTTGAT | AATAATGCAC | GATATATAAA | AACTTACATT | 4080 |
| CCAAGATTAA | ATCAGGTAGA | TGCTAAGTAT | TTACACGATA | CTCATAAATT | CGAGCAACAA | 4140 |
| ATAAAGGGGC | AAGGTGTTGA | AATAGGTAAA | GACTATCCTA | AACAAATGAT | TGATCACAAA | 4200 |
| GAAAGTAGAC | AACGTGTAAT | GTCAGAATTC | AAAGCTATAG | ATTAAATAAA | AAAGATCTGA | 4260 |
| ACAACATGAT | ATAGGTGTTC | AGATCTTTAT | CTAGTTACAT | AAAAAAGCAA | ACATGAATTA | 4320 |
| AAATATATTC | TAACAAAGTT | AAAATATACA | TATATTTAAG | ATTTAATTTA | GTTTTCAAAG | 4380 |
| GTACTTCCCA | ATTTGTATAA | CGGGGCTCAT | AATAAAATAA | TTGCATCAAA | TATAATCCTA | 4440 |
| TCCCTAACGG | TAAACACATT | AATAAAATAG | CTTTAGTATA | ACTCCATCCT | ATTTGATGCC | 4500 |
| ATAAATGACC | TATCATAAGT | TGAATAATGA | TGAGACATAC | CATTAAAATT | ACTTCAATTA | 4560 |
| TCATTGGTAT | AATCTCACCC | CTTTAATAAA | CAATATGACT | GTTGCTTGTA | TGAGCACCAT | 4620 |
| TAAAACGACA | AATAGTAACG | CTTTAACATC | TATGATTAAA | AAAACCTCTT | TCACAATTTT | 4680 |
| TAAAGGTGCA | TTTAATAAAT | AGACAGTATG | TAATCTTAAG | AATCGACCGA | TGTAAATACC | 4740 |
| TAATCCATTT | AAGAACATTA | ATATAACTAT | CAATAGTCGA | TTTAACCATA | CATAAGACGT | 4800 |
| AAAATGTGCA | ATTTCTAAAA | ATATAAGAAT | TGTGAGGTAT | ATTGCTAAGA | GTACGCCAAG | 4860 |
| TATTAAATAG | GTGAAATAAA | TCCATTCTGT | GATGTTTAAT | CCAGCTAAAA | AGTTAAATTG | 4920 |
| AAATTGGTTT | AAGTGTATGA | GATCGGTAAT | CATATAAAAT | GTGTTTGGAA | CTAATAATAG | 4980 |
| AAATATGAGT | CCGAAAACAA | TAAATAAGGG | CCATTCAAAA | GCTT       |            | 5024 |

( 2 ) INFORMATION FOR SEQ ID NO:8:

( i ) SEQUENCE CHARACTERISTICS:
        ( A ) LENGTH: 3287 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 37

( x i ) SEQUENCE DESCRIPTION: SEQ ID NO:8:

|            |            |            |            |            |            |     |
|------------|------------|------------|------------|------------|------------|-----|
| AAGCTTGCCT | ATTGATTTTA | AAAAATTAAT | GATTATAGGT | TCACTCATAT | CTGTTGCAAC | 60  |
| TGCATCAGTG | CCTATGTTTT | TTGGGAAGCC | ATTTTTATAT | CAAACTGAAG | CAAATGTAAC | 120 |
| ATTTCCATTA | CTAGGACATG | TTCATGTTAC | TACTGTGACT | TTATTTGAGC | TTGGCATCTT | 180 |
| ATTAACAGTA | GTAGGTGTGA | TTGTTACAGT | TATGCTATCT | ATAAGTGGGG | GTAGATCATG | 240 |
| AATTTAATAT | TACTCCTTGT | GATAGGATTT | TTAGTGTTTA | TTGGAACTTA | TATGATTTTA | 300 |
| TCTATTAATT | TAATTCGTAT | TGTTATTGGT | ATTTCTATTT | ATACACACGC | CGGTAATTTA | 360 |
| ATTATTATGA | GTATGGGGAA | ATATGGACCT | CATATGTCTG | AACCGCTAAT | TCAAGGTCAT | 420 |
| GCTCAAAACT | TTTGTTGATC | CTTTATTACA | AGCTATCGTT | TTAACAGCTA | TTGTGATTGG | 480 |
| ATTTGGTATG | ACTGCGTTTT | TATTGGTGTT | AATATATAGA | ACTTACAGAG | TAACTAAAGA | 540 |
| GGATGAAATA | AGTGCATTGA | AAGGTGATGA | AGATGATGAG | TAATTTAATA | ATATTGCCTA | 600 |
| TGTTGTTGCC | TTTTGTATGT | GCTTTAATTT | TAGTCTTCAC | TAAAAATAAA | AATCGTATTT | 660 |
| CGAAAATCCT | ATCCATTACA | ACTATGATTG | TTAATACAAT | GATTTCAATT | GCTTACTTA  | 720 |
| TTTATGTCGT | TAATCATAAA | CCGATAACAC | TTGATTTTTG | GGGGATGGA  | AAGCACCTTT | 780 |
| CGGCATTCAA | TTTCTAGGTG | ATTCACTGAG | TCTGCTTATG | GTGTCAGTAT | CATCTTTTGT | 840 |
| TGTTACGCTA | ATAATGGCAT | ACGGCTTTGG | TAGAGGGGAG | AAGCGAGTCA | ATCGATTCAC | 900 |

```
CTCCTACATT ATCTTTATTA ACAGTAGGTG TTATTGGTTC GTTTTTAACT TCTGATTTAT      960
TTAACCTATA CGTGATGTTT GAAATTATGC TTCTTGCTTC GTTTGTACTT GTTACATTAG     1020
GACAATCTGT TGAACAATTA CGTGCAGCGA TAGTATATGT TGTTCTGAAT ATTTTAGGTT     1080
CGTGGTTGCT TTTATTAGGA ATTGGCATGT TATATAAGAC AGTCGGAACA CTTAATTTCT     1140
CACATTTAGC GATGCGATTG AATCATATGG AAAATAACCA AACAATAACG ATGATATCTT     1200
TAGTATTTCT AGTTGCTTTT AGTTCAAAGG CAGCACTAGT GATTTTCATG TGGTTACCTA     1260
AAGCATATGC AGTGCTTAAT ACGGAACTTG CCGCGTTATT TGCAGCATTG ATGACAAAAG     1320
TTGGAGCTTA TRCGCTTATT CGTTTTTTTA CTTTACTATT CGACCATCAT CCAAGCGTCA     1380
CGCATACATT GCTCGTGTTT ATGGCTTGTA TCACAATGAT TATCGGTGCA TTTGGTGTCA     1440
TCGCTTACAA AGATATTAAG AAAATTGCGG CTTATCAAGT TATTTGTCT ATTGGATTCA      1500
TTATTTTAGG TTTAGGTTCT CATACTATAT CAGGTGTAAA TGGTGCTATC TTCTATTTAG     1560
CGAATGATAT TATCGTTAAG ACATTATTGT TTTTTGTAAT TGGTAGTCTT GTTTATATGT     1620
CAGGCTATCG AAATTATCAG TATTTAAGTG GACTGGCAAA AGAGAACCAT TCTTTGGTGT     1680
TGCATTTGTC GTGGTAATTT TTGCTATAGG TGGCGTACCT CCTTTTAGTG GCTTTCCGGG     1740
TAAAGTCTTA ATATTCCAAG GGGCTATTAC AAATGGTAAT TATATTGGTT TAGCACTTAT     1800
GATTGTGACA AGTTAATTG CTATGTATAG TCTTTTTAGA GTGATGTTTA TAATGTATTT      1860
TGGTGATGCT GACGGAGAAC AAGTACAATT TAGACCACTA CCTATTTATC GTAAAGGTTT     1920
ACTTAGTGTT TTAGTTGTAG TGGTATTAGC GATGGGTATT GCAGCCCCTG TTGTTCTGAA     1980
AGTAACAGAG GATGCAACAA ATCTTAATAT GAAAGAAGAT GTCTTTCAAA AGAATGTAAA     2040
TACACATTTG AAGGAGGTTA ATCATAAGTG AAGCAAGTTG TATTAAATAT TGTTATCGCG     2100
TTCCTTTGGG TACCCTTTCA AGATGAAGAT GAATTTAAAT TTACAACCTT CTTTGCTGGA     2160
TTTTTAATTG GTTTAATTGT GATTTATATT CTGCATCGCT TTTTTGGTGA AGAATTTAT      2220
TTGAAAAAGA TATGGGTGGC TATTAAATTT TTAGCTGTAT ACCTATACCA GCTTATTACT     2280
TCTAGTATAA GTACCATAAA TTACATCTTA TTTAAGACGA ATGAAGTTAA TCCAGGTTTA     2340
CTCACATATG AAACTTCATT AAAAAGTAAT TGGGCTATTA CTTTTTTAAC GATTTTAATT     2400
ATTATTACTC CAGGATCGAC AGTTATTCGA ATTTCTAAAA ATACTAATAA ATTTTTTATT     2460
CACAGTATTG ATGTGTCAGA AAAAGATAAA GAAAATCTTC TAAAAAGTAT TAAGCAGTAT     2520
GAGGATTTAA TTTTGGAGGT GACACGATGA TTGAAATGTT CACTCAAATA TTTATTATAA     2580
GTGCATTAGT GATTTTTGGT ATGGCACTAC TTGTTTGTCT AGTCAGATTA ATTAAAGGTC     2640
CCACTACTGC TGATAGAGTT GTATCATTTG ATGCCTCGAG TGCTGTTGTT ATGTCTATTG     2700
TTGGTGTGAT GAGCGTTATT TTTAACTCAG TGTCTTAATG TTAATTGCAA TTATTTCGTT     2760
TGTCAGTTCG GTCTCAATTT CAAGATTCAT CGGGGAAGGA CGTGTCTTCA ATGGAAATCA     2820
TAAAAGACAT CGTTAGTCTT ATTGCTTCGA TACTTATTTT CTTAGGAAGT ATTATTGCAT     2880
TAATTAGTGC AATAGGGATT GTAAAATTTC AAGATGTCTT TCTAAGAAGT CACGCCTCAA     2940
CGAAAAGTTC TACATTGTCA GTATTACTAA CTGTAGTTGG TGTACTGATC TATTTTATTG     3000
TGAATTCAGG TTTTTTCAGT GTCAGATTAT TATTATCACT AGTTTTTATC AATCTTACAT     3060
CTCCGGTTGG AATGCATTTG ATAAGTAGAG CGGCCTACCG TAATGGTGCA TATATGTACA     3120
GGAAAGACGA TGCATCTAGA CAATCTACTA TCTTATTAAG CCAAAAAGAG TTAATACGC      3180
CAGAAGAATT AAAAAAACGT GCAAAACTAC GAGAAGAAAG ACGAGAAAAA TTATACTATA     3240
AAGAAAAAGA ATATATTAAT AAAATGGACG ATTGATTGTT TAAGCTT                   3287
```

( 2 ) INFORMATION FOR SEQ ID NO:9:

( i ) SEQUENCE CHARACTERISTICS:
        ( A ) LENGTH: 2291 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus faecalis
        ( B ) STRAIN: Clinical Isolate S2- 1

( x i ) SEQUENCE DESCRIPTION: SEQ ID NO:9:

```
AAGCTTTAGA   TAATGATAAA   CGCGTGTATG   TGAATGTCCA   GCCGATTCAA   TCGCCTACTG     60
GAGAAACAGT   GATTGGTGTC   CTTTATGTGA   AAAGTAATTT   AGAAAATAAA   TACCAAGAAA    120
TTACTAACAC   AGCAAGTATC   TTTTTCACTG   CTTCTATTAT   TGCCGCAGCA   ATCTCGATTA    180
TTGTGACCCT   ACTGATTGCA   CGATCAATCA   CGAAGCCGAT   TGGTGAAATG   CGCGAGCAAG    240
CCATTCGAAT   CGCTCGTGGT   GATTACGCTG   GAAAAGTAGA   AGTCCATGGA   AAAGATGAAT    300
TAGGCCAATT   AGCAGAAACA   TTTAATCAAT   TATCAGAACG   GATTGAAGAA   GCACAAGAAA    360
CAATGGAAGC   AGAAGAATCG   TTTAGATAGT   GTCTTAACGC   ATATGACAGA   TGGTGTCATT    420
GCGACGGATC   GCCGCGGAAA   GGTGATTACG   ATTAATGAGA   TGGCCCTTTC   ATTATTAAAT    480
GTAAAAAATG   AAAATGTGAT   TGGGACCTCG   TTATTAGAGT   TGTTAGATAT   TGAAGAAGAT    540
TACACATTGC   GGAAGCTGTT   AGAAGAGCCA   GATGAACTGC   TGATTGATCG   CTCAACGTCT    600
GATCGTGAAG   AAGACCAAAT   GATTATCCGG   GTAGACTTTA   CGATGATTCG   TCGGGAATCA    660
GGATTTATTA   CTGGCTTAGT   TTGCGTACTT   CATGACGTCA   CAGAACAGGA   AAAAAACGAA    720
CGGGAAAGAC   GGGAATTTGT   TTCCAATGTT   TCTCATGAGT   TGCGACGCCT   TTGACAAGTA    780
TGCGTAGTTA   TATAGAGGCT   TTGAGTGAAG   GAGCTTGGGA   AAACCCTGAG   ATTGCGCCGA    840
ATTTCTTAAA   AGTCACGTTA   GAAGAAACCG   ACCGGATGAT   TCGTATGATT   AATGATTTGT    900
TAAATTTATC   TCGGATGGAC   TCTGGGAATA   CACATCTTCA   ATTAGAGTAT   GTGAATTTTA    960
ACGAATTGAT   TAATTTTGTC   TTGGATCGCT   TTGATATGAT   GATTGAAAAT   GAGCAAAAAA   1020
ATTACAAAAT   TCGCCGTGAA   TTTACTAAAC   GCGATTTATG   GGTAGAGTTA   GATACAGACA   1080
AAGTAATTCA   GGTTTTTGAC   AACATTTTGA   ACAATGCGAT   TAAGTATTCG   CCAGATGGCG   1140
GCGTCATTAC   CTGCCGACTA   GTTGAAACAC   ATAATAATGT   CGTCTTTAGT   ATCTCGGACC   1200
AAGGTTTGGG   CATCCCTAAA   AAAGATCTCG   GGAAAGTCTT   CGAGCGTTTT   TATCGTGTGG   1260
ATAAAGCACG   TGCGCGAGCA   CAAGGTGGGA   CTGGTTTAGG   TTTAGCAATT   TCTAAAGAAG   1320
TAATTCGGGC   CCATAACGGG   AGTATTTGGG   TGGAAAGTAC   AGAAGGTGAA   GGATCAACTT   1380
TCTATATTTC   ACTACCATAT   GAACCTTATG   AAGAGGATTG   GTGGGAATGA   TGAAAAAATC   1440
AGAATGGATT   ACAAGAATTG   GCTTGATTTT   GATGGTCATT   TTAAGTATAT   ATTTTTCAGT   1500
CAATATCTGG   CTGAATTCTG   CCAAAAAAAT   ACCAGAAATG   AAGTCGGGAA   GCCAAGTCAC   1560
AACAGCTGTC   AATGAAAAAG   CCATTGGCGA   TGTCTATTTA   CCTTTGCAAT   TGATTCGAAT   1620
AGCCGATGGA   AAAGCGATGC   AAAGTAATCG   TGAAACATTA   ATTAGTAATG   TTCAAAATGA   1680
TATTAAAATG   GCTACGTTTG   GTAAATTGAC   ACAAGTTGTG   ACAAAAAATG   CAGAGCAACT   1740
TAAGCGCTAC   AACCAAATGG   AACAAGGCAT   TGAACTTCTT   TATCAAGGTC   CCTTTTTAAT   1800
CTCGGACTAT   GCTTCGATTT   ATAATCTATC   CATTAATTTT   ACTAACTTTA   ATGAGTTGAC   1860
```

| GGACCAGTAT | TTTACGAAAA | TTCAATTGGA | TTTTAACGAA | AATAAGATAC | GTTTTTTAGA | 1920 |
| TTATGATCAA | TCCAACGTCT | ATGAAGCGCC | CATGACTGTT | AATAAGGCGC | GCTTAATGGG | 1980 |
| AATTATCAAT | AAAGAGGGAT | TGCAATATCA | AGACGTTTCC | GAAAATACGC | TAACCAAACA | 2040 |
| AGGACAATGT | TATTTAACCA | ATGATATGAA | GTTGAAAAAG | TACAGTTATA | TCTTANTTCG | 2100 |
| CAACCAGTTA | CTCGTTTTAG | GAATGCTTTT | TTCAATGAAA | CGGAAGATAT | CCAAACCAAT | 2160 |
| GAAGACAGTC | AAGACTTAAC | CTATACGAGT | AAAGAAGAAC | GATTGTTTGC | AGAAGAAAA | 2220 |
| CTGGGGAAAA | TCGATTTTAA | AGGGACCTTG | CCAGAAGAGA | ATAAACGGGA | CTCAATCTAT | 2280 |
| AATCAAAGCT | T | | | | | 2291 |

( 2 ) INFORMATION FOR SEQ ID NO:10:

( i ) SEQUENCE CHARACTERISTICS:
        ( A ) LENGTH: 3719 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterococcus faecalis
        ( B ) STRAIN: Clinical Isolate S2- 3

( x i ) SEQUENCE DESCRIPTION: SEQ ID NO:10:

| AAGCTTCATT | AGAGCGTCAA | CTGTTTTTGG | TGTTGGGTTC | ACAATGTCAA | TTAGACGTTT | 60 |
| GTGAGTACGC | ATTTCGAATT | GTTCGCGAGA | ATCTTTGTAT | TTATGAGTCG | CACGAATAAC | 120 |
| TGTGTAAAGT | GAGCGTTCTG | TTGGTAATGG | AATCGGACCT | GATACGTCAG | CTCCAGTTCT | 180 |
| TTTTGCTGTT | TCCACAATTT | TATCCGCTGA | TTGATCTAAA | ATACGGTGTT | CATACGCTTT | 240 |
| TAAACGGATA | CGAATTTTTT | GTTTTGCCAT | CTTGTTCCCT | CCTTCGCCTA | TTTTAAAAGT | 300 |
| AGACATAGCT | CCACGAAAAT | TTATCCGGCA | TGCTCGTTCA | TGGCAAAGCG | TCCGAGCGTG | 360 |
| TCGCAACCTC | TCGCTTCACA | GCCGGCAAAT | CAAATCGTTG | ATCTACCAAT | GCTTTTTACA | 420 |
| CTCCTGTAAA | CAGCACCTTT | TTGATTATAC | TATGAAAGGA | TAGTGTTAGC | AAGGATTTTC | 480 |
| TGCGTTTTTT | TAAAAGAATT | TTTTCTTGTT | TTGAAAAGCA | TTTGTTTTGT | TTTTCAATTC | 540 |
| TTTTCATTCT | ATTTTTATAA | AAAAAGAATT | TGAGATTCTT | TTTTTACCAG | AATCTCAAAT | 600 |
| TCTTTCTTTT | TTATTCTATT | AACCAATCCG | GCGCATTGGA | ATATCATTGT | TATCTGGATG | 660 |
| AACCAATAAA | TATTGAATAA | CATCAATATT | GCTTGCTTGG | AATGAGGCTG | CACATGCTTG | 720 |
| CAAATATAAG | TCCCACATTC | GATAGAAGCG | CTCGCCTTTT | TCGTCAACAA | TTTCTGTTTC | 780 |
| TATATTATGG | AAGTTTTTG | TCCAATGTTC | CAACGTCAAT | TGATAATCTC | TGCGCAAACT | 840 |
| TTCCAAGTCA | ATCACTTGCA | AGTCGTTTTC | TGTCATATGG | CCGACTAGCT | CAGTGACACC | 900 |
| AGGAATATAG | CCACCTGGGA | AAATATAACG | ATTAATCCAA | GCATTTTTAG | CCCCACCTTG | 960 |
| TTGGCGACTG | ATCCCATGAA | TCAACGCCGT | ACCTTTAGGC | GCTAAATTTC | GCTGAACGAC | 1020 |
| ATCAAAATAT | TCATGTAGAT | TTTCCGCACC | GACATGTTCA | AACATCCCAA | CACTCGTAAT | 1080 |
| ATGGTCAAAA | GACTCTCCTT | TTAAATCACG | ATAATCCATC | AATTTGACAG | TCATTCGATC | 1140 |
| TTGTAGACCT | TCTTTTTCTA | TAATATGGCG | AATATGATGA | AATTGCTCTT | CACTTAATGT | 1200 |
| AATCCCAGTT | GCTTTGGCTC | CATATTCTTT | CACCGCAGTT | AAAATTAACG | TGCCCCAGCC | 1260 |
| GCAGCCAATA | TCCAGTAAAG | TGTCGCCCTC | TTTGATAAAC | AATTTATCTA | AAATATGATG | 1320 |
| AACTTTATTC | ACTTGCGCTT | GTTCTAATGT | ATCTTCAGGC | GTTTTAAAAT | AAGCACATGA | 1380 |
| ATACGTCATT | GTTTGGTCAA | GCCATTTTTT | GTAAAAATCA | TTTCCTAGAT | CGTAATGGCT | 1440 |

```
GTGAATATCC  TCTTGCGAAC  GTTTTTTTGA  ATGACTTTCT  TTAGGAAGCC  ATTTAATAAA  1500
TTTAGCATTG  TGTAAAAAGC  TATCCTTTTG  GTTATACACA  TCATAAATCA  GCGCTTGGAT  1560
ATCGCCTTCG  ATTTCAATTT  TGCGATCCAT  GTAGGCTTCC  CCTAAAGTTA  ACGAAGCGTT  1620
ATTCAGTAAA  TCCTTCACAG  GAATTTTTTC  ATTGAATACA  ATTTTAAAAA  CCGGATCCCC  1680
CGACCCTTGC  CCATACTCTT  TGACGGTACC  ATCCAGTAT   GTGACTTGTG  TCTTTTTTGA  1740
AAAAGACCAT  TTAAACAGTT  GACTGTACGT  TTCTTTTTCT  AACATTGCAT  TCCCTCCATT  1800
AAATACCATT  TGAAGCCAAA  ACAAAAGAA   GTCGCTTTCC  GGTAGTTCGT  CAAAACAAAC  1860
ACCACAGTCC  GTTCTAAACT  GAAGCACAGA  AAAGTTATCA  CCCCTTCTAT  GTTCCGCTTC  1920
TTTTTTGCAA  TTACAGTTCT  ATTCTACTCC  TCTTTTAAAA  ATTTGAACAT  TCTTTTAACG  1980
TAATACCTAC  TATTGTTATT  CTTTATCACA  AAAAAACTAG  AGCCAGTCCT  TGACAGACTC  2040
CTCTAGTTCT  AAATATTATG  CTTTCTTACG  CATCCGTTGT  TCCGCATGAG  TGTAAGCGCC  2100
ATGCCACACG  TGCCCCACAT  AAGGATTAAC  TTGAATACCG  TGTTTAATCG  CCGCTGCTAC  2160
AAATTTTTCG  CTAAAGTTAC  TGCTTCTAAC  ACCGAATAAC  CTTTCGCCAA  GCCAGCTGTG  2220
ATTGCCGCTG  AAAAAGTACA  ACCTGCACCA  TGATTATAAT  CAGTTGGATA  TAATTCATTT  2280
TCCAAAAGAT  GCGCGGTGTG  ACCATCGTAA  AATAAGTCCA  GTGCTTTTC   ACCAGCTAAG  2340
CGATGTCCCC  CTTTAACCAC  GACATGCTTG  GCTCCCATTT  GTACAATTCG  TTTTGCCGCT  2400
TCTTCCATCT  CCGCCACGGA  AGAAATTTCG  CCTAAACCAG  ATAAGATGCC  CGCTTCAATT  2460
AAATTAGGCG  TGGCAACTAA  TGCTAATGGC  AGTAAATCGT  TTTTAGGCCT  TCCACACTTT  2520
TGGGTTGCAG  AATTTGTGCC  GTTCCCTTAC  AAGCAATGAC  TGGGTCAATC  ACGACTTTTT  2580
GAATTTTTTC  TTGTTTAATG  TACTTACTAG  CCATTTTAAT  ATTTGTTCA   TTACCCCATC  2640
ATCCCTGTT   TTCAAAGCCG  CTACTGGACC  GCCTGCAAAA  ACCGAAATCA  ATTGTTTTC   2700
TAAGAGCGTT  TCTGGCAATT  CAGTTACTTC  ATGTGACCAA  CCTGTCGTAG  GATCCATCGT  2760
CACAATCGAG  GTTAAACTTG  AAAATCCAAA  AACTCCATAC  TCTTCAAATG  TTTTTAAATC  2820
TGCTTGAATC  CCTGCCCCTC  CAGTTGAATC  GGAGCCTGCA  ATCGTCAATA  CTTTTTCCAT  2880
TAAATCACCT  AACCTTTTTC  TCCAAGTATA  CGGAAGAAAC  AAGTCTGCTA  AAACAGCCAA  2940
TTGGCTTATT  TTTTAGCCAG  CCAATTTCTA  AACAAAAAA   AGACCAGAGA  ATAAATTCTC  3000
TGGTCTTACG  TCCGAATACC  CCAGTTTTTC  ACGCTGGTTA  AAGCTATAGT  TAAAAAGTTA  3060
ATTATTTAAC  GATTTCAGTA  ACAACGCCTG  AACCTACAGT  ACGTCCGCCT  TCACGAATAG  3120
AGAAACGAGT  TCCGTCTTCG  ATAGCGATTG  GGTGAATTAA  TTCAACGTCC  ATAGCAACGT  3180
TATCACCAGG  CATTACCATT  TCAGTACCTT  CTGGCAATTC  TACAACACCA  GTAACGTCTG  3240
TTGTACGGAA  GTAGAATTGA  GGACGATAGT  TAGTGAAGAA  TGAGTGTGAC  GTCCGCCCTC  3300
TTCTTTTGAT  AATACGTATA  CTTCAGCTTT  GAATTTTGTG  TGTGGAGTGA  TTGTAGCTGG  3360
TTTAGCTAAT  ACTTGTCCAC  GTTCGATATC  TTCACGTGCA  ACACCACGTA  ATAAAGCACC  3420
GATGTTGTCG  CCTGCTTCAG  CGTAGTCTAA  TAATTTACGG  AACATTTCAA  CACCTGTAAC  3480
AGTTGTTTTA  GATGTTTCGT  CTTTAATACC  AACGATTTCA  ACTTCGTCAC  CAACGCGAAC  3540
TTCACCACGT  TCAACACGGC  CTGTAGCAAC  AGTACCACGT  CCAGTGATTG  AGAATACGTC  3600
TTCGACTGGC  ATCATGAATG  GTTTGTCAGT  ATCACGTTCT  GGAGTTGGGA  TATATTCGTC  3660
AACTGCAGCC  ATTAATTCTA  AGATTTTTTC  TTCATAAGAC  TCGTCGCCTT  CTAAAGCTT   3719
```

( 2 ) INFORMATION FOR SEQ ID NO:11:

( i ) SEQUENCE CHARACTERISTICS:
    ( A ) LENGTH: 3480 base pairs
    ( B ) TYPE: nucleic acid
    ( C ) STRANDEDNESS: double
    ( D ) TOPOLOGY: linear ( i i ) MOLECULE TYPE: Genomic DNA ( v i ) ORIGINAL SOURCE:
    ( A ) ORGANISM: Enterococcus faecalis
    ( B ) STRAIN: Clinical Isolate S2- 7

( x i ) SEQUENCE DESCRIPTION: SEQ ID NO:11:

```
AAGCTTCTAG  CGTTTCGGAT  TGGCGCCTAT  GATGCACCAG  GAGAGCGACG  AATCAATACC    60
AAAAATATGC  CTACAGCAGG  AGGACTTGCA  ATCTACATTG  CTTTTGCTAG  TTCATGTTTA   120
TTGATTTTTC  GTTCGATTAT  CCCACAAGAT  TATATTTGGC  CGATTATTTT  GGCTGGTGGA   180
ATGGTTGTTT  TGACAGGCCT  CATTGATGAT  ATTAAAGAGA  TTACTCCAAT  GAAAAAAACA   240
ATCGGTATTT  TGTTAGCAGC  ATTAGTTATT  TTATTTTGTT  GCTGGAATTC  GGATAGATTT   300
TGTGACGTTG  CCAGTTGTTG  GAATGATTGA  TTTGCGCTGG  TTTAGTTTAC  CACTAACTTT   360
ATTGTGGATT  TTAGCGATTA  CGAATGCAGT  AAATTTAATT  GATGGTTTGG  ATGGTTTAGC   420
ATCAGGCGTA  TCCATTATTG  GATTAACCAC  GATTGGTATT  ACAGGGTATT  TTTTCCTACA   480
TGCTAAAACG  GTCTATATCC  CAATTGTTAT  TTTTATTTTA  GTTGCGAGCA  TTGCGGGATT   540
TTTCCCATAC  AATTTTTATC  CGGCTAAAAT  ATTTCTAGGA  GATACCGGGG  CGTTATTCCT   600
CGGGTTTATG  ATTGCAGTAA  TGTCGTTACA  GGGCTTGAAA  AATGCTACGT  TATTACGGT    660
AATTACGCCA  ATGGTGATTT  TAGGTGTGCA  ATTACGGATA  CGGTTTATGC  AATTATTCGA   720
CGGCTATTGA  ACAAGAAGCC  CATTTCCTCA  GCAGATAAAA  TGCATTTACA  TCACCGCTTG   780
TTATCTTTAG  GTTTTACCCA  TAAAGGGGCG  GTCATGACTA  TTTATGCATT  AGCGTTAGTT   840
TTTTCCTTTG  TCTCTTTATT  GTTCAGCTAT  TCAAGTACAG  TAGCATCAAT  TTTATTAATT   900
GTCTTTTGTT  TAATTGGCTT  AGAACTATTC  ATTGAACTAA  TCGGTCTAGT  TGGCGAAGGG   960
CATCAACCGT  TGATGTATTT  GTTACGGATT  TTAGGGAATC  GTGAATATCG  TCAGGAGCAA  1020
ATGAAAAAGC  GACTTGGCAA  GCATTCTAAG  AGAAAGTAAA  GAAATCTTTA  GGTTGCTTTG  1080
CGAGAGCTAA  ACCTATGATA  TAATTCCATT  AAACTTAAAA  AAGTATATGT  GTGAAACATA  1140
TGCTTTTTTT  TTAAGACGAT  GTTTCAGTAG  TAAGGAGAAA  TGAGCATGCA  AGAAATGGTA  1200
ACAATCTCGA  TTGTCACTTA  TAATAGTCGT  TACATTTTTA  ATGTACTAGA  CCAATTAAAA  1260
GCCGAACTAG  GTACTGATAG  TATCTATGAT  ATTCATATCT  ATGACAATCA  TTCTGAAACA  1320
GCGTATCTTG  AAAAATTAAC  AACATATGAA  CCATTTATTA  CTATCCATCG  CGCTGAAGAA  1380
AATCAAGGGT  TTGGTCATGG  TCATAATCAA  GTGTTATTCA  ATGCTTCGAC  AAAGTATGCA  1440
ATTATTTTTA  TCCCGATGTG  TTGGTTACTA  AAGACGTGCT  TGATCGTTAT  TAGACGTATC  1500
AAATAGATAA  GAACATTGCA  GTCGGTAGCC  CTAAAGTTGT  TAAATGAAGA  TGGCACGACG  1560
CAATATTTAG  TTCGTCAAAA  ATTAGATGTC  TTCGATTATA  TGTTACGTTT  TATTCCCTTT  1620
CAATTGTAA   AGAAAATTTT  TGATAAACGT  TTGAGTATTT  ATGAATGTCG  CGATTTGTCG  1680
GATACAGAAA  CAACGGATAT  TAAAATGGGC  TCAGGCTGTT  TTATGTTGAT  TGATCGTGAA  1740
AAATTCGTTG  AAATTGGTGG  GTTCGATGAA  CGTTTCTTCA  TGTACTTTGA  AGACAACGAT  1800
TTATGTTTAC  GCTTTGGCAA  AGCAGGCTAT  CGGATTCTCT  ATACGCCTTT  TGAAACGGTT  1860
GTTCACATGT  ATGAAAAGGG  CGCCCATAAA  AGTCGAAAAT  TGTTTAAAAT  CTTTATGCAA  1920
TCAATGGGGA  AATTTTTTAA  CAAATGGGGC  TGGAGGTTCT  TTTAATGAGT  CAAAGATTAG  1980
```

| | | | | | |
|---|---|---|---|---|---|
|CGGTAGTCAT|CGTCTTATAT|CAAATGAAAA|TGGCTGATAC|GCCGAATTAT|TTGTTATTAA 2040|
|AAGAAGTGGT|AGACCACCCC|CAATTGCACT|TATTTATTTA|TGACAACAGT|CCACTTCCTC 2100|
|AAGAAGATGC|ATTATTTTTA|CAACCAAATG|TTACTTATCG|ACATAATCCT|GATAATCCAG 2160|
|GACTAGCGAC|CGCTTATAAT|GAAGCGATTG|CTTTTAGTCA|AGCGAATCAA|TGTGAATTAT 2220|
|TGTTGCTCCT|TGACCAAGAC|ACAGAAGTGC|CAGCCTCTTA|TTTTGATACG|TTGATCATCA 2280|
|TGCCATTAGA|TCCGACTGTG|GCAGTCTATG|TTCCAATTGT|AGAAGCAAAT|GGACAACAAA 2340|
|TTTCGCCAGT|ATATAGTGAT|CAATACGTTG|GGCTTAAAGG|AGCAAAGCCA|ACAGCAGGGA 2400|
|TAGCCAACCA|ACCGTTGATG|GCTATCAATT|CTGGTACAGT|TATTACGGCA|GAAACGCTAC 2460|
|GCTGGTTGGA|AGGATTTTCG|GAAGAATTTC|CTTTGGACTA|TTTAGACCAT|TGGTTCTTTT 2520|
|ATCAATTAAA|TCAAGCCAAT|AAAAGATTG|AAGTCTTACC|AATCCACCTA|AAACAAGAAT 2580|
|TGTCTGTTTT|AGATTATCGT|ACAATGAGTC|CTCAACGTTA|TCGCTCTATT|ATTGAAGCAG 2640|
|AAACGTTATT|TTATCGTCGA|TATGATCAAG|AAAAGTTTC|CCATCATCGA|CGCCATTTAT 2700|
|TTTTACGCAG|TAGTAAGCAA|TTTTTAACTG|TCAAAATCG|CCAAATTTGG|CGGCAAACAT 2760|
|TGGCAGAATT|TCTCAAGTTA|ATGAAGGAT|AATCTATGAT|CTCAGTTTGT|ATTGCGACAT 2820|
|ATAATGGAGA|AAAATATCTC|GCGGAACAAT|TAGATAGTAT|TCTTTTACAA|GTCAGTGAAG 2880|
|AAGATGAACT|AATTATTTCA|GATGATGGTT|CTACTGATCA|TACGTTGGAA|ATTTTGAGGA 2940|
|CGTATGCAGC|GAATTATCCC|CAAATTCAAT|TGTTACAAGG|TCCCAGGGCA|AGGAGTGATT 3000|
|GCTAATTTTG|CATTTTGCCT|TACGCATACG|AAAGGCGAAG|TAATATTTTT|AGCAGATCAA 3060|
|GATGATGTTT|GGTTGCCAAA|TAAAGTAACG|ACGGTGACAG|AATATTTTGA|AGCGCACCCT 3120|
|GACATCCAAG|TGGTTATTAG|TGACTTGAAA|ATTGTTGATG|CGGATTACA|AGTTACCAAT 3180|
|CCCTCTTATT|TAAGTTTCGA|AAAGTCAAAC|CAGGGTTTTG|GCGAAATGCG|ATAAAAGTG 3240|
|GCTATATTGG|GGCAGGTATG|GCCTTTCGTC|AAGAAATGAA|AAACGTCATT|TTACCCATTC 3300|
|CGCCAGAAGT|TCCTATGCAT|GATATGTGGA|TTGGCTTATT|AGCTGCACGG|AAGAAGCAAA 3360|
|CGGGTCTCAT|TAAAGAACCA|TTAGTGCTTT|ACCGAAGACA|TGGAGCGAAT|GTCAGCCCCA 3420|
|TTATTACCAA|AACAAGTTTC|CAACAAAAAT|TAAATTGGCG|TGTGAATTTA|TTAAAAGCTT 3480|

( 2 ) INFORMATION FOR SEQ ID NO:12:

( i ) SEQUENCE CHARACTERISTICS:
        ( A ) LENGTH: 2441 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterococcus faecalis
        ( B ) STRAIN: Clinical Isolate S2- 27

( x i ) SEQUENCE DESCRIPTION: SEQ ID NO:12:

| | | | | | |
|---|---|---|---|---|---|
|AAGCTTCTGC|GCTAGGAACC|AGCCCTTTAA|TTACATCTCC|CCATACTGGA|TTTGACAATG 60|
|CCACTTGATA|AGCAAAAATC|ACAAAATAA|CAACAATTAA|AGCAACAACA|ATAGCTTCAA 120|
|TTTTTCTAAA|ACCAATTTTT|GTCAATAACA|ACAAAGTAA|AACATCAAAT|ACCGTAATGA 180|
|AGACAGCCAG|ACCTAAGGA|ATATGAAATA|ATAAATATAA|GGCAATTGCG|CCCCGATAA 240|
|CTTCAGCGAT|ATCTGTAGCC|ATAATTGCTA|ACTCTGTTAA|AATCCATAAT|ACAATACCTA 300|
|ACGTCTTACT|AGTTCTAGCA|CGAATCGCTT|GTGCTAAATC|CATCTGTGAA|CAATGCCTAA 360|
|TTTAGCAGCC|ATATATTGGA|GCAACATTGC|AATCAAACTG|GAAATTAAAA|TAATCGACAT 420|

| | | | | | |
|---|---|---|---|---|---|
|CAATAAATAT|TGAAAATTTT|GTCCCCCAGT|AATTGAAGTA|GACCAGTTTC|CTGGATCCAT|480|
|ATACCCCACT|GCTACCAATG|CTCCTGGACC|TGAGTAAGCA|AATAACGTTT|TCCAAAAACT|540|
|CATATTTTTA|GGCACGTCGA|TGGTGCCATT|AATTTCTTCA|AGCGAAGGAC|CATTTGCATA|600|
|TTCAATCAAA|TGATGTCTTT|GCTTTGGTTC|ATGTTCTTCT|GAATTTTTCA|ATTCAATTCC|660|
|TTCTTTCGTT|TTGCAATAAT|TTTAAAAGGC|CCTTCCCGTT|AGAAGGTTAA|CCTCTAGTAT|720|
|ATTTTAGGTA|CACCTAAAAT|ATACTGCTAA|AAATAACAAA|ATGCAAGACT|TGAAAGAAAA|780|
|TTTTGACAGT|GTAAAAATAG|ATTGTCGTAA|ATGTGCGATC|TTAAAGTTTG|AAGAAATCAG|840|
|GGTAGCTGGT|AGTTGATTAT|CTTAAGAAGT|AGAAAATAAG|GGACCTAAGT|CATTTCGGCT|900|
|TAGGTCCCTT|ATTTTATTTT|TATTCGGTTA|TTCTATTAAG|AATGGATGCT|ACAATTTCTG|960|
|TCGTGTCAGC|TGAATGATTT|CTAAAATCTC|GTAAACTTAA|TCTGACGAAA|ACCTTCAAGT|1020|
|ACTTCGGGCA|ACTTATTTTN|CCCCCATTCA|AAAGTTCCAT|CATTTCTTTT|CAATAATCTT|1080|
|TGTAAAATTT|CTTCTTTCTC|GACCGCTAAC|AAAAAATGAT|AAACGTCAAT|GCCTGCTCGT|1140|
|CTCAGATATC|CAATCAGCTC|TTCTTCATAT|TCATTTTTAT|AAAGGGTCAT|TGTAACAATA|1200|
|ATCGGCCGTC|CAGACTCTTT|GGACATTCGT|TTTAATAAAT|GAGCATTCCA|GCAACGCCAT|1260|
|TCCTGATACT|CCTGAAAATC|ATTTTCTTTC|ATTTCTTCGG|GAACTAGCTC|CATCAATGCA|1320|
|CTACCAATAA|TTTCTGGATC|ATAAATGATT|GCGTTGGGAA|GTTTTGTTG|TAACTCATGT|1380|
|GCAATGGTCG|TTTTTCCGGA|TCCAAACGCA|CCGTTTAACC|AAATAATTAT|CATAATTTCC|1440|
|TTTTCTTCTG|AACAAATTTC|TTTGTTGTTT|AATTTAGGTG|CTAGATTACT|TTTAATTTTT|1500|
|TTAGCCATTC|ACTTATAGTT|ACTACTTACA|TCTTTAACAG|TAAACGAGAC|AAACTAAAAA|1560|
|TACAACATCC|TACGCTATTA|ACCTCGGGTT|ATATAACATA|CTCATCTGAT|AATTTCTCCC|1620|
|TAAAAAACA|GAATGTGGGC|AATCTTTTA|AGAATAATTG|AATAGAATAA|CAACAAACAG|1680|
|TAATTCAGGT|ATAACCAGCT|AGAAATTGTT|TTATTTTTAG|TCACGAGTAT|GATAAGCATG|1740|
|TAAATCAAAT|AGAATCATAT|TAGGTGAGGT|TACTCTGAAG|AACACAGGTT|ATCGCTCGGA|1800|
|AATGTCGAGA|GACAGTAACG|AGTAAAGCAG|GGATTGTCGA|ATTAAGGCTT|TCCTAAGATA|1860|
|ACTAGAATTT|TTTTCTTACG|TCTCAGAAAG|CCAAAGCTCA|ATTATTGTGA|TTACCCTATA|1920|
|ATCTTCTTCT|TTTATTCGGC|GACCTCTTTA|ATATGATTAA|TTGGAGGTTT|TAAATTGAA|1980|
|AGCTGTCACT|GCATCATCTA|AGAAAAATAC|CCTACTTGCT|AAAAGTATCG|GGAATCTTAC|2040|
|CTTGCTCATC|ATTTTAGGCA|TTTTCATTTT|TATCATCGTC|TTCTCTTGGC|TAAAAATGAA|2100|
|TCGCCCTCTC|CACACCCTTC|CCTCAGAAGA|ATTCCTCGCA|ACACCAAGTA|AAACAGATGA|2160|
|TTTCTTATCT|CCATCAAATC|TTTTTTACTT|TTCAATTCGA|ACCATGTTTC|GAATGATTGT|2220|
|GGGGATGGCT|TGGTCCTTCC|TGTTTTCCTT|TGTTTTGGT|ATTTTAGCCG|TAAAATATAA|2280|
|AACGGCACGA|AGAGTCATTT|TACCATTAGT|TAATTCCTT|GAATCTGTTC|CATTGCTAGG|2340|
|TTTTTTGACC|TTTACAACTG|CTTGGTTACT|TGGTTTATTT|CCAGGAAATG|TGATGGGCGC|2400|
|AGAAGCGGTT|GCTATTTTTG|CCATCTTCAC|AGGTCAAGCT|T||2441|

(2) INFORMATION FOR SEQ ID NO:13:

(i) SEQUENCE CHARACTERISTICS:
        (A) LENGTH: 9515 base pairs
        (B) TYPE: nucleic acid
        (C) STRANDEDNESS: double
        (D) TOPOLOGY: linear (ii) MOLECULE TYPE: Genomic DNA ( v i ) ORIGINAL SOURCE:
    ( A ) ORGANISM: Pseudomonas aeruginosa
    ( B ) STRAIN: Clinical Isolate P2- 2

( x i ) SEQUENCE DESCRIPTION: SEQ ID NO:13:

```
AAGCTTTCCT  CCAGACCCTT  CACCGCCGTG  GAGATCGACG  GCTGGGCGAT  GTACAGCTTG     60
CGCGAGGCCT  CGGCCACGCT  GCCGCATTCC  ACGGTGGTCA  CGAAATACTT  GAGTTGCCGC    120
AAGGTATAGG  ACGCCACTGC  AAGACCTCAT  CGGCGCATCA  TCCTCCCCGG  GCCGGGCGTG    180
CGCGCCTCGA  TTGTTGTGTC  CGCCGCGCTG  CAAGCAAGTT  GCAGGCCGCT  GCCGAGCGTC    240
GCGCGCTGGC  CGCGGAACGA  TTGCCCGCCT  GCACGATAAC  CCAGCACGAC  GCACTTTGCC    300
GGGGCACGCC  TGGCCAGCTT  TTTCTTATGT  CCCGAGGACA  TTTTTAATAA  TTTTCCTTCG    360
CCGCGGCTTG  CGCGACCATC  CTTCCCCATC  GACCCCATGG  ACAGCGGTTC  GCCTCCCGGC    420
GGTCCGGGCC  ATGCGTGCAG  AACCACGACC  GGCGCAGACC  GGCGAGATAA  CAAGGAGAAG    480
GTGGGGTGTT  CGAACTCAGC  GATTGGCAAC  GGCGCGCCGC  GACACAGCGC  TTCATCGACC    540
AGGCCCTGAT  CGGCGGCCGC  CAGCGTCCAG  CCGCCAGCGG  CGCTACCTTC  GACGCCATCG    600
ATCCGGCGAG  CAATCGCCTG  CTGGCGCGGG  TCGCGGCCTG  CGATGCGGCC  GACGTCGACG    660
CGGCAGTGGC  CGCCGCCCGC  CGCGCCTTCG  ACGAAGGCCC  CTGGGCGCGT  CTCGCCCCGG    720
TCGAGCGCAA  GCGCGTGCTC  TGCGCCTGGC  CGAGCTGATG  CTGGCCCATC  GCGAAGAGCT    780
GGCGCTGCTC  GACTCGCTGA  ACATGGGCAA  GCCGGTGATG  GACGCCTGGA  ACATCGATGT    840
ACCCGGCGCC  GCCCACGTCT  TCGCCTGGTA  TGCGGAAAGC  CTCGACAAGC  TCTACGACCA    900
GGTCGCGCCG  GCCGCCCAGC  AGACCCTGGC  CACCATTACC  CGCGTGCCGC  TGGGGGTGAT    960
CGGCGCGGTG  GTGCCGTGGA  ACTTCCCGCT  CGACATGGCC  GCCTGGAAGC  TCGCCCCGGC   1020
CCTGGCCGCC  GGCAACTCGG  TGGTGCTCAA  GCCGGCCGAG  CAGTCGCCGT  TCTCCGCCCT   1080
GCGCCTGGCC  GAGCTGGCCC  TGGAGGCGGG  GGTGCCGGAA  GGCGTGCTGA  ACGTGGTGCC   1140
GGGCCTCGGC  GAGCAGGCCG  GCAAGGCCCT  CGGCTTGCAC  CCGGAGGTGG  ACGCACTGGT   1200
GTTCACCGGC  TCCACCGAGG  TCGGCAAGTA  CTTCATGCAG  TATTCCGCGC  AATCCAACCT   1260
CAAGCAGGTC  TGGCTGGAGT  GCGGCGGTAA  GAGTCCGAAC  CTGGTGTTCG  CCGATTGCCG   1320
CGATCTTGAC  CTGGCGGCGG  AAAAAGGCGC  CTTCGGCATT  TTCTTCAATC  AGGGCGAGGT   1380
CTGTTCGGCG  AACTCGCGCT  GCTGGTGGA   GCGTTCGATC  CACGACGAGT  TCGTCGAGCG   1440
CCTGCTGGCC  AAGGCCCGCG  ACTGGCAGCC  GGGCGATCCG  CTGGACCCGG  GCCAGCCGCG   1500
CCGGCGCCAT  CGTCGACCGC  CGGCAGACCG  CCGGGATTCT  CGCCGCCATC  GAGCGGGCGC   1560
AAGGCGAGGG  CGCGACCCTG  CTCGCGGTGG  CCGCCAGTTG  ACGATCAACG  GTTCGGACAA   1620
CTTCATCGAA  CCGACCCTGT  TCGGCGACGT  ACGCCGGAC   ATGCAGCTGG  CCCGCGAGGA   1680
AATCTTCGGC  CCGGTGCTGG  CGATCAGCGC  CTTCGACTCC  GAGGACGAGG  CCATACGCCT   1740
GGCCAAGGAC  AGCCGCTACG  GCCTCGCCGC  CTCGCTGTGG  AGCGACGACC  TGCACCGTGC   1800
GCACCGGGTG  GCGCGGCGCT  TGAATGCCGG  AACGTGTCGG  TGAATACCGT  GGACGCGCTG   1860
GACGTCGCGG  TGCCTTTCGG  CGGCGGCAAG  CAGTCCGGCT  TCGGTCGCGA  CCTGTCGCTG   1920
CATTCCTTCG  ACAAGTACAC  CCAGTTGAAG  ACGACCTGGT  TCCAGTTGCG  CTGAAGACGC   1980
GACGGACGCG  ACACGACTCG  ATGCCGATAA  CGACAACAAG  AGGACGATCG  AATGAACGAC   2040
ACGCCGAACG  TGCGTGAGCC  GGCCCTGCGC  CGCGTGCTCG  GGCTGGGACC  GCTGCTGGCG   2100
GTGGCCATCG  GCCTGGTGGT  TTCCCAGGGC  GTGATGGTAC  TGATGCTGCA  AGGCGCCGGG   2160
ACGGCCGGCC  TGGGCTTCAT  CGTGCCGCTG  GGAGTGGCCT  ACCTGCTGGC  GCTGACTACG   2220
```

| | | | | | | |
|---|---|---|---|---|---|---|
| CCTTTTCCTT | TTCCGAGCTG | GCCCTGATGA | TTCCCCGCGC | CGGTAGCCTG | AGCAGCTACA | 2280 |
| CCGAGGTGGC | CATCGGGCAT | TTCCCGGCGA | TCCTGGCGAC | CTTTTCCGGC | TACGTGGTGG | 2340 |
| TGGCGATGTT | CGCCCTCTCG | GCGGAACTGC | TGCTGCTCGA | CCTGATCATC | GGCAAGGTCT | 2400 |
| ACCCCGGCGC | GCTGCCGCCG | ATGCTGGTGC | TACGGCGTGC | TCGGCCTGTT | CACCCTGCTC | 2460 |
| AACCTGCTCG | GCATCGACAT | CTTCGCGCGC | CTGCAGAGCG | CGCTGGCGCT | GCTGATGATG | 2520 |
| ATCGTCCTGC | TGGTGCTCGG | CCTGGGTGCG | GTGAGCAGCG | ACCACGCTTC | CGCGCAGACC | 2580 |
| GCCCTGGCGA | GCGGCTGGAA | CCCGCTGGGG | GTAAGCGCCC | TGGCGCTCAC | CGCGATGGCC | 2640 |
| GTGTGGGGCT | TCGTCGGCGC | CGAGTTCGTC | TGCCCGCTGG | TGGAGGAGAC | GCGGCGTCCG | 2700 |
| GAGCGCAACA | TCCCGCGTTC | GATGATCCTC | GGCCTGAGCA | TCATCTTCCT | GACCATCGCC | 2760 |
| CTCTACTGCT | TCGGTGCGCT | GCTGTGCATC | CCGCAGGCGG | AACTGGCCGG | CGACCCGCTG | 2820 |
| CCACACTTCC | TCTTCGCCAA | CCGCGTGTTC | GGCGAGTACG | GCCAGCTGTT | CCTGGTGATC | 2880 |
| GCCGCGATCA | CCGCCACCTG | CAGCACCCTC | AACTCGTCGC | TGGCGGCGAT | CCCGCGGATG | 2940 |
| CTCTACGGGA | TGGCGCAGAA | CGGCCAGGCC | TTCCCGCAAT | TCAAGCAGCT | CAGCCGGCGG | 3000 |
| GCGCGCACGC | CCTGGGTGGC | GGTGCTGTTC | GTCGCCGCGA | TCACCGGCCT | GCCGATCCTG | 3060 |
| ATCCTCGGCC | AGGACCCGGA | CTCGATCAAC | CTGCTGCTGC | TCGCCGCCGC | GCTGGCCTGG | 3120 |
| CTGCTGGCCT | ACATCATCGC | CCACGTCGAC | GTGCTGGCCC | TGCGCCGTCG | CTATCCGCAC | 3180 |
| ATCGCCCGTC | CGTTTCGCAC | GCCGTTCTAC | CCGCTGCCGC | AACTGTTCGG | CATCGCCGGG | 3240 |
| ATGATCTACG | CGGTGGTCCA | CGTCTCGCCG | ACCCCGGAAA | TGACCGGACG | GATCTTCGCC | 3300 |
| AGCGCCGGCG | TGGTGCTCGG | CGTGGTCTCG | CTGGTGGCGG | TGGTGTGGAT | CAAGGGCGTG | 3360 |
| ATGCGCAAGC | CCCTCTTCGT | ACCCGAACCG | CTCGAGACGG | CCGGTGAGAC | TGCCCAGGGC | 3420 |
| AAGTCCGTCG | CCCTCGATCC | CCTGCAATCC | CTTCGGCCTG | ACGCGCCAAG | GGAACAAGGA | 3480 |
| GAACACAGAC | GATGACCGCT | CAGCTCAACC | CGCAGCGCGA | CACCCGCGAC | TACCAGCAAC | 3540 |
| TGGACGCCGC | GCACCACATC | CACGCCTTCC | TCGACCAGAA | GGCGCTGAAC | CGCGAAAGGC | 3600 |
| CCGCGGGTGA | TGGTCCGCGG | CGATGGCCTG | CAGCTCTGGG | ACAACGACGG | CAAGCGCTAC | 3660 |
| CTGGACGGCA | TGTCCGGCCT | CTGGTGTACC | AACCTCGGCT | ACGGCCGCCA | GGACCTCGCC | 3720 |
| GCCGCCGCCA | GCCGCCAGCT | GGAACAACTG | CCGTACTACA | ACATGTTCTT | CCACACCACC | 3780 |
| CACCCGGCGG | TGGTGGAGCT | TTCCGAGATG | CTCTTCAGCC | TGCTGCCGGA | CCACTACAGC | 3840 |
| CACGCGATCT | ACACCAACTC | CGGCTCCGAG | GCCAACGAGG | TGCTGATCCG | TACCGTGCGG | 3900 |
| CGCTACTGGC | AGATCCTCGG | CAAGCCGCAG | AAGAAGATCA | TGATCGGCCG | CTGGAACGGC | 3960 |
| TACCACGGCT | CGACCCTGGG | CAGCACCGCG | CTCGGCGGGA | TGAAGTTCAT | GCACGAGATG | 4020 |
| GGCGCATGCT | GCCGGACTTC | GCCCACATCG | ACGAACCCTA | CTGGTACGCC | AACGGCGGCG | 4080 |
| AGCTGAGCCC | GGCCGAAGTT | CGGTCGCCGC | GCGGCGCTGC | AACTGGAGGA | GAAGATCCTC | 4140 |
| GAACTGGGCG | CGGAGAACGT | CGCCGCCTTC | GTCGCCGAGC | CCTTCCAGGG | CGCCGGTGGC | 4200 |
| ATGATCTTCC | CGCCGCAAAG | CTATTGGCCG | GAGATCCAGC | GCATCTGCCG | GCAGTACGAC | 4260 |
| GTGCTGCTGT | GCGCCGACGA | AGTGATCGGC | GGCTTCGGCC | GCACCGGCGA | ATGGTTCGCC | 4320 |
| CACGAACACT | TTCGCTTCCA | GCCGGACACC | TTGTCCATCG | CCAAGGGCCT | GACGTCCGGC | 4380 |
| TACATCCCCA | TGGGCGGCCT | GGTACTCGGC | AAGCGCATCG | CCGAGGTGCT | GGTGGAGCAG | 4440 |
| GGCGGGGTGT | TCGCCCACGG | CCTGACCTAT | TCCGGCCACC | CGGTGGCGG | GGCGGTGGCC | 4500 |
| ATCGCCAACC | TCAAGGCTGC | GCGACGAGGG | CGTGGTCACG | CGGGTCAGGG | AGGAGACCGG | 4560 |
| CCCCTACCTG | CAACGCTGCC | TGCGCGAGGT | CTTCGGCGAC | CATCCGCTGG | TCGGCGAGGT | 4620 |

-continued

```
CCAGGGCGCC GGCTTCGTCG CCGCGCTGCA GTTCGCCGAG GACAAGGTGA CCCGCAAGCG    4680
CTTCGCCAAC GAGAACGATC TGGCCTGGCG CTGCCGCACC ATCGGCGGCT TCGAGGAGGG    4740
CGTGATCATC CGCTCCACCC TCGGCCGCAT GATCATGGCC CCGGCGCTGG TGGCCGGGCG    4800
TGCCGAGATC GACGAACTGA TCGACAAGAC CCGTATCGCG GTGGATCGCA CCGCGCGCGA    4860
GATCGGCGTG CTCTGACGCG CCCCGGCGGC CCGGCCTCGG CCGGGTCGCC TGCGACACGG    4920
AGCGTCCCCC CATAACGACG ATGCGGCGCC TGGCGACCGC GCGCGGAACC GTTTCGGCCT    4980
CTGGCGGCAA CTGCCTAAGC AACATCACAA CAATGCCAAT CGGCTGTGGG AGTGTTCCAT    5040
GTTCAAGTCC TTGCACCAGT ACGCACACGT GTTTTCCCGG TTGTCCCTGT TCGTCCTGGC    5100
GTTCGCCGCG GCGGCCCAGG CGCAGAGCCA GAGCCTGACG GTGATCTCCT TCGGCGGCGC    5160
GACCAAGGCC GCCCAGGAAC AGGCCTATTT CAAACCCTTC GAGCGAAGCG GCGGCGGGCA    5220
GGTGGTCGCC GGCGAATACA ACGGCGAAAT GGCCAAGGTG AAGGCCATGG TCGACGTCGG    5280
CAAGGTCAGC TGGGACGTGG TCGAGGTGGA GAGCCCCGAA CTGCTCCGCG GCTGCGACGA    5340
GGGGCTGTTC GAACGCCTCG ACCCGGCGCG TTTCGGCGAC CCCGCGCAGT TCGTCCCCGG    5400
CACTTTCAGC GAGTGCGGGG TGGCCACCTA CGTCTGGTCG ATGGTGATGG CCTACGACTC    5460
GACGAAGCTG GCCAGGGCGC CGCAGTCCTG GCGGATTTTC TGGAACGTCC GCGAGTTCCC    5520
CCGGCAAGCG TGGCCTGCGC AAGGGCGCCA AGTACACCCT GGAAGTGGCG TTGCTGGCCG    5580
ACGGGGTGAA GGCGGAGGAC CTCTACAAGG TACTCGCCAC CCCGGAGGGG GTCAGCCGCG    5640
CCTTTCGCCA AGCTCGACCA GCTCAAGCCG AACATCAGT GGTGGGAGGC CGGCGCCCAG    5700
CCGCCGCAAT GGCTGGCGGC CGGCGACGTG GTGATGAGCG CGGCCTACAA CGGGCGCATC    5760
GCCGCTGCGC AGAAGGAGGG GGTGAAACTG GCCATCGTCT GGCCCGGCAG TCTCTACGAT    5820
CCGGAGTACT GGGCGGTGGT GAAGGGCACC CCGAACAAGG CGCTGGCGGA GAAATTCATC    5880
GCCTTCGCCA GCCAGCCGCA GACGCAGAAG GTGTTCTCCG AGCAGATCCC CTACGGGCCG    5940
GTACACAAGG GCACCCTGGC GTTGCTGCCG AAGACGGTGC AGGAGGCGCT GCCGACCCGC    6000
GCCGGCCAAC CTCGAAGGCG CGCGGGCGGT GGATGCCGAG TTCTGGGTGG ACCACGGCGA    6060
GGAGCTGGAA CAGCGTTTCA ATGCCTGGGC GCGCGCTGAG CGCTGCGCGT CGGCAAAAAA    6120
AATGACGGGC CCCAAGTCGT CCGGGCCCGT CGGGTCAAAG CGCTGACGGG GTGATCAGCG    6180
CAGCTCTTCC AACAACCCCT GCAGATACCG ACAGCCCTCG GTATCCAGCG CCTGCACCGG    6240
AAGGCGCGGC GCCCCCACCT CCAGGCCGGA GAGGCCCAGG CCGGCCTTGA TGGTGGTCGG    6300
CAGGCCCCGG CGGAGGATGA AGTCGAGCAG CGGCAACTGC CGGTAGAACA GCGCGCGGGC    6360
CTTCTCCAGG TCGCCGTCGA GCACCGCCTG GTAGAGCTGG CCGTTGAGCG TCGGGATCAG    6420
GTTCGGCGCG CGCTGCACC AGCCTTTCGC GCCGGCCACG AAGGCCTCCA GCGCCAGCGC    6480
GTTGCAGCCG TTGTAGAAGG GCACCCGGCC TTCGCCGAGC AGGCGCAGCT TGTGCATGCG    6540
CTGGATGTCG CCGGTGCTCT CCTTGACCAT GGTCACGTTG TCCACTTCGC GGACGATGCG    6600
CAGGATCAGT TCCACCGACA TGTCGATGCC GCTGGTGCCC GGGTTGTTGT AGAGCATCAC    6660
CGGCACGCCG ATGGCTTCGC CAACCGCGCG GTAGTGCTGG AACACTTCCG CCTCGTTGAG    6720
CTTCCAGTAG GAGATCGGCA GGACCATCAC CGCCTCGGCG CCGAGGGATT CGGCGAACTG    6780
CGCGCGGCGC ACGGTCTTGG CGGTGGTCAG GTCGGAGACG CTGACGATGG TCGGCACGCG    6840
ATGGGCGACG GTCTTCAGGG TGAAGTCGAC CACCTCGTCC CATTCCGGGT CGCTCAGGTA    6900
GGCGCCTTCG CCGGTGCTGC CGAGCGGGGC GATGGCGTGC ACGCCGCCGT CGATCAGGCG    6960
CTCGATGGAG CGGCCGAGGG CCGGCAGGTC GAGACCGCCG TCGGCGCCGA AGGGGGGTGA    7020
```

| | | | | | |
|---|---|---|---|---|---|
| TGGTGTAGCC | GATGATGCCG | TGGATGGATG | CGGACATTGG | ATGTACCCGT | GACATTGAGT 7080 |
| GGGAAATGCC | AGGACGGACC | TGGTGGGAAA | GGTCGTTCAG | CTCAGGCAGT | CGCTGTTGCG 7140 |
| CGGCAGGCAG | CGCCGGGCGT | AGTAGTTGAA | TGCGGCGCCG | TGGCGCTTCG | GGGTGGAGAT 7200 |
| CCAGTCGTGG | GCCTCGCGCG | CCAGGGCCGG | CGGGATCGGC | TTGATCTCTC | CGGCGGCCAT 7260 |
| CGCCAGCAAC | TGCATCTTCG | CCGCGCGCTC | GAGCAGCACC | GCGATCACGC | AGGCCTCCTC 7320 |
| GATGCTCGCA | CCGGTGGCCA | GCAGGCCGTG | GTGGGAGAGC | AGGATGGCGC | GCTTGTCGCC 7380 |
| GAGGGCGGCG | GAGATGATCT | CGCCTTCCTC | GTTGCCTACC | GGCACGCCCG | GCCAGTCCTT 7440 |
| GAGGAAGGCG | CAGTCGTCGT | ATAGCGGGCA | AAGGTCCATG | TGCGAGACCT | GCAGCGGTAC 7500 |
| TTCCAGGGTC | GACAGCGCGG | CGATGTGCAG | CGGGTGGGTG | TGGATGATGC | AGTTGACGTC 7560 |
| CGGGCGGGCG | CGATAGACCC | AGCTGTGGAA | GCGATTGGCC | GGATTCGCCA | TGCCGTGCCC 7620 |
| GTGGAGGACG | TTGAGGTCTT | CGTCGACCAG | CAGCAGGTTG | CCGGCGCTGA | TCTCGTCGAA 7680 |
| GCCCAGGCCC | AGTTGCTGGG | TGTAGTAGGT | CCCCGCCTCC | GGGCCGCGCG | AGGTGATCTG 7740 |
| CCCGGCGAGC | CCGGAGTCGT | GGCCGGCCTC | GAAGAGAATC | CGGCAGGTCA | GGGCCAGCTT 7800 |
| TTGCCGGTCA | GTCCACGTAT | TATCGCCGAG | GCTGCTTTTC | ATCTGCTTCA | GCGCGTGCTG 7860 |
| GATCAGTTGA | TCCTTGGGTA | ATTCCAGTGT | CGTAACCATG | CGAGGTTCCT | TTGACGGAGC 7920 |
| GAGTCGGGGG | AAACGCCAGG | CAGTTGCGCG | CCACGCAACG | ACCCGGCTGT | AAATGACACG 7980 |
| GATCAAGTTA | TATGACACAA | AGTGTCATTT | AGCAAGAGAG | AAGTTTCATC | GCCATCGGGA 8040 |
| GAAGGCTGTC | CTCAATGTCC | ATGCGCTTGA | AATTGCTGAG | AAAAAAACTC | GGGGTCACGC 8100 |
| TGGAGACCCT | GGCCGACAAG | ACCGGCCTGA | CCAAGAGCTA | CCTGTCCAAG | GTCGAGCGCG 8160 |
| GGCTGAACAC | GCCGTCCATT | GCCGCCGCGC | TGAAGCTGGC | GAAGGCGTTG | AACGTGCAGG 8220 |
| TGGAGGAGCT | GTTCTCCGAG | GAAAGCGACG | GTGTCGACGG | CTACAGCATC | GTTCGTCGCG 8280 |
| ACCAGCGCAA | GTCGCTGTCC | AGCGGCGACG | ACGGCCCGGC | CTACGCCTCC | CTCGTCGCAG 8340 |
| CAGATCGGCG | CCCGCGCGCT | GTTGCCGTTC | ATCGTCCACC | CCCCGCGCGA | TTTCAGTCAC 8400 |
| TCGACGTTCA | AGGAGCACCT | CGGCGAAGAG | TTCATCTTCG | TCCATGAGGG | CCAGGTCGAG 8460 |
| GTCGACTTCA | TGAACCAGCG | GATCATCCTC | GAGCGCGGCG | ACGCCCTGCA | TTTCAACGCA 8520 |
| CAGAAGCCGC | ACCGCATCCG | CTCCCTGGGG | GAGACCCAGG | CGGAATTGCT | GGTGGTGATC 8580 |
| CACAGCGACG | AATGAGGCGA | CGGCTTCGGT | CGATCGGATG | CTTGCTAACG | TTCTGTTCGA 8640 |
| TTATCGAACT | GTTAATCGAT | TATCGGATTG | TGAGCCCTCG | ACCCCGGCG | TAAGGTTCTC 8700 |
| GTCACGTGCC | GTCCAGGCAG | CGCACAACAA | GACGAGACCC | GACCGATGGC | TGAAATCCTC 8760 |
| TCCCTGCGCG | AACGGTGCGA | CGCTTCGTCC | ACGATGGCGA | CAGCGTCGCC | CTCGAAGGCT 8820 |
| TCACTCACCT | GATCCCGACG | NCCGCCGGCC | ACGAGCTGAT | CCGCCAGGGC | AGGAAAGACC 8880 |
| TGACGCTGAT | CCGCATGACT | CCCGACCTGG | TCTACGACCT | GCTGATCGGT | GCAGGCTGCG 8940 |
| CGAAGAAGCT | GGTGTTCTCC | TGGGGCGGCA | ACCCCGGTGT | CGGTTCGCTG | CACCGCCTGC 9000 |
| GCGACGCGGT | GGAGAAGGGC | TCGGCCGCAA | CCGCTGGAGA | TCGAGGAACA | CAGCCACGCC 9060 |
| GACCTCGCCA | ACGCCTATTT | TGCCGGCGCC | TCCGGGCTGC | CCTTCGCGGT | NTGCGCGCCT 9120 |
| ACGCCGGCTC | CGACCTGCCG | AAGGTCAACC | CGCTGATCCG | CAGCGTCACC | TGCCCGTTCA 9180 |
| CCGGCGAAGT | GCTGGCGGCG | GTGCCCTCGG | TGCGTCCGGA | CGTCAGCGTG | ATCCACGCGC 9240 |
| AGAAGGCCGA | CCGCAAGGGC | AACGTGCTGC | TCTGGGGCAT | CCTCGGCGTG | CAGAAGGAAG 9300 |
| CGGCCCTGGC | GGCGAAGCGC | TGCATCGTCA | CCGTCGAGGA | GATCGTCGAC | GAACTGGACG 9360 |
| CCCCGATGAA | CGCCTGCGTC | CTGCCGAGCT | GGGGCGCTCA | GCGCCGTGTG | CCTGGTGCCC 9420 |

| | | | | | |
|---|---|---|---|---|---|
| GGCGGCGCGC | ATCCGTCCTA | TGCCCACGGC | TACTACGAGC | GCGACAACCG | CTTCTACCAG | 9480 |
| GACTGGGACC | CGATCGCCCG | CGACCGCGAA | AGCTT | | | 9515 |

( 2 ) INFORMATION FOR SEQ ID NO:14:

( i ) SEQUENCE CHARACTERISTICS:
        ( A ) LENGTH: 2471 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P2- 7

( x i ) SEQUENCE DESCRIPTION: SEQ ID NO:14:

| | | | | | |
|---|---|---|---|---|---|
| AAGCTTGTTC | CAGGCCCTCG | ACCGCTGCGA | TCTTCTGCGG | GTAGGCGGCG | ATGGTCTGTT | 60 |
| CGGAGTTCGC | CAACTGCAGG | CGACGCTGCG | CCAGCTGCGC | CGCCTGCACG | CCGGCAAGCA | 120 |
| TCAGGTCCTG | ATCGAGCAG | GGGTTGAAGC | CGCGCACGAA | CTCGCTGAAC | TGGTCCACGC | 180 |
| CGAACAGGGT | GGCGATGAGC | TGGCGCTGAT | CGCTCGGGGT | CCGCGCGGCG | ATTCGGGCGA | 240 |
| AATCGTCGAG | GCGGTTCTTC | TCGATGAAGC | AGAAGCGATA | CTCAGCTTCG | TCGGGCTGGA | 300 |
| CGGCCTGCGC | CTCGCCCGCN | GCCGTAGACG | ACAGGACTGG | CGCGATGTGG | CGGCGCAGGC | 360 |
| GAGCGTTGTT | GCAGTACGTC | CGCTGGTCGA | CCGCTTGGCC | TGCGCTTCGC | TGATCGAACC | 420 |
| GAGCATCGCC | ACTTCCAAGG | CTTCGCAGAA | GCTGCTCTTG | CCGGTGCCGT | TGGCACGTNA | 480 |
| GACCAAGGTG | ATGTCATGGC | TGAGGTCGAA | CGTCTCCTGC | CGCATGAATC | CTCGAAACGG | 540 |
| CCCGACTTCG | AGCTGGTGCA | GTCGCCCGAG | CGCCGGCCCG | TTTTCGGGGC | CGCGCGCGTC | 600 |
| CCCGTCGTAG | GCGACAGGCA | TCTGCGCCAA | GATGCGCGAT | GGCCAGCGGC | GCCAAGCCGC | 660 |
| GTGGGAGCGC | CCCCGGCGT | GCAGCACCGA | CCTCGGCCAG | TGGCTGCAGG | TGATCGAGCA | 720 |
| CCAGGGTGCG | CCAGCCGGCG | CACCGTTTCG | TCGTGCACGT | GCCGCTGCGT | CAAGTGCGCC | 780 |
| AGGAACCGGT | GGTACTCCGA | ACGTATGCTT | GCCACAGCGA | CCCCTCACTT | GGTCAACCAC | 840 |
| TGACCGTAAG | CCTCCACATC | GATCATGGGG | ACCGTTCCAC | TGAACTGAAG | CTGCGCGATC | 900 |
| AGCTTGAAAA | GAAACGCGGT | CGCCGGCTTG | TTTTCGTTGG | TGTAGCTGTA | CGCGCCGCTG | 960 |
| GCTTGGTCAT | AGAAAAAGTG | CCCGTGGGCG | GCAACGCATC | CGATGTCCAG | ACGCCCCTCG | 1020 |
| GTGAGGTTTG | CGTTCAGCGC | CTTGTCCATG | GATGGGCCCA | ATGCAGGACT | CCATTCGCTC | 1080 |
| TCGAAGGTGA | GCAAGCCACC | CAGAATCGGA | ATCAACGCTT | CGCTGGGTAG | GTCCCGCCAG | 1140 |
| CGTGCGGGAT | CGGCAGGCTC | GTGCGGTGCA | GCCTGCGCAC | ACTGGCGACC | TTCTCCTGGC | 1200 |
| ATAGCCACAA | GCCCCGCGTC | AGCCGTCTGC | TTGGCCTCGA | ACACGGCGTA | CACGCTTTCG | 1260 |
| GCTGGAATGA | TCGTCTCGTT | CTCGTAGGTG | AAGATAAAAG | GCGAATATTG | CCGATCAAAC | 1320 |
| ACCACCACAT | CGATCTGCTG | GCTGAAGTTC | CCCAGGCTGT | CCACCACATG | CGCCTTCGCC | 1380 |
| GCCTGGTACC | GTTTGGGCAG | ATAGGTATCC | AGCATGTCGA | TCCAGACGTT | CTCGCTCGCA | 1440 |
| TCCCCCTTCG | TACCCGGGTG | ACCGAAGGTC | TTGCGTACTA | CGGACAAGCG | CTGCTGGATG | 1500 |
| TCTTCATGCA | GGGACGACAG | GAGCTGGGAA | AGCGACCACT | GGGACATGCT | GTACCTCGAT | 1560 |
| GGGACGTGTA | TGGAAGCCGA | TGGAATCAGG | ACAGTGGGAA | CTTGGGCCA | AACAGTGCGC | 1620 |
| GCCAGGGCGA | AGCGCTTCGA | TATTGCGACC | ACGACGCGTG | TGGTCGATGG | CGATGCTTGC | 1680 |
| GTCCTGGCTC | GCCTGGAACA | GCAGCTGCTN | GCGNGCGCTG | CTTGCGCGCG | GCATCCATAT | 1740 |
| CGTTGCTGAT | CGCCGGGCCA | AGTCCGGCGG | GATCCGGCCA | CTCGTCATGA | ACACGATCGG | 1800 |

```
CAAGCGTGGC  AAAGAACGAC  TGGATCTCGC  GATCGAACGA  TCCTCCCCAG  CCGCCGTAAA  1860

GACACTCAAG  GGCCATTACC  TCGATCAGGA  ACGAGGGCTT  CACCGGCTTC  TGATCGCCGT  1920

GCTTGGGATT  GTTGTTCCAG  TACTTCACCA  TGCGCACGAG  ACCTTTCCAC  TCATTGCCAT  1980

AGGCTTGGTG  CGCTGCGGTC  GCCTTGTCCT  TATGGATCTC  CGGGTCCGTC  TTGATCCACT  2040

TTCCGGACGC  CGTATCGGGG  ATCTCATACT  GGTCGCCGGT  GTCGAATGCG  GGCACCGCAT  2100

CCACGCTGAC  CACCCGGTAG  TCCGTGTTGT  CCTCCGCGTC  GATGTGAACA  CCGAAATCCA  2160

CGTTGATCGA  GNGCGCCTGT  TTGCGCACGG  CCGCCGAACC  GTATTTCTCC  ACCAATGCAG  2220

AGTGGAAATC  ATCCAGCACT  ACCGATGCGG  CCTTGCCGTG  GTAATGCTTC  TCCGAGTCCT  2280

TCAGCACGAA  GAAGATGTCG  ATATCCTTGA  GCGGCTTCGT  CTTCGTGTAT  CGAGCATAGG  2340

ACCCGGTCAG  GAACTGCGCG  CAATGCCGAA  CTTGGTCTGC  AGGTAGTCCC  GCACTTCGTT  2400

CTGGCGTTGC  GAGGCATTCT  TCTGCTCGCG  TTCGTTGAGT  TCCAGACGCG  ACTTGAACTT  2460

GCGAAAAGCT  T                                                          2471
```

( 2 ) INFORMATION FOR SEQ ID NO:15:

( i ) SEQUENCE CHARACTERISTICS:
        ( A ) LENGTH: 5247 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P2- 17

( x i ) SEQUENCE DESCRIPTION: SEQ ID NO:15:

```
AAGCTTCGAG  GGGGCTGGGC  GAGGATCGAC  CGGCCCCGCT  CGTGTCGGAA  GGGAAGGCCA  60

GGGCTGGCCT  GCCCGTTCGG  CGCTTCGGCA  GGCTGGCGCA  GAACGATGCA  AGGTCGTTCG  120

GGTCAGCATC  AGGGATGAAA  TGACTGACAG  GAGTCGGGAT  GCTGCGTTAC  GTCGTGGGTT  180

TTCTCGCGTT  CACCGTGCTG  GCGGCCTATC  TGTTGCTGGG  GGTTTCCCAG  CACGCCTTCC  240

TGCCGTGACC  GGTCGGCATG  GCGGCTTCAG  CTGCGTTGCG  GAAGAGGCTG  TGGCGGCCGT  300

GCGGGATGCC  GGTTTTCGGC  TTGCCGTGCC  TTGCGTTGCA  GGCGTCGCGC  CGACGCGGCA  360

CGCCAGGGAA  GGCCCACAGG  GTGACGCCGG  CGAGGCCCAG  CCAGGCGACG  ATCAGCAATG  420

TGACGAAGGA  TTCGGGAGTC  ATGGTTCGTC  CTCCTCTTAC  CCAAGGATAG  ACCCTGCGGG  480

AAGGGGAATT  ACTGCAATCG  GTCTTCGACC  ATGGTCTGAA  ACGCGGTCAC  TCGGGGCCGG  540

CGCCGACCAG  GGCCAGGCAG  CCGGTGAGGC  TGGTCAGCAG  GGGCAGGGCG  AGCAGGAAAG  600

CCAGCCAGAT  GGCCTCCATG  CGCAACAGCG  TGGCGCCGAG  GAACAGCGCG  ACCAGGAGGA  660

TGGTCATGAG  CAGGGCGGTC  CAGCCGAAGT  ACATGGCGAA  GTTGTCGATG  CCCAGGCCGA  720

TGCCCCAGCC  CAGCAGCAGG  GCCCATACCC  CGGCCAGAGC  CAGGCCGAGG  GCCAGCATGC  780

TCGCCAGGGT  CCGGGCGGAC  GGGGCATGCA  GCGGGTGGTT  GCGGAATAGC  TCGTAGAAGA  840

TCGGCGTATT  CATCGGCGTC  ACCTCCGCAG  GGAACTTCC   AGCCTAGTCC  AGCGGGCGAG  900

ACGGCCCTAG  ACCTATTTGT  CATTACGAGG  CGTGACCTCA  GGCCGTTAAC  ATCCATCTTT  960

TTCCAGGCGA  TGCCGTGCAT  CGGGCTGCGG  GCCCGCTCAC  CGTTCGTCGC  GCTGAGTCGA  1020

AAAAGAAACC  GAAAGGGTTG  CGTGCATGAG  TTGGCGAACT  CGCCTCGTTC  GAGGTGGATG  1080

GGTATCAACT  GGTCTATCAG  GACCTGGGTG  AAGGCACGCC  GGTGCTACTG  GTCCACGGTT  1140
```

```
CGCTGTGCGA CTACCGCTAC TGGCAATGGC AGTTGCGCAG CTCGGCAAGC ACCACCGGCT 1200
GATCGTGCCG AGCCTGCGTC ACTACTACCC CGAGCGCTGG GACGGGCAGG GTGCGGACTT 1260
CACCAGCGCC CGCCACGTCG CCGACCTGCT GGCGCTGGTC GAGCGGCTCG GCGAGCCGGT 1320
ACACCTGCTC GGCCATTCCC GTGGCGGCAA CCTGGCGTTG CGCCTGGCGC TGGCCGCTCC 1380
GGACGCCCTG CGTTCGCTGA GCCTGGCCGA TTCCGGCGG CGACTATGCC GCCGAGGTCT 1440
ACGCCCACGC CGGCCTGCCT GCGCCCGAGG AACCATTGGA ACGCAACCAG TTCCGGCGCC 1500
AGGCGCTCGA ATTGATCCGT GGCGGCGAGG CGGAACGGGG ACTGGAACTG TTCGTCGATA 1560
CGGTGAGCGG CGCCGGGGTA TGGAAACGCT CGTCGGCGAC GTTCCGCCGA ATGACGCTGG 1620
ACAACGCCAT GACCCTGGTC GGGCAGGTGG CCGACCAGCC GCCGGCGCTG GCGCTGTCGG 1680
AACTGCGCTC GATCGACCTG CCGAGCCTGA TCCTCAATGG CGAACGCAGC CCGCTGCCAT 1740
TCCCGGCCAC CGCCGAGGCG CTGGCGGCGG CCCTGCCGCG CGCCGAGCTG CAACGCATCC 1800
AGGGCGCGTC CCATGGCCTC AATGCCACCC GTCCGGCGGC TTTCAACCGG TCGGTGCTGG 1860
AGTTCCTGGC GCGCGTCGAT GGCGTTGCGC CGGACGTGGA AACGTCCTGA AGCGAGGCCG 1920
GGCGAACTGA CCGCTCGTCA GCTCGCCGCG GATGCTTTAC CATGCGTTCG CGCCGGATCA 1980
GCTCCGGCGT TTTTCGTCAG TATCCATTCC CAGTGATCTC CGTCCGCGCG CTTCGGCGCA 2040
GGGGTGCCGC AAGGCGCCTG CCACTGTGAG GCAGGCCGGC CCGGCGGGCG ACGCTTACTG 2100
GCACATCCCA ACCCACGTGG CCTTTGGTAG GGTCACCACT AGAGAGAGCG CCATGCCCAT 2160
CATTACTCTT CCCGACGGCA GTCAACGTTC CTTCGATCAC CCGGTCTCCG TGGCCGAGGT 2220
GGCCCAATCC ATCGGCGCAG GCCTGGCCAA GGCGACCCTC GCCGGCAAGG TCGACGGCCG 2280
CCTGGTCGAC GCCTGCGACA CCATCGATCG CGACGCGACC CTGCAGATCA TCACGCCCAA 2340
GGACGAGGAA GGACTGGAGA TCATCCGCCA CTCCTGCGCC CACCTGGTCG CCATGCGGT 2400
CAAGCAGCTC TATCCGACCG CGAAGATGGT CATCGGCCCG GTGATCGAGG AAGGCTTCTA 2460
CTACGACATC TTCTTCGAGC GCCCCTTCAC CCCCGAGGAC ATGGCGGCGA TCCAGCAGGC 2520
ATGCGCGAGC TGATCGACAA GGACTACGAC GTGATCAAGA AGATGACCCC GCGCGCCGAG 2580
GTCATCGAGC TGTTCAAGTC CCGTGGCGAA GACTAACAAG CTGCGCCTGA TCGACGACAT 2640
GCCGGACGAG AAGGCCATGG GCCTGTACTT CCATGAGGAG TACGTGGACA TGTGCCGCGG 2700
CCCGCACGTG CCGAACACTC GCTTCCTCAA GGCGTTCCAG CTGACCAAGA TTTCCGGCGC 2760
CTACTGGCGC GGCGACTCGA AGAACGAGCA GTTGCAACGC ATCTACGGCA CCGCCTGGGC 2820
CGACAAGAAG CAACTGGCGG CCTACATCCA GCGCATCGAA GAGGCCGAGA AGCGCGACCA 2880
TCGCCGCATC GGCAAGCAGC TCGACCTGTT CCACCTGCAG GAAGAAGCGC CGGGCATGGT 2940
GTTCTGGCAC CCGAATGCTG GAGCGTCTAC CAGGTGCTCG AGCAGTACAT GCGCAAGGTC 3000
CAGCGCGACC ATGGCTATGT CGAAGTGCGT ACCCCGCAGG TGGTCGACCG CATCCTCTGG 3060
GAGCGTTCGG GCCACTGGTC GAACTACGCC GAGAACATGT TCACCACCTC CTCGGAAAGC 3120
CGCGACTACG CGGTCAAGCC GATGAACTGC CCGTGCCACG TGCAGATCTT CAACCAGGGC 3180
CTGAAGTCCT ACCGCGACCT GCCNTGCGCC TCGCCGAGTT CGGCGCCTGC CACCGCAACG 3240
AGCCGTCCGG CGCGCTGCAC GGATCATGCG GTACGCGGCT TTACCCAGGA CGACGCGCAT 3300
ATCTTCTGCA CCGAAGAGCA GGTGAAGAAG GAAGCGGCCG ATTTCATCAA GCTGACTTGC 3360
AGGTCTACCG CGACTTCGTT TCACCGACAT CGCCATGAAG CTGTCGACCC GTCCGGCCAA 3420
GCGCGTCGGT TCCGACGAGC TGTGGGATCC CGAAGGCGCG CTGGCCGATG CGCTGAACGA 3480
ATCCGGCCTG GCCTGGGAAT ACCAGCCGGG CGAGGGCGCG TTCTACGGGC CGAAGATCGA 3540
```

| | | | | | | |
|---|---|---|---|---|---|---|
| GTTCACCCTG | AAGGACTGCC | TCGGCCGTAA | CTGGCAGTGC | GGCACCCTGC | AGTACGACCC | 3600 |
| GAACCTGCCG | GAGCGCCTGG | ACGCCAGCTA | CATCGCCGAG | GACAACAACC | GCAAGCGCCC | 3660 |
| GGTGATGCTG | CACCGTGCGA | TCCTCGGGTC | CTTCGAGCGC | TTCATCGGCA | TGCTCATCGA | 3720 |
| GCACTACGCC | GGAGCCTTCC | CGGCCTGCTG | GCGCCGACCC | AGGCAGTGGT | GATGAACATC | 3780 |
| ACCGACAAGC | AGGCCGATTT | CGCCGCCGAG | GTGGTGCGGA | TCCTCGGGGA | AAGCGGATTC | 3840 |
| CGTGCCAAGT | CCGACTTGAG | AAACGAGAAG | ATCGGCTTTA | AAATCCGCGA | GCATACTTTG | 3900 |
| CTCAAGGTTC | CCTATCTCTT | GGTTATTGGA | GATCGGGAAG | TTGAATCGAA | GGCCGTCGCG | 3960 |
| GTGCGTACGC | GCGAAGGGGA | AGACCTGGGC | TCCATGCCCG | TCACCCAGTT | CGCTGAGCTG | 4020 |
| TTGGCACAGG | CGGTTTCCCG | GCGTGGTCGC | CAAGACTCGG | AGTAATCATT | ATTAAGCGTG | 4080 |
| AAATGAGACA | GGATAAGCGA | GCTCAACCGA | AACCCCGAT | CAACGAGAAC | ATCTCGGCTC | 4140 |
| GTGAGGTACG | GTTGATTGGA | GCTGATGGCC | AGCAGGTTGG | TGTTGTTTCG | ATCGATGAGG | 4200 |
| CGATCCGCCT | AGCCGAAGAG | GCGAAGCTGG | ACCTGGTTGA | GATTTCGGCC | GACGCGGTGC | 4260 |
| CTCCTGTCTG | CCGCATCATG | GACTACGGCA | AGCACCTGTT | CGAGAAGAAG | AAGCAGGCTG | 4320 |
| CGGTCGCCAA | GAAGAACCAG | AAGCAGGCGC | AGGTCAAAGA | AATCAAGTTT | CGTCCAGGGA | 4380 |
| CGGAAGAAGG | GGATTACCAG | GTAAAACTAC | GCAACCTGGT | ACGTTTCCTT | AGTGAAGGGG | 4440 |
| ACAAGGCCAA | GGTATCCCTG | CGATTCCGCG | GCCGTGAGAT | GGCTCACCAG | GAGCTGGGGA | 4500 |
| TGGAGCTGTT | GAAGCGGGTC | GAAGCCGACC | TCGTGGAGTA | CGGCACCGTC | GAGCAGCATC | 4560 |
| CTAAGCTGGA | AGGACGCCAG | CTGATGATGG | TCATCGCTCC | CAAGAAGAAA | AAGTAACCAC | 4620 |
| CAGGGCACTG | GCAGGCCTTG | CGGTTATGCG | TAATCACTCA | ATGCGGAGTA | TCCGAACATG | 4680 |
| CCAAAGATGA | AGACCAAAAA | GTGGGCGCGG | CCAAGCGCTT | CAAGAAGACT | GCTGGTGGCC | 4740 |
| TCAAGCACAA | GCACGCCTTC | AAGAGCCACA | TCCTGACCAA | GATGACCACC | AAGCGTAAGC | 4800 |
| GTCAACTGCG | CGGCACCTCG | ATGCTGAACA | AGTCTGACGT | TGCGCGCGTA | GAACGCTCCC | 4860 |
| TGCGTCTGCG | CTGATTATTA | AGGTAGAGGA | TTAATTCATG | GCTCGTGTTA | AGCGTGGCGT | 4920 |
| TATCGCCCGT | CGTCGTCACA | AGAAAATTCT | GAAGCTCGCC | AAGGGCTACT | ACGGTGCACG | 4980 |
| CTCGCGCGTG | TTCCGCGTTG | CCAAGCAGGC | GGTGATCAAG | GCTGGCCAAT | ACGCCTACCG | 5040 |
| TGACCGTCGT | CAGCGCAAGC | GTCAGTTCCG | CGCACTGTGG | ATCGCCCGTA | TCAACGCTGG | 5100 |
| TGCTCGTCAG | AACGGTCTGT | CCTACAGCCG | CCTGATCGCC | GGCCTGAAAA | AGGCGGCCAT | 5160 |
| CGAGATCGAC | CGTAAGGTCC | TGGCCGATCT | GGCAGTGAAC | GAAAAAGCGG | CGTTTACCGC | 5220 |
| GATTGTCGAG | AAAGCGAAGG | CAAGCTT | | | | 5247 |

( 2 ) INFORMATION FOR SEQ ID NO:16:

( i ) SEQUENCE CHARACTERISTICS:
        ( A ) LENGTH: 2812 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P4- 5

( x i ) SEQUENCE DESCRIPTION: SEQ ID NO:16:

| | | | | | | |
|---|---|---|---|---|---|---|
| AAGCTTTGGT | GATCTTAACG | TGACAAGCTC | CTTAGAAAAA | TTTTATGAGT | TTATTAGCGG | 60 |
| GGTCTTTCTT | GATCCGACTG | TACCAAGACT | TTCAACTCGT | AAAATACGCA | AGCACAAAAG | 120 |
| CACTGAAATG | CACTCTGCAC | GTTTGTCGCC | GTCCACGGTA | GCGGCATCCC | TCAATCACAC | 180 |

```
CGAAGCGGTG  AATCTTTCTA  CCTATGCAGA  GGCAACACCT  GAACAGCAGC  AATCCGAGTT   240
CAGCCTGTTT  TGGGATGCAA  TACGCCACGC  TGCTCATGTT  GTGCGTGAGC  GAAGCCGCAA   300
GGCTGTAGCA  AGTAGTGTCG  CAATAGCGGC  GGGTCACTGC  GAGGATTTCA  ATAAGCCGAC   360
GTCTGCCACT  GATGTGGGAT  TGATTATAGA  GCCGAACTGC  CGCACCCAAT  ATGGTTGTTT   420
GTACTGCGAA  AACTATTTAT  GTCACGGCGA  TGAGGAGGAT  CTGCATAAAA  TTCTGAGTTT   480
GCAATACGTG  GTCAATGCCG  TGCGTAAATC  GGCCCCCGAT  GCAGCGCATA  CTGAGGCACT   540
TTTCAAAGAG  TTATCTATCC  GGATCGAGTT  TATAGTCGAT  GCTCTTAGTG  AGCGCTCTAG   600
CTCGGTGAAA  CAGACAGTCG  AAAAGGTTAA  AGCTAAGGTG  TTTGAATACG  GCGAGTTAAC   660
TAAGTTTTGG  GAAGTCCGGT  TGGGTCGCTA  TGAAAAATG   GGGATCGTAT  TTGAGTGCT    720
GCTGTTCAGT  CGATAGGTAG  TCTTTTTTCT  AGCGGCCAGT  TTCCAGTCAC  CAGCCAGCCA   780
GATAGTGCGG  CTCAGCTGTA  TGGGAAGCCC  GCGTCGGATT  TTGTTATCTG  TCGCACTGAG   840
TATGGCAATG  CAACGGCAGT  GTACGGCGAG  TCTGTATGGG  ACTTTAACCC  GTACAGGCTG   900
AGTGCAAAAA  AAATTGGCCG  AATACGCTTC  GATATGGTGT  TCGGTGATTA  TGGTCATGAT   960
CAGCAAGCGC  TGATCGAAGA  AGCCAAATAT  CTTCTGTATT  GTCTTATTTA  TTTCGCTGGC  1020
GGTGGGCGGA  TTGGTAAGCT  GAGTGCATCT  ACGATTATTT  CATATTGGGT  TGTGCTGCGC  1080
ATCGCTATGA  AGTTCTGCTA  TGCGCAGAAA  AAGAAGTCAA  TGGTTGGTGT  GCTGTCCTTG  1140
CAGCAGCTTT  TTACCGTGCC  TGTTTATCTA  GCGGCTTTTG  TTAGTGAAAG  TAATTTTGAC  1200
AAGACGGTTC  TTAGTGGGAT  ATTGCACGGA  TTGATTAGTG  TGGGCGAGGA  ACGCCTAGGG  1260
TATGTTGTGC  TGAATCCAAG  AGTTTTTGAT  TTGAGAAGAC  CTGATTCTAA  ACAGCATTCC  1320
GGTAATTCCG  ACACGCCTTT  ATTTGAATTT  AATAATATTG  TGGCGACCTG  CTCGATCATC  1380
TTACTTGGGT  GTTGGGAATA  TTGATTCATT  TATATCGTGC  TTTGCTGATG  AGTATTTCGG  1440
TCTTACTCCG  CACCGTCAAA  AATCTTTGGG  GGTTGGTGGT  AAGTCGCGCT  ATCGCCCCGG  1500
TATTCAGCAA  GCAATAGAGG  AATATGGTCT  GGCTGCGGTT  TTTGTCGGTG  AGTTTGCCTG  1560
TTCCGAAAAG  AGAAAGCTGC  AGCGAGTCCT  TCTCAAGATG  CAGTATGTGG  TGAGAATGGT  1620
GATACACCTA  TATACCGGCA  TGCGTGATCA  AGAGGTGATG  CGTATGTCTT  ATAACTGCTT  1680
ATCTGATCAA  GTCGTGAGAT  GTTCAGTGGT  TGATGATCAA  GGTTTTATGC  GCGATCAACC  1740
GCAATCAGTA  CACATATTAT  CGACTACCAC  GAAGTTTAGC  GGTTACAAGA  AAGAAAGCGC  1800
ATGGTTCGCG  GCAGGCGAAG  TCGTCAAGGC  GGTCGAGGTT  GGCCAGGCGA  TTTGTCGTGG  1860
TTTAGCCCGG  CTCTATAGGA  TTGAACTGGA  TGATCGTTGT  CCGCTATTCA  TCAATCCGTC  1920
CGTCCTGTGT  AAAACGAAGA  ATTGTGCAGA  AGTTGGTGTA  ACAGACTTTA  CATTGAGAGC  1980
AACGATGGCA  GTGCTTTGAA  ATCCTTATCG  ATTCAATCAG  AGGATTTACA  AGAGTTGGCT  2040
CAGAGCGACC  CTTCTCGTGA  CTTTTACAAT  GAGCCAGATT  TTGCAGTAGG  CCAGCCCTGG  2100
CCGCTGACTA  GCCATCAATT  CCGACGTTCG  TTGGCCTTCT  ATGGAAGCAG  TAGCGGCTTT  2160
CTCTCGTTAC  CGACTCTGCG  AGCGCAGTTC  AAGCATATGA  CCCATTCAGA  TGGCGCGCTA  2220
TTATGCGAAT  GGCTTTGATA  ACTTGCGCAC  CATTTTTGGC  TACTATGACG  AGAAGAAAAT  2280
AGACTTCGTG  CTACCATATA  ACCACTTTGC  TTTCGAGTTC  CAGATGGCCA  TGCCGATGTC  2340
GGTGGCCAAT  CAGTTGATTG  CAGATCTGCT  GTTCAAAGAA  GAACCGCTGT  TTGGTGGCAC  2400
CGGTTCATAC  ATGCAGAGGC  AGAAAGAACG  TGTTGAAGCT  GGCGAGATAA  AGATTGAAGA  2460
TATTCGTGCC  GATACAGAGC  TTCGGGTGAA  GAACGGTGCA  ATTAGCTATC  GGCCAACGCT  2520
ACTCGGTGGT  TGCACCAAGG  TGGGCCGCTG  CGATTCCTTC  ATGCTCGGTG  ACTATACTGA  2580
```

| ATGTTTGTCC | TGCGAGGGTG | CGATTATCAA | GCCCTCCAGG | TTAAGTGCGG | CCATTGAGGA | 2640 |
| ---------- | ---------- | ---------- | ---------- | ---------- | ---------- | ---- |
| TGCGAAAAAC | GAGTTGTCAA | ACTACGCAGA | AGACTCAGGC | GAATATCAAA | TTGTGAAGGG | 2700 |
| CGATATTGAG | CGCCTAATGG | TTTTCAAGAC | TCGCCTGATC | GACACTGTGG | AGCTTTAGTC | 2760 |
| ATGAAGTCTG | GTGAAGGAAT | AAGCAAGGGG | GTTGGTGCCT | GTCAGGAAGC | TT         | 2812 |

( 2 ) INFORMATION FOR SEQ ID NO:17:

( i ) SEQUENCE CHARACTERISTICS:
        ( A ) LENGTH: 3615 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Escherichia coli
        ( B ) STRAIN: Clinical Isolate EC- 24

( x i ) SEQUENCE DESCRIPTION: SEQ ID NO:17:

| AAGCTTTTCT | TGCGTGTTCT | TGTGAGGCTT | CCTTCGCCAT | TATCATCACG | ATCCACATAA | 60   |
| ---------- | ---------- | ---------- | ---------- | ---------- | ---------- | ---- |
| ATAAAGCCGT | AGCGCTTAGA | CATTTGTGAA | TGAGATGCAC | TGACTAAATC | AATTGGCCCC | 120  |
| CAACTGGTGT | ACCCCATAAT | ATCCACACCA | TCGGCAATCG | CTTCATTTAC | CTGTACCAGG | 180  |
| TGATCGTTTA | AATAGGCAAT | TCGATAATCG | TCCTGTATCG | AACCATCCGC | TTCAACGCTG | 240  |
| TCTTTTGCGC | CTAATCCGTT | CTCGACAATA | AATAACGGTT | TTTGATAACG | ATCCCAAAGC | 300  |
| GTATTTAACA | GAACCCGTAA | TCCAACCGGA | TCAATTTGCC | ACCCCACTC  | TGAACTTTTC | 360  |
| AGATGCGGAT | TGGGGATCAT | ATTCAGTATG | TTGCCCTGCG | CATTTTTATT | AATGCTTTCG | 420  |
| TCGTGGGAAC | ACAACCAGTC | ATGTATAACT | AAAGAGATGA | ATCGACGGTA | TGTTTTAAAT | 480  |
| CTCTGCGTCA | CTTTCAGTCA | TCTCAATGGT | GATATTGTGG | TCGCGGAAGA | AACGCTGCAT | 540  |
| ATAGCCGGGA | TACTGGCCAC | GCGCCTGAAC | ATCACCAAAG | AACATCCAGC | GCCGGTTCTC | 600  |
| TTCCATGGCC | TGCAACATAT | CCTGTGGCTG | GCAGGTGAGG | GGGTAAACCA | GCCCACCGAG | 660  |
| AAGCATATTG | CCGATTTTCG | CTTCGGGGAG | CAGGCTATGA | CAGGCTTTAA | CTGCCCGCGC | 720  |
| ACTGGCAACC | AGTTGATGGT | GGATAGCCTG | ATAAACTTCC | GCCTCGCCAC | TCTCTTCTGC | 780  |
| CAGCCCCACG | CCCGTGAATG | GCGCGTGTAA | CGACATGTTG | ATTTCATTAA | ACGTCAGCCA | 840  |
| TAACGCCACT | TTATGTTGGT | AGCGAGTAAA | GACCGTGCGG | GCGTAATGTT | CGAAGTGATC | 900  |
| GATGACCGCT | CGATTAGCCA | ACCGCCGTAG | TTTTTCACCA | GCCCATATGG | CATTTCGTAA | 960  |
| TGGGATAACG | TTACCAGCGG | CTTGATCCCC | GCCTGCGCCA | TTTCATCAAA | CAGCCGATCG | 1020 |
| TAAAACGCTA | ACCCGCTTC  | ATTCGGTTCG | ACTTCGTCGC | CCTGAGGGAA | AATTCGCGCC | 1080 |
| CAGGCAATGG | AAATACGCAG | ACAGGTGAAG | CCCATCTCGG | CAAATAACGC | GATATCTTCC | 1140 |
| GGGTAACGGT | GATAAAAATC | GATGGCGACA | TCTTTGATAT | TCTCTTTCCC | CAGGATGCGC | 1200 |
| GGTTCCATTT | TTCCCATTAC | GCATGAGGCT | GTAAATCTGA | GGTCGAGATC | CCTTTGCCAT | 1260 |
| CTTCCTGCCA | GGCACCTTCC | ACCTGATTGG | CAGCTGTTGC | GGCACCCCAA | AGAAATGTTT | 1320 |
| CTGGAAATGC | TTTCATAATT | AACTCCTTTT | ATCGTTAGCG | AATGATGGAT | AACAGCGGTT | 1380 |
| CACCTGCGCT | TATCTGCGCC | GTGCCGTGGG | GTAATACGTC | CGTAAAATCA | TCGCTATTAC | 1440 |
| TGATTAATAC | CGGCGTCGTC | AGATCAAATC | CGGCCTCGCG | AATAGCAGGG | ATATCAAAAG | 1500 |
| AAATCAGCCG | ATCGCCTGTA | TTGACCTTGT | CACCCACGTT | GACGTGAGCG | GAAAAGAATT | 1560 |
| TGCCGTCCAG | TTTTACGGTG | TCGATACCGA | CATGAATCAG | GATCTCCACA | CCATCATCTG | 1620 |

| | | | | | | |
|---|---|---|---|---|---|---|
| ACTCAATGCC | AATGGCGTGT | AATGTGGCGA | ACAACGAAGC | AATTCGACCC | GCAACCGGAG | 1680 |
| AACGCACTTC | ACCAACCGAG | GGCAGAATGG | CAATACCTTT | ACCCAACAGG | CCACTGGCAA | 1740 |
| ACGTGGTATC | AGCGACGTGA | ATGAGCGACA | CAATCTCTCC | CGTCATCGGT | GAACAGATAC | 1800 |
| CGCCCTGCTC | AGGTGGTGTA | ATAACCTCTG | GTGTTTTCTC | TTCGGGCAC | CCTGCGCTGG | 1860 |
| CTGACGTTTA | GCGGTGATGA | AATGAAGCAT | CACCGTACCG | ACAAATGCGC | AACCGATGGC | 1920 |
| AATGACACCG | CCAATAACGC | TGGCCCAGAC | GGTGAAATCA | ATTCCCGTTG | ACGGGATGGT | 1980 |
| TTGCATGAAG | GTGAAAATAC | TTGGCAAACC | AAAGGAGTAG | ACTTTCGTTT | GCGCGTAGCC | 2040 |
| AATAATGGTG | GCCCCAAAG | CCCCACTGAT | ACAGGCGATA | ACAAGGGGT | ACTTACGCGG | 2100 |
| CAGGTTGACG | CCATATACCG | CTGGTTCGGT | GATACCAAAC | AGACTCGTCA | ACGCCGCTGA | 2160 |
| TCCCGCCACC | ACTTTTTTCT | GCGCATCGCG | TTCGCAGAGG | AAGACGCCGA | GCGCCGCCCC | 2220 |
| GACCTGCGCC | ATAATGGCGG | GCATTAACAG | CGGGATCATG | GTGTCGTAGC | CCAGCACGGT | 2280 |
| GAAGTTATTG | ATACACACCG | GCACCAGGCC | CCAGTGCAGT | CCGAACATGA | CGAAGATTTG | 2340 |
| CCAGAAGCCG | CCCATTACCG | CGCCCGCAAA | TGCAGGAACC | GCCTGATAAA | GCCAGAGATA | 2400 |
| ACCGGCGGCA | ATCAGTTCGC | TTATCCAGGT | TGATAGCGGC | CCCACCAGCA | GAAAGGTGAC | 2460 |
| GGGTGTGATA | ACCATCAGAC | ATAGCAATGG | TGTGAAGAAA | TTTTTGATTG | CCGACGGTAA | 2520 |
| CCACGCATTA | AGTCGGCGTT | CCAGAATGCT | GCACAACCAG | GCAGAAAAAA | TAATGGGAAT | 2580 |
| AACCGATGAC | GAGTAATTCA | ACAATGTGAC | CGGAATACCC | AGGAAATCCA | GCCCAGCGC | 2640 |
| ATCCGCTTTT | GCGCGTTCTC | GAAAAGCAGT | ACAGAATTAA | TGGATGCACT | AACGCTCCAC | 2700 |
| CAATCACCAT | GGCAGTAAAT | GGATTATCGC | CGAAGCGTTT | CCCCGCGGTG | TATCCCAGGA | 2760 |
| TTATCGGGAA | GAACCAAAAC | AAGGCATCAC | TGGCGCTGAA | TAAAATTAAA | TAAGTACCAC | 2820 |
| TTTGTTCGGG | CGTCCACTGA | AAAGTGAGCG | CCAGAGCCAG | CATACCTTTC | AAGATCCCCG | 2880 |
| GTTGCCCGCC | ATCAAACCGA | TACAGAGGCG | TAAAAATACC | TGAAATAACA | TAAACAAAGC | 2940 |
| GGTTTAGACA | GATTACCTTT | ATCATACATT | TTCCGGTGCC | TGTTGCGCTT | TTTCGTCAAG | 3000 |
| GCCTGCCACA | CTGTTAACCG | CCAGGAAGAC | ATCGGCCACA | TGGTTACCTA | TGACCACCTG | 3060 |
| AAACTGGCCA | CCGCTTTCCA | CCACCATAAT | AATACCGGGG | GTCTTTTTCA | GTACCTCTGC | 3120 |
| TTGCGCTTTG | CTTTCATCCT | TTAATTTAAA | AACGTAAATC | GCGTTGCGCA | ATGCATCAGA | 3180 |
| CTCACAATGT | TATCTGCGCC | CCCGACTCCT | GCGACTATTT | TTCTGGCTAA | CTCCGTCATA | 3240 |
| ACTTGCCCTC | TACGCTTTGC | GGCAAAACTC | CAAAAAAAA | CCTGAAAAAA | ACGGCCTGAC | 3300 |
| GTGAATCAAG | CAATTTTTTT | CAGGTTTTGC | CCGCTTAGTG | CGGTAACAAT | CCTTTACTCA | 3360 |
| GTAATAATAT | TTCAGTGTTC | TTTGCGCACG | CGCTCTATAT | TTATGGCTAA | AAACATAATC | 3420 |
| TCTGCGGGTG | AAATTTTACG | TTGATACTGC | AAACCAATAA | AAATGGCGAT | CCGTTCCGCA | 3480 |
| CATTGCCATG | CTTGCGGGTA | ATTTTGTTTT | ACTGCTTGTT | GTAATGATTC | ATCACTATCG | 3540 |
| TTAATTGAAG | CATGTTCAAG | AATACGCCAG | GATAAAAACT | TCAGATGTGT | AACCAGTCGC | 3600 |
| TGATAACTCA | AGCTT | | | | | 3615 |

( 2 ) INFORMATION FOR SEQ ID NO:18:

( i ) SEQUENCE CHARACTERISTICS:
        ( A ) LENGTH: 4954 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:

( A ) ORGANISM: Escherichia coli
( B ) STRAIN: Clinical Isolate EC- 34

( x i ) SEQUENCE DESCRIPTION: SEQ ID NO:18:

| | | | | | | |
|---|---|---|---|---|---|---|
| AAGCTTAACC | GCTCTCATCT | GTTGACCGCA | CGGCATAGCT | ATATTCTGCC | GGTCCTGGGA | 60 |
| CGTAGCGAGA | TTGACATGCA | AAAAAACGGT | GCGCAGGCGG | TAACCGTTGA | GGATTCAATG | 120 |
| TCGATGATTC | ATGCCTCGCG | TGGCGTGTTA | AAACCCGCCG | GTGTAATGCT | GAAATCAGAG | 180 |
| TGTGCAGTGG | TCGCGGGAAT | CGCGCAGGCA | GCACTACCCC | AGAGCGTGGT | AGCCTGGGAG | 240 |
| TATCTGGTGG | AAGATTATGA | TCGCATTCGC | AATGACATTG | AAGCTGTGCT | GCCAGAGTTC | 300 |
| GCCGACTATA | ACCAGCGCAT | CCGTCATCCC | GGTGGTTTTC | ACCTGATAAA | TGCAGCTGCT | 360 |
| GAAAGGCGCT | GGATGACGCC | GTCAGGTAAG | GCTAATTTCA | TTACCAGCAA | AGGGCTGTTA | 420 |
| GAAGATCCCT | CTTCAGCGTT | TAACAGTAAG | CTGGTCATGG | CGACAGTACG | CAGCCACGAT | 480 |
| CAGTACAACA | CGACGATTTA | TGGTATGGAT | GATCGCTATC | GAGGGGTATT | CGGTCAACGA | 540 |
| GATGTGGTCT | TTATGAGTGC | TAAACAAGCT | AAAATTTGCC | GTGTAAAAAA | CGGCGAAAGA | 600 |
| GTTAATCTTA | TTGCGCTTAC | GCCAGACGGT | AAGCGCAGTC | ACGCCGCATG | GATAGATTAA | 660 |
| AAGTGGTCAT | TTACCCTATG | GCTGACCGCT | CACTGGTGAC | CTATTTTCCA | GAATCGAATC | 720 |
| ACATGCTAAC | ACTTGATAAC | CACGATCCAT | TAAGTGGCAT | TCCTGGCTAT | AAAAGTATTC | 780 |
| CGCTTGAATT | AGAACCATCA | AATTAATGTC | TCTTCTCATT | TCTTCTGCTG | TCATCCGCAC | 840 |
| AGCAGAAGAA | TTCCTCATTG | ACTATTATTT | CGCAATTTGC | TCACATGGAT | TAAATTAAAC | 900 |
| TACATACTAT | AAGATATAAA | CTTCTGCCTA | CAGCTGTAAG | AAACTCCGCT | CAGTACTGAA | 960 |
| GCACCAGTCC | TATTTCCTCT | TTTCTCCAGC | CTGTTATATT | AAGCATACTG | ATTAACGATT | 1020 |
| TTTAACGTTA | TCCGCTAAAT | AAACATATTT | GAAATGCATG | CGACCACAGT | GAAAAACAAA | 1080 |
| ATCACGCAAA | GAGACAACTA | TAAAGAAATC | ATGTCTGCAA | TTGTGGGTGT | CTTATTACTG | 1140 |
| ACACTTACGT | GATAGCCATT | TTTTCGGCAA | TTGATCAGCT | GAGTATTTCA | GAAATGGGTC | 1200 |
| GCATTGCAAG | AGATCTTACA | CATTTCATTA | TCAATAGTTT | GCAAGGCTGT | AAACAAACAG | 1260 |
| CAAATTATAA | ATATGAAATG | TTAAAAAAGT | ATCGATAAAA | ACTTATTGT | TTAAGGAGA | 1320 |
| TAAAATGTCG | CTCGTTTGTT | CTGTTATATT | TATTCATCAT | GCCTTCAACG | CTAACATTTT | 1380 |
| AGATAAAGAT | TACGCCTTCT | CTGACGGCGA | GATCCTGATG | GTAGATAACG | CTGTTCGTAC | 1440 |
| GCATTTTGAA | CCTTATGAGC | GGCATTTTAA | AGAGATCGGA | TTTACTGAAA | ATACCATTAA | 1500 |
| AAAATATCTA | CAATGCACTA | ACATCCAGAC | AGTGACGGTG | CCTGTTCCTG | CGAAGTTTTT | 1560 |
| ACGTGCTTCA | AATGTACCGA | CTGGATTGCT | TAATGAAATG | ATTGCTTATC | TCAACTCGGA | 1620 |
| AGAACGCAAT | CATCATAATT | TTTCAGAACT | TTTGCTTTTT | TCTTGCCTGT | CTATTTTTGC | 1680 |
| CGCATGCAAA | GGTTTCATTA | CACTATTAAC | TAACGGTGTG | CTATCCGTTT | CTGGGAAAGT | 1740 |
| GAGAAATATT | GTCAACATGA | AGCCGGCGCA | CCCATGGAAG | CTGAAAGATA | TTTGTGACTG | 1800 |
| CCTGTACATC | AGTGAAAGCC | TGTTGAAGAA | AAACTTAAGC | AAGAGCAAAC | GACATTCTCA | 1860 |
| CAGATTCTTT | TAGATGCAAG | AATGCAGCAC | GCAAAAATT | TGATACGCGT | AGAAGGTTCA | 1920 |
| GTCAATAAAA | TTGCCGAACA | ATGTGGTTAT | GCCAGTACAT | CTTATTTTAT | TTATGCGTTC | 1980 |
| CGCAAACATT | TCGGCAACAG | TCCGAAGAGA | GTTTCTAAGG | AGTACCGTTG | TCAAAGTCAC | 2040 |
| ACGGGTATGA | ATACGGGCAA | CACGATGAAT | GCTTTAGCTA | TTTGATTATT | TGCTAACGAG | 2100 |
| TAGTCAACCA | CACACGCTGC | GTAAGAATTA | AATGGGGCAG | CCATTCCCTG | CCCCGCGTTG | 2160 |
| TTTTTAGGCG | ATATATTTAT | TGAAATAAAT | AAGTGACATC | CATCACATAT | TTATGCACTT | 2220 |
| GCATAACCTG | TTGCATGATT | ATTTATGATC | TCAATTCTGC | ATTTTGTCAG | TAAAATGCAA | 2280 |

```
TAATTTATTA  AATATCAATA  AATTAGTTGT  TTATCGGCGA  GAAATTACTT  AATAGAACAG   2340

AAAGTAATGT  CAACGCTTTA  TGGACTGTTT  TTTCCCTTTT  TTTAGCTAAA  TCTGCTATCT   2400

CTTTATGTGA  CTAACTTCAC  TTACATCCAC  TTATTTCTCT  TCGTAAAATT  ACTTTGGAAT   2460

TAAGTACAAT  AAGAAGAGGA  ACATTTATGA  AGTCTGCATT  AAAGAAAAGT  GTCGTAAGTA   2520

CCTCGATATC  TTTGATACTG  GCATCTGGTA  TGGCTGCATT  TGCTGCTCAT  GCGGCAGATG   2580

ATGTAAAGCT  GAAAGCAACC  AAAACAAACG  TTGCTTTCTC  AGACTTTACG  CCGACAGAAT   2640

ACAGTACCAA  AGGAAAGCCA  AATATTATCG  TACTGACCAT  GGATGATCTT  GGTTATGGAC   2700

AACTTCCTTT  TGATAAGGGA  TCTTTTGACC  CAAAAACAAT  GGAAAATCGT  GAAGTTGTCG   2760

ATACCTACAA  AATAGGGATA  GATAAAGCCA  TTGAAGCTGC  ACAAAAATCA  ACGCCGACGC   2820

TCCTTTCATT  AATGGATGAA  GGCGTACGTT  TTACTAACGG  CTATGTGGCA  CACGGTGTTT   2880

CCGGCCCCTC  CCGCGCCGCA  ATAATGACCG  GTCGAGCTCC  CGCCCGCTTT  GGTGTCTATT   2940

CCAATACCGA  TGCTCAGGAT  GGTATTCCGC  TAACAGAAAC  TTTCTTGCCT  GAATTATTCC   3000

AGAATCATGG  TTATTACACT  GCAGCAGTAG  GTAAATGGCA  CTTGTCAAAA  ATCAGTAATG   3060

TGCCGGTACC  GGAAGATAAA  CAAACGCGTG  ACTATCATGA  CACCTTCACC  ACATTTTCTG   3120

CGGAAGAATG  GCAACCTCAA  AACCGTGGCT  TTGATTACTT  TATGGGATTC  CACGCTGCAG   3180

GAACGGCATA  TTACAACTCC  CCTTCACTGT  TCAAAAATCG  TGAACGTGTC  CCCGCAAAAG   3240

GTTATATCAG  CGATCAGTTA  ACCGATGAGG  CAATTGGCGT  TGTTGATCGT  GCCAAAACAC   3300

TTGACCAGCC  TTTTATGCTT  TACCTGGCTT  ATAATGCTCC  GCACCTGCCA  AATGATAATC   3360

CTGCACCGGA  TCAATATCAG  AAGCAATTTA  ATACCGGTAG  TCAAACAGCA  GATAACTACT   3420

ACGCTTCCGT  TTATTCTGTT  GATCAGGGTG  TAAAACGCAT  TCTCGAACAA  CTGAAGAAAA   3480

ACGGACAGTA  TGACAATACA  ATTATTCTCT  TTACCTCCGA  TAATGGTGCG  GTTATCGATG   3540

GTCCTCTGCC  GCTGAACGGG  GCGCAAAAAG  GCTATAAGAG  TCAGACCTAT  CCTGGCGGTA   3600

CTCACACCCC  AATGTTTATG  TGGTGGAGAA  GGAAAACTTC  AACCCGGTAA  TTATGACAAG   3660

CTGATTTCCG  CAATGGATTT  CTACCCGACA  GCTCTTGATG  CAGCCGATAT  CAGCATTCCA   3720

AAAGACCTTA  AGCTGGATGG  CGTTTCCTTG  CTGCCCTGGT  TGCAAGATAA  GAAACAAGGC   3780

GAGCCACATA  AAAATCTGAC  CTGGATAACC  TCTTATTCTC  ACTGGTTTGA  CGAGGAAAAT   3840

ATTCCATTCT  GGGATAATTA  CCACAAATTT  GTTCGCCATA  CAGTCAGACG  ATTACCCGCA   3900

TAACCCCAAC  ACTGAGGACT  TAAGCCAATT  CTCTTATACG  GTGAGAAATA  ACGATTATTC   3960

GCTTGTCTAT  ACAGTAGAAA  ACAATCAGTT  AGGTCTCTAC  AAACTGACGG  ATCTACAGCA   4020

AAAAGATAAC  CTTGCCGCCG  CCAATCCGCA  GGTCGTTATA  GAGATGCAAG  GCGTGGTAAG   4080

AGAGTTTATC  GACAGCAGCC  AGCCACCGCT  TAGCGAGGTA  AATCAGGAGA  AGTTTAACAA   4140

TATCAAGAAA  GCACTAAGCG  AAGCGAAATA  ACTAAACCTT  CATGCGGCGG  ATTTTTCCGC   4200

CGCCTTATTG  AGCGAGATAG  CGATGCACGT  TACAGCCAAG  CCCTCCAGTT  TTCAATGTAA   4260

TCTCAAATGT  GATTACTGTT  TTTACCTTGA  AAAAGAGTCG  CAGTTTACTC  ATGAAAAATG   4320

GATGGATGAC  AGCACTTTGA  AAGAGTTCAT  CAAACAATAT  ATCGCAGCGT  CTGGCAATCA   4380

GGTCTATTTT  ACCTGGCAAG  GCGGTGAACC  CACTCTGGCT  GGCCTGGATT  TTTTCCGTAA   4440

AGTTATTCAC  TATCAACAAC  GCTATGCAGG  CCAAAAACGT  ATTTTTAATG  CATTACAAAC   4500

GAATGGCATT  TTATTGAATA  ATGAATGGTG  TGCCTTCTCA  AGAACATGA  ATTTCTGGTG   4560

GTATCTCGAT  CGATGGCCCC  CAGGAGTTAC  ATGACCGTTA  CAGACGCAGT  AATTCAGGTA   4620

ACGGTACTTT  TGCAAAAGTG  ATAGCAGCCA  TCGAGCGTCT  GAAATCATAT  CAAGTAGAGT   4680
```

| | | | | | |
|---|---|---|---|---|---|
| TTAATACGTT | AACCGTCATT | AATAACGTTA | ATGTCCATTA | CCCTCTTGAG | GTTTATCATT | 4740
| TTTTAAAATC | TATCGGCAGT | AAACATATGC | AATTTATCGA | ATTGCTAGAA | ACCGGGACGC | 4800
| CGAATATTGA | TTTCAGTGGT | CATAGTGAGA | ACACATTCCG | TATCATTGAT | TTTTCTGTGC | 4860
| CTCCCACGGC | TTATGGCAAG | TTTATGTCAA | CCATTTTTAT | GCAATGGGTT | AAAAACGATG | 4920
| TGGGTGAAAT | TTTCATCCGT | CAGTTTGAAA | GCTT | | | 4954

( 2 ) INFORMATION FOR SEQ ID NO:19:

( i ) SEQUENCE CHARACTERISTICS:
        ( A ) LENGTH: 3796 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Escherichia coli
        ( B ) STRAIN: Clinical Isolate EC- 39

( x i ) SEQUENCE DESCRIPTION: SEQ ID NO:19:

| | | | | | |
|---|---|---|---|---|---|
| AAGCTTAATC | GCGTGAATCA | GGAGTAAAAA | AATGACAACC | CAGACTGTCT | CTGGTCGCCG | 60
| TTATTTCACG | AAAGCGTGGC | TGATGGAGCA | GAAATCGCTT | ATCGCTCTGC | TGGTGCTGAT | 120
| CGCGATTGTC | TCGACGTTAA | GCCCGAACTT | TTTCACCATC | AATAACTTAT | TCAATATTCT | 180
| CCAGCAAACC | TCAGTGAACG | CCATTATGGC | GGTCGGGATG | ACGCTGGTGA | TCCTGACGTC | 240
| GGGCATCGAC | TTATCGGTAG | GTTCTCTGTT | GGCGCTGACC | GGCGCAGTTG | CTGCATCTAT | 300
| CGTCGGCATT | GAAGTCAATG | CGCTGGTGGC | TGTCGCTGCT | GCTCTCGCGT | TAGGTGCGCA | 360
| ATTGGTGCGG | TAACCGGGGT | GATTGTAGCG | AAAGGTCGCG | TCCAGGCGTT | TATCGCTACG | 420
| CTGGTTATGA | TGCTTTTACT | GCGCGGCGTG | ACCATGGTTT | ATACCAACGG | TAGCCCAGTG | 480
| AATACCGGCT | TTACTGAGAA | CGCCGATCTG | TTTGGCTGGT | TTGGTATTGG | TCGTCCGCTG | 540
| GGCGTACCGA | CGCCAGTCTG | GATCATGGGG | ATTGTCTTCC | TCGCGGCCTG | GTACATGCTG | 600
| CATCACACGC | GTCTGGGGCG | TTACATCTAC | GCGCTGGGCG | ACAACGAAGC | GACAACGCGT | 660
| CTTTCTGGTA | TCAACGTCAA | TAAAATCAAA | ATCATCGTCT | ATTCTCTTTG | TGGTCTGCTG | 720
| GCATCGCTGG | CGGGATCATA | GAAGTGGCGC | GTCTCTCCTC | CGCACAACCA | CGGCGGGGAC | 780
| TGGCTATGAG | CTGGATGCTA | TTGCTGCGGT | GGTTCTGGGC | GGTACGAGTC | TGGCGGGCGG | 840
| AAAAGGTCGC | ATTGTTGGGA | CGTTGATCGG | CGCATTAATT | CTTGGCTTCC | TTAATAATGG | 900
| ATTGAATTTG | TTAGGTGTTT | CCTCCTATTA | CCAGATGATC | GTCAAAGCGG | TGGTGATTTT | 960
| GCTGGCGGTG | CTGGTAGACA | ACAAAAGCA | GTAATAACGA | CTACAGGCAC | ATCTTGAATA | 1020
| TGAACATGAA | AAAACTGGCT | ACCCTGGTTT | CCGCTGTTGC | GCTAAGCGCC | ACCGTCAGTG | 1080
| CGAATGCGAT | GGCAAAAGAC | ACCATCGCGC | TGGTGGTCTC | CACGCTTAAC | AACCCGTTCT | 1140
| TTGTATCGCT | GAAAGATGGC | GCGCAGAAAG | AGGCGGATAA | ACTTGGCTAT | AACCTGGTGC | 1200
| TGGACTCCCA | GAACAACCCG | GCGAAAGAGC | TGGCGAACGT | GCAGGACTTA | ACCGTTCGCG | 1260
| GCACAAAAAT | TCTGCTGATT | AACCCGACCG | ACTCCGACGC | AGTGGGTAAT | GCTGTGAAGA | 1320
| TGGCTAACCA | GGCGAACATC | CCGGTTATCA | CTCTTGACCG | CCAGGCAACG | AAAGGTGAAG | 1380
| TGGTGAGCCA | CATTGCTTCT | GATAACGTAC | TGGGCGGCAA | AATCGCTGGT | GATTACATCG | 1440
| CGAAGAAAGC | GGGTGAAGGT | GCCAAAGTTA | TCGAGCTGCA | AGGCATTGCT | GGTACATCCG | 1500
| CAGCCCGTGA | ACGTGGCGAA | GGCTTCCAGC | AGGCCGTTGC | TGCTCACAAG | TTTAATGTTC | 1560

| | | | | | | |
|---|---|---|---|---|---|---|
| TTGCCAGCCA | GCCAGCAGAT | TTTGATCGCA | TTAAAGGTTT | GAACGTAATG | CAGAACCTGT | 1620 |
| TGACCGCTCA | TCCGGATGTT | CAGGCTGTAT | TCGCGCAGAA | TGATGAAATG | GCGCTGGGCG | 1680 |
| CGCTGCGCGC | ACTGCAAACT | GCCGGTAAAT | CGGATGTGAT | GGTCGTCGGA | TTTGACGGTA | 1740 |
| CACCGGATGG | CGAAAAAGCG | GTGAATGATG | GCAAACTAGC | AGCGACTATC | GCTCAGCTAC | 1800 |
| CCGATCAGAT | TGGCGCGAAA | GGCGTCGAAA | CCGCAGATAA | AGTGCTGAAA | GGCGAGAAAG | 1860 |
| TTCAGGCTAA | GTATCCGGTT | GATCTGAAAC | TGGTTGTTAA | GCAGTAGTTT | TAATCAGGTT | 1920 |
| GTATGACCTG | ATGGTGACAT | AAATACGTCA | TCGACAGATG | AACGTGTAAT | ATAAAGAAAA | 1980 |
| GCAGGGCACG | CGCCACCCTA | ACACGGTGGC | GCATTTTATG | GACATCCCGA | ATATGCAAAA | 2040 |
| CGCAGGCAGC | CTCGTTGTTC | TTGGCAGCAT | TAATGCTGAC | CACATTCTTA | ATCTTCAATC | 2100 |
| TTTTCCTACT | CCAGGCGAAA | CGTAACCGGT | AACCACTATC | AGGTTGCATT | TGGCGGCAAA | 2160 |
| GGCGCGAATC | AGGCTGTGGC | TGCTGGGCGT | AGCGGTGCGA | ATATCGCGTT | TATTGCCTGT | 2220 |
| ACGGGTGATG | ACAGCATTGG | TGAGAGCGTT | CGCCAGCAGC | TCGCCACTGA | TAACATTGAT | 2280 |
| ATTACTCCGG | TCAGCGTGAT | CAAAGGCGAA | TCAACAGGTG | TGGCGCTGAT | TTTTGTTAAT | 2340 |
| GGCGAAGGTG | AGAATGTCAT | CGGTATTCAT | GCCGGCGCTA | ATGCTGCCCT | TCCCCGGCG | 2400 |
| CTGGTGGAAG | CGCAACGTGA | GCGTATTGCC | AACGCGTCAG | CATTATTAAT | GCAGCTGGAA | 2460 |
| TCACCACTCG | AAAGTGTGAT | GGCAGCGGCG | AAAATCGCCC | ATCAAAATAA | AAACTATCGT | 2520 |
| TCGCTTAACC | CGCTCCGGCT | CGCGAACTTC | CTGACGAACT | CTGCGCTGTG | GACATTATTA | 2580 |
| CGCCAAACGA | AACGGAAGCA | GAAAAGCTCA | CCGGTATTCG | TGTTGAAAAT | GATGAAGATG | 2640 |
| CAGCGAAGGC | GGCGCAGGTA | CTTCATGAAA | AAGGTATCCG | TACTGTACTG | ATTACTTTAG | 2700 |
| GAAGTCGTGG | TGTATGGGCT | AGCGTGAATG | GTGAAGGTCA | GCGCGTTCCT | GGATTCCGGG | 2760 |
| TGCAGGCTGT | CGATACCATT | GCTGCCGGAG | ATACCTTTAA | CGGTGCGTTA | ATCACGGCAT | 2820 |
| TGCTGGAAGA | AAAACCATTG | CCAGAGGCGA | TTCGTTTTGC | CCATGCTGCC | GCTGCGATTG | 2880 |
| CCGTAACACG | TAAAGGCGCA | CAACCTTCCG | TACCGTGGCG | TGAAGAGATC | GACGCATTTT | 2940 |
| TAGACAGGCA | GAGGTGACGC | TTGGCTACAA | TGAAAGATGT | TGCCCGCCTG | GCGGGCGTTT | 3000 |
| CTACCTCAAC | AGTTTCTCAC | GTTATCAATA | AAGATCGCTT | CGTCAGTGAA | GCGATTACCG | 3060 |
| CAAAGTGAGC | GCGATTAAAG | ACTCAATTAC | GCGCCATCAG | CTCTGGCGCG | TAGCCTCAAA | 3120 |
| CTCAATCAAA | CACATACCAT | TGGCATGTTG | ATCACTGCCA | GTACCAATCC | TTTCTATTCA | 3180 |
| GAACTGGTGC | GTGTCGTTGA | ACGCAGCTGC | TTCAACGCG | GTTATAGTCT | CGTCCTTTGC | 3240 |
| AATACCGAAG | GCGATGAACA | GCGGATGAAT | CGCAATCTGG | AAACGCTGAT | GCAAAACGC | 3300 |
| GTTGATGGCT | TGCTGTTACT | GTGCACCGAA | ACGCATCAAC | CTTCGCGTGA | AATCATGCAA | 3360 |
| CGTTATCCGA | CAGTGCCTAC | TGTGATGATG | GACTGGGCTC | CGTTCGATGG | CGACAGCGAT | 3420 |
| CTTATTCAGG | ATAACTCGTT | GCTGGGCGGA | GACTTAGCAA | CGCAATATCT | GATCGATAAA | 3480 |
| GGTCATACCC | GTATCGCCTG | TATTACCGGC | CCGCTGGATA | AAACTCCGGC | GCGCTGCGGT | 3540 |
| TGGAAGGTTA | TCGGGCGGCG | ATGAAACGTG | CGGGTCTCAA | CATTCCTGAT | GGCTATGAAG | 3600 |
| TCACTGGTGA | TTTTGAATTT | AACGGCGGGT | TTGACGCTAT | GCGCCAACTG | CTATCACATC | 3660 |
| CGCTGCGTCC | TCAGGCCGTC | TTTACCGGAA | ATGACGCTAT | GGCTGTTGGC | GTTACCAGG | 3720 |
| CGTTATATCA | GGCAGAGTTA | CAGGTTCCGC | AGGATATCGC | GGTGATTGGC | TATGACGATA | 3780 |
| TCGAACTGGC | AAGCTT | | | | | 3796 |

( 2 ) INFORMATION FOR SEQ ID NO:20:

( i ) SEQUENCE CHARACTERISTICS:

( A ) LENGTH: 5541 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
    ( A ) ORGANISM: Escherichia coli
    ( B ) STRAIN: Clinical Isolate EC- 625

( x i ) SEQUENCE DESCRIPTION: SEQ ID NO:20:

```
AAGCTTAAGC CTGCATTTGC TCAATGAAGC GCAGAATGAG CTGGAACTGT CAGAAGGCAG      60
CGACGATAAC GAAGGTATTA AGAACGTAC  CAGCTTCCGT CTGGAGCGTC GGGTCGCCGG     120
AGTGGGTCGT CAAATGGGCC GCGGTAACGG CTATCTGGCA ACCATCGGCG CGATTTCTCC     180
GTTCGTTGGT CTGTTTGGTA CGGTCTGGGG CATCATGAAC AGCTTTATTG GTATCGCGCA     240
AACGCAGACC ACTAACCTGG CAGTCGTTGC GCCGGGTATC GCAGAAGCTC TGTTAGCAAC     300
GGCAATCGGC CTCGTGGCAG CGATTCCTGC GGTCGTTATC TATAACGTAT TTGCACGCCA     360
GATTGGCGGC TTTAAAGCGA TGCTGGGTGA TGTTGCAGCG CAGGTATTGT TGCTGCAAAG     420
CCGTGACCTG GATCTGGAAG CCAGCGCCGC TGCGCATCCG GTTCGTGTCG CACAAAAATT     480
ACGCGCAGGA TAATATCCGA TGGCAATGCA TCTTAACGAA AACCTCGACG ATAACGGCGA     540
AATGCATGAT ATCAACGTGA CGGCGTTTAT CGACGTGATG TTGGTTCTGC TGATTATCTT     600
TATGGTGGCG GCACCGTTAG CGACGGTAGA TGTGAAGGTG AACTTGCCTG CTTCTACCAG     660
CACGCCGCAG CCGCGGCCGG AAAAACCGGT TTATCTGTCG GTGAAGGCAG ACAACTCGAT     720
GTTTATCGGT AACGATCCGG TCACCGATGA AACAATGATT ACGGCGTTGA ATGCGTTAAC     780
CGAAGGCAAG AAAGACACCA CCATCTTCTT CCGAGCGGAT AAAACCGTCG ATTACGAGAC     840
GTTGATGAAG GTAATGGATA CGCTGCATCA GGCGGGTTAC CTGAAGATAG GTCTGGTCGG     900
CGAAGAAACC GCCAAAGCGA AGTAAAGTAG AATTGCCTGA TGCGCTACGC TCATCAGGCC     960
TACAAAATCT ATTGCAACAT GTTGAATCTT CGTGCGTTTG TAGGCCGGAT AAGGCGTTCA    1020
CGCGCATCCG GCATTAGGTG CTCAATGCCT GATGCGCTAC GTTTATCAGG CCTACAAAAT    1080
CTATTGCAAC ATGTTGAATC TTCATGCGTT TGTAGGCGGA TAAGGCGTTT TCGCACATCA    1140
GGTAAGAGTG AATTCACAAT GATGCCCGGT TGCTTTTCAC AACCGGGCAT TTTTTAACC    1200
TAAATGCTCG CCGCCGCACA CACCGTGCAC TTCTGCGGTG ACGTAGCTCG ACTCCTGACT    1260
TGCCAGATAA ACATATACTG GGGCCAGTTC CGCCGGTTGC CCCGCACGCT TCATCGGCGT    1320
TTTCTGACCA AACTGCGGGA TCTTATCCTG CGTTTGTCCG CCGGAAATTT GCAGTGCCGT    1380
CCAGATAGGG CCTGGCGCGA CAATATTCAC CCGAATACCT TTCTCCGCGA CCTGTTTTGC    1440
CAGGCCACGG CTGTAGTTCA GAATCGCCGC CTTCGTAGCC GCATAGTCCA GTAAATGCGG    1500
ACTTGGCTGG TATGCCTGGA TTGACGAAGT GGTGATAATA CTTGCACCTT TCGGTAGCAG    1560
GGGGATCGCT TCCTGGGTTA GCCAGAACAG CGCGAAAACG TTAATGGCAA AGGTCTTTTG    1620
AAACTGTTCG CTGGTGAGGT CTGCAATATC AGGAATGGCA ACCTGTTTCC CGGCGACCAG    1680
CGCCATAATA TCCAGCCCGC CTAACGCCTT GTGCGCTTCG TGAACCAGCG AACGGGCGAA    1740
TTTCTCATCG CTTAAATCGC CTGGCAGCAG AACGGCTTTG CGTCCGCATT CTTCAATGAT    1800
CTTTTTCACA TCCTGAGCGT CTTCTTCTTC CACGGGAAGA TAACTGATCG CCACGTCAGC    1860
CCCTTCACAC GCGTAAGATG GCGGCAGCGC GACCGATTCC GGAATCGCCC CCTGTCACCA    1920
GTGCTTTACG ATCTTTCAGG CGACCGCTAC CAACATAGGT TTTCTCGCCG CAATCCGGTA    1980
CCGGTGTCAT CTTCGCCTGG ATGCCTGGCG TCGGTTGTTT CTGTTTGGGA TATTCACCAG    2040
```

```
TGTAATACTG CGTGGTCGGG TCTTTTAAAT GAGACATCGT TTTTCTCCCT TCAGGTTCAA    2100
CGTCCTTTAA GGGTAGACGC TCTCGATGCG TTGATAAGGG AACCAGGAAG ATCCCTAACC    2160
CTCAGAATTA TGCGACAAAG GTTTAACGGA TATGTTGATT TGCTGTTGCG CGCTGTTTAC    2220
TCAATTGCGA TATACTGTTG CCCGTTTTAA CTACACGACA GGAATGTATG GAACGTTTTC    2280
TTGAAAATGC AATGTATGCT TCTCGCTGGC TGCTTGCCCC CGTGTACTTT GGCCTTTCGC    2340
TGGCGTTAGT TGCCCTGGCG CTGAAGTTCT TCCAGGAGAT TATTCACGTA CTGCCGAATA    2400
TCTTCTCGAT GGCGGAATCA GATTTGATCC TCGTGTTGCT GTCGCTGGTG GATATGACAC    2460
TGGTTGGCGG TTTACTGGTG ATGGTGATGT TTTCCGGTTA TGAGAATTTC GTCTCGCAGC    2520
TGGATATCTC CGAGAACAAA GAGAAGCTGA ACTGGCTGGG GAAAATGGAC GCAACGTCGC    2580
TGAAAAACAA AGTAGCAGCG TCGATTGTGG CAATTCTTC CATTCACTTA CTGCGCGTCT    2640
TTATGGATGC GAAAAATGTC CCTGATAACA AACTGATGTG GTACGTCATT ATCCATCTGA    2700
CGTTTGTGCT CTCTGCATTT GTGATGGGCT ATCTTGACCG ACTGACTCGT CATAATCACT    2760
GATCTTATGC GGGCGCGGTT CTCGCGCCCG TTATTAACAG GTCATTTATC GGAAGACGCC    2820
TGCCACAGAT TCAGCTCGCC ATCGGCGATA TGCTGATCAA TCTGCGCCAG CTCCTCGGTG    2880
CTAAATGTCA GATTATTCAG CGCCTGCACG TTCTCCTCAA GTTGTCCGCG CGGCTGGCAC    2940
CAATCAATAC CGACGTCACG CGATCATCTT TCAGCAACCA GCTTAACGCC ATTTGCGCCA    3000
TTGATTGTCC ACGCTGCTGT GCCATTTCAT TCAATAAGTG TAGGCTGTTG AGGTTGGCTT    3060
CGGTAAGCAT TTTCGGCGTC AGACCACGAA CTTTATTCCC TTCACGATGC ATCCGTGAAT    3120
CTTGCGGAAT GCCGTTGAGA TATTTTCCGG TCAGCAATCC CTGAGCCAGA GGAGTAAAGG    3180
CAATACAGCC CACGCCGTTA TTTTGCAGGG TATCCAGCAG GCCGCTTTTA TCCACCCAGC    3240
GGTTCAGTAA ATTGTACGAA GGTTGATGAA TTAACAGCGG AATTTTCCAC TCGCGCAGCA    3300
ACTCAACCAT TTTTTGCGTC CGCTCTGGCG AGTAAGAGGA GATCCCGACA TAAAGCGCCT    3360
TACCGCTTTG TACCGCATGA GCCAGCGCAG AGGCGGTTTC TTCCATCGGC GTATTTTCAT    3420
CGACGCGATG AGAGTAAAAG ATATCGACAT ACTCAAGCCC CATACGCTTC AGGCTTTGGT    3480
CGAGGCTGGA GAGCAGGTAT TTACGTGAAC CGCCAGAGCC GTAAGGGCCG GCCACATAT    3540
CGTAGCCAGC CTTGGTAGAG ATAATCAGTT CATCGCGATA AGCGGCAAAA TCCTCCCGCA    3600
GCAGGCGACC AAAGTTCTCT TCTGCGCTTC CTGGAGGCGG CCCGTAATTG TTGGCTAAAT    3660
CAAAGTGCGT AATGCCTAAA TCAAACGCTT TACGCAGGAT TGCACGCTGT GATTCCAGCG    3720
CGTTAACGTG ACCGAAATTG TGCCATAAAC CGAGCGATAA CGCGGGCAGG CGTAAACCAC    3780
TTTTTCCGCA ATAGCGGTAC TGCATCTGCC CGTAACGTTC GGGTTCGCTA ACCAGACCAT    3840
GACCTCTCCT TTCCACCGTT CAATTTCGAA ACAATGTTTC TAGTTTAGCG ATTCGCCAGC    3900
GCGTATCCCG TAGTCTGGCT CACAGAGTGA CGAAAAATTG GCAAAAACAC GCGCTTATGC    3960
TTTGCTTAAA AAAACACCAG TTGAGGAGTG CAACGATGCC GCGTTTAACC GCCAAAGATT    4020
TCCCACAAGA GTTGTTGGAT TACTACGACT ATTACGCTCA CGGGAAAATC TCGAAACGTG    4080
AGTTCCTCAA TCTTGCGGCG AAGTATGCGG TGGGCGGGAT GACGGCATTA GCGTTGTTTG    4140
ATTTGCTCAA GCCAAATTAT GCGCTGGCGA CTCAGGTAGA GTTTACCGAC CTGGAGATTG    4200
TTGCTGAGTA CATCACGTAT CCTTCGCCAA ATGGTCACGG CGAGGTACGG GGTTATCTGG    4260
TGAAACCCGC AAAAATGAGC GGCAAAACGC CAACCGTGGT GGTGGTGCAT GAGAATCGTG    4320
GACTGAATCC GTATATCGAA GATGTGGCAC GGCGAGTGGC GAAGGCGGGG TATATCGCCC    4380
TGGCACCTGA CGGCTTAAGT TCCGTTGGAG GTTATCCGGG AAATGATGAT AAAGGTCGTG    4440
```

| | | | | | | |
|---|---|---|---|---|---|---|
| AGCTGCAACA | GACAGGTTGA | TCCAACCAAA | CTGATGAATG | ATTTCTTTGC | CGCAATTGAG | 4500 |
| TTTATGCAAC | GCTATCCGCA | AGCGACAGGC | AAAGTGGGTA | TTACCGGATT | TTGCTATGGC | 4560 |
| GGTGGCGTAT | CGAACGCGGC | GGCTGTCGCG | TATCCGGAAC | TGGCCTGCGC | GGTGCCGTTT | 4620 |
| TATGGTCGTC | AGGCACCCAC | TGCCGATGTG | GCGAAGATTG | AAGCGCCTTT | ACTACTCCAC | 4680 |
| TTCGCGGAAC | TGGACACCCG | AATCAACGAG | GGCTGGCCTG | CTTACGAGGC | GGCGTTGAAA | 4740 |
| GCCAATAATA | AGGTTTATGA | GGCGTATATC | TATCCGGGGG | TTAATCACGG | ATTCCATAAT | 4800 |
| GATTCCACGC | CCCGTTATGA | CAAATCTGCC | GCCGATCTTT | CCTGGCAAAG | GACACTGAAA | 4860 |
| TGGTTCGATA | AATATCTCTC | CTGATAGGTT | TATCTCTTAC | GGGATTACGT | CTTAAACAAG | 4920 |
| CATGAAAAAA | TAGCGTGCGC | AAAAGTCGTT | CTTTGCCTAA | AATATCGCTA | TATATAACAA | 4980 |
| TATATAGCGA | ATGAGGTGAA | CGATGAATAA | CCATTTTGGT | AAAGGCTTAA | TGGCGGGATT | 5040 |
| AAAAGCAACG | CATGCCGACA | GTGCGGTTAA | TGTGACAAAA | TACTGTGCCG | ATTATAAACG | 5100 |
| CGGTTTTGTA | TTAGGCTACT | CACACCGGAT | GTACGAAAAG | ACCGGAGATC | GCCAGCTTAG | 5160 |
| CGCCTGGGAA | GCGGGTATTC | TGACGCGCCG | CTATGGACTG | GATAAAGAGA | TGGTAATGGA | 5220 |
| TTTCTTTCGT | GAGAATAATT | CCTGTTCTAC | GTTGCGCTTT | TTTATGGCCG | GTTATCGCCT | 5280 |
| CGAAAATTGA | TCAAACATAC | GTATTATCTT | GCTTTAATTA | ATTACACTAA | TGCTTCTTCC | 5340 |
| CTTCGTTTTA | GCGCCCCGCC | GCAGTATCAT | GATATCGATA | ACCATAATAA | ATGTGTGGTA | 5400 |
| AATGGCGCAT | CGATCGCATT | ATTGATTTTG | CGATTGAGGC | AAAATATATG | CCAGGTCTTC | 5460 |
| GCAACGGAAT | AACTATAAAT | GACTGGAGAT | AACACCCTCA | TCCATTCTCA | CGGCATTAAC | 5520 |
| CGTCGTGATT | TCATGAAGCT | T | | | | 5541 |

(2) INFORMATION FOR SEQ ID NO:21:

(i) SEQUENCE CHARACTERISTICS:
  (A) LENGTH: 6317 base pairs
  (B) TYPE: nucleic acid
  (C) STRANDEDNESS: double
  (D) TOPOLOGY: linear (ii) MOLECULE TYPE: Genomic DNA (vi) ORIGINAL SOURCE:
  (A) ORGANISM: Enterobacter cloacae
  (B) STRAIN: Clinical Isolate ET-12

(xi) SEQUENCE DESCRIPTION: SEQ ID NO:21:

| | | | | | | |
|---|---|---|---|---|---|---|
| AAGCTTGCCC | GCATCATTCA | GGAGCAGGGG | CGTCGCGACC | AGTTAGGTGT | GAAGTTTGGC | 60 |
| AGCGGTGACA | GCCCGGACTG | CCGGGGGATC | ACGGTTCCGG | AACTGCAGAG | TATCGACTTC | 120 |
| GACAAAATCA | ACTTCTCTGA | CTTCTACGAG | GATTTGATGA | AGAACCAGAA | AATCCCCGAT | 180 |
| ACCAGCGCGC | AGGTCAAGCA | GATTAAGGAT | CGCATCGCCG | CGCAGGTGAA | CCAGCAGGGA | 240 |
| GGTGGCAAAT | GAAGCGTGTC | CTCTGTGGCC | TGCTTATGGC | GCTGGCGAGC | CATACGGCAC | 300 |
| TGGCCGATGA | GATTGTGACG | CCGGCTGAGC | CGTTCACCGG | CTGGTCCTGG | TACAACGAAC | 360 |
| CGAAAAAGCC | CCCTGAGCAG | CCCCGGAAAC | CGCAGCAGCC | AGCACCGCAG | CCATTCCGGA | 420 |
| TCTCAGCAAA | ATGTCCCCGA | TGGAGCAGGC | CAGGGTGCTG | AAAGGGTATA | CACAGGAGGC | 480 |
| GCTTAACCGC | GCCATCCTGT | ACCCCTCAAG | GGAAAACACG | GCGACGTTCC | TGCGCTGGCA | 540 |
| GAAGTTCTGG | ACGGACCGGG | CATCGATGTT | CAGCCAGTCC | TTTGCGGCGG | CGCAGCTGAG | 600 |
| CCATCCGGAC | CTCGACTACA | ACCTGGAGTA | TCCGCACTAC | AACAGCATGG | CGCCGTTTAT | 660 |
| GCAGACCCGT | GACCAGCAGA | CGCGGCAGAG | CGCCGTGGAG | CAGCTTGCGC | AGAGTACGGT | 720 |

| | | | | | |
|---|---|---|---|---|---|
| CTGTTCTACT | TCTACCGGGG | CAGTGACCCG | ATTGATGTGC | AGATGGCGGG | CGTGGTGGCT | 780
| GACTTTGCGA | AAACCAACGG | GATCTCACTC | ATTCCGGTCT | CGGTTGACGG | ACAGGTGGCG | 840
| GCCACCCTGC | CGCAAAGCCG | TCCGGACACC | GGACAGTCCC | GGTCGATGAA | TATCACGCAC | 900
| TTTCCGGCGC | TCTTCCTGGT | TGACCCGCGC | AACCAGAACT | ACCGTGCCCT | GTCCTATGGC | 960
| TTCATGACCC | AGGATGACCT | GTCAAAACGA | TTCCTGAACG | TGGCCACCGG | CTTTAAACCC | 1020
| AATTCCTGAG | AGCCTTTTAT | GACAAAAACA | CTGTTTACCT | CATCCGCGAT | GCAGGGCGGG | 1080
| CTGCCCTGTA | TTCCTTCGTC | CTCGGCCCGG | CACTGGTGCT | GTATGTGTTT | GTGATGCTGG | 1140
| CGGCATCAGA | CGGCTCACTT | TCCCGGCAAT | TCCTGACGAC | CTTTCATCAC | CTGACTGAGG | 1200
| GTGCGCCTGC | CGGCAAGGTG | ATGGGATGTG | TTAATGAACA | TGAGATGGCA | GGGCGTTTCT | 1260
| CGCCACCTGA | ACCCGGAGAG | TCGTTAAAGC | CCGTGCCTTC | CGTTTTAGAT | AAAGCACCGC | 1320
| CTGAAGTGTT | ATGTCAGCTC | GGGCCCGTTG | ACAGCGATTC | GTGGGCGCGT | ACGACAGATG | 1380
| CAACGTTGCT | CAACACCTGG | ATTATCTCGG | TGATGTTTGG | CTTTGGTGTG | TGGTTTGTTT | 1440
| TATATGGCCT | GTCCCGGGCC | GCTCAGCGTC | GCATTTCACC | AGACACACAT | TCTGTACTGG | 1500
| TACGGCAGAA | CAAGGAGACA | CAGGAATGAA | ACCAACTCTT | CTCGCAGGAC | TGATTTTCTG | 1560
| GGGCATGATG | GCGCGCCGTA | CTGAGCGAGC | TGATGACCTG | GTCCGTGGAG | CATACACAGC | 1620
| AGGGCCTGCT | GTGGCTGTGC | AATGGGATGT | GGGCCGGGGC | GGCTGGCATG | GTGATTTATG | 1680
| CAGGTTATCG | CTGGTACCGT | GACGAAAGAG | GGCAAACGCA | TAAGGAAGGC | GATCATGAAC | 1740
| ATTAAAACCG | GACTCACGGC | TCTGCTGATG | TGCCTGCCCC | TGCTGGCGAA | CGCGGGGGCG | 1800
| CGCGAGGAGT | TAATGGCGCT | TGAAGCGACA | AAAACAACCT | CTGCTGACGC | TGCAGCCATC | 1860
| ACCGCCTCCA | CCATTCCGGT | ACCTGCGCCG | GCCAGCCTGA | TGGCGCTGCC | GGACGGACGT | 1920
| CGGGCTAACA | TGAAAGATTA | TGCCGTGGTG | CTTTTTATGC | AGGCACACTG | CCAGTACAGC | 1980
| GCGAAGTTTG | ACCCGCTGCT | GAAGGGCTGG | GCTGATGAGC | ATTCTGTCAG | GGTTTATCCA | 2040
| TACACCCTGG | ACGGCGGCGG | TGATGTGTCT | TACCGACGCC | GATGATCCCG | CGCAAGACGG | 2100
| ACCCGAATTC | TCCCATTGCA | GACGAGATTG | TCACCTTCTT | CGGAAACGGG | CTGCCGATTG | 2160
| CGACACCAAC | GGCCTTTATG | GTCAACGTTA | ACACCCTGAA | AGCCTACCCG | CTGACCCAGG | 2220
| GTGTGATGGA | CATCCCCGCT | CTTGAGAGCC | GTATGGCCAG | CCTGATTCAG | GCTGACATGG | 2280
| ACAACGTCGA | TCCGAAAACG | CTGCCGCCCA | TGCCGGCAAG | TGCGCAGGTC | ACCCCTCAGT | 2340
| AATACAAACG | GACTACAAAA | TGACGACAAA | TACGTATGCG | TTATCGCGTA | CCGAGCGCGT | 2400
| GTGGCTGTTA | TTCAGCGTGA | CGCTGCTTGT | GTCCGCAGCT | TTCTATGGGG | TACTGGCCCA | 2460
| CCGGGTGGTC | AGCGTCTGAC | CGTCAGACTG | ACAACTGTTT | GCAGGACTTT | CCGGTGCTCC | 2520
| TGCTTATCTC | GCTGAGTATC | GGATTCTTTT | TCACCGTCAC | CGGGCTGTAC | GTCTGCCGGC | 2580
| AGACCCTGGT | CAGGAAACCC | CGGGAGGAGA | TTGCATGAGG | CACATCAGAC | TGAAGACGTT | 2640
| TATCCGAAAC | CAGGCTATCG | GGATACTGAA | AGACAGTAGT | GAGGATACGG | AAACCCGAAA | 2700
| ATGGACGGAT | TTGTTAACCC | TGAAACTGTT | TTTATGCCTT | AATTTTTACC | GCCGTAGTCG | 2760
| AAAGGGTATA | CGTGAAGTGC | GCCATCACAA | CGCTCAGTGC | GATCTCCGTT | GACCGCTCCG | 2820
| AACAGTTTAC | GCTCTCGCTT | CTCATCCACT | ATCCACAGTA | CCTGTTGTGG | GGCGTTATGG | 2880
| CCGCGATTAT | CGCGCTCATT | GCGGTGAATT | TACTCGTCTG | CGGCTGGTTC | TGTCTGGCCA | 2940
| CATATCTTTG | CCGCAAACTG | AACCGGACTG | ACATCCCGGC | AGGCAAGGAT | ATGCAAGCTG | 3000
| TGGAGGTGCC | TAATGATTAA | GGCGCTTATT | ACGGCAGGGG | TTGTGTTCTT | CTCAGGTCTG | 3060
| GCAGCGCTGC | CTGCTCAGGC | GGACGTCAAT | GGTGACTCAA | CGGCTTCTTT | GGCAAGCTGG | 3120

| | | | | | |
|---|---|---|---|---|---|
| GCTACAGCGG | CAACGTCTCT | CAGGCGCAGG | CCTGGCAGGG | GCAGGCGGCC | GGGTATTTCT 3180 |
| CCGGCGGGTC | GGTCTACCTG | CGAAACCCCG | TCAAAAACGT | TCAGCTGATC | TCGATGCAGC 3240 |
| TGCCGTCCCT | GAACGCCGGC | TGCGGCGGTA | TCGATGCCTA | CCTGGGGTCA | TTCAGCATGA 3300 |
| TCAGCGGTGA | GGAAATTCAG | CGATTCGTGA | AGCAAATCAT | GAGTAACGCG | GCTGGCTATG 3360 |
| CATTCGACCT | GGCACTGCAG | ACGATGGTCC | CGGAGCTGAA | GCAGGCGAAA | GATTTCCTGC 3420 |
| AGAAGCTGGC | CAGTGATGTT | AACTCCATGA | ACATGAGTTC | GTGCCAGGCC | GCTCAGGGCA 3480 |
| TCATAGGCGG | GTTGTGGCCC | GTAACGCAGG | TGTCACAGCA | GAAAATCTGC | CAGGACATTG 3540 |
| CCGGCGAAAC | CAACATGTTT | GCTGACTGGG | CGGCCTCCCG | CCAGGGCTGC | ACCGTCGGAG 3600 |
| GACAGGGGGA | TAAAGTCACG | GCCAAAGCCG | GCGACGCAGA | AAAAAGACCC | AGGTACTGAA 3660 |
| AAACAAAAAC | CTTATCTGGG | ACACGCTCAG | TAAGAACGGG | CTGCTTGGTA | ACGATCGCGC 3720 |
| CCTGAAGGAG | CTGGTCATGA | GTACTGTCGG | CTCCATCATT | TTCAACAAAA | CCGGAGACGT 3780 |
| GACATCCTGA | CGCCGCTGGT | CGATACCGCG | ACCTGATTAA | AGTTCTGATG | CGCGGGGGAA 3840 |
| CAGCGAAGGT | CTACGGGTGC | GATGAGGCAA | CACTCTGTCT | GGGGCCTGTC | GTTACTAACC 3900 |
| TGACGATTAC | TGAGTCCAAC | GCTCTGGTCA | CACTGGTCAA | AAAACTGATG | CTCTCGATGC 3960 |
| AGAACAAACT | TGTCGATGAC | AAACCGCTGA | CCGATCAGGA | AAAAGGCTTC | GTGAACACCA 4020 |
| CCTCTGTGCC | GGTACTGAAA | TACCTGACCA | ACGCCCAGAG | TATGGGGATG | AGCGCCACGT 4080 |
| ACCTCCTGCA | GGTTTCCGAC | TTCATCGCGC | AGGACCTGAT | GATCCAGTAC | CTCCAGGAAC 4140 |
| TGGTGAAACA | GGCAAGCCTG | TCTCTGGCTG | GTAAGAACTT | CCCGGAAGAG | GCCGCTGCGA 4200 |
| AGTGCGCGAC | AACATCATTC | ATGCCCAGGG | ACTGCTGGCC | GACATGAAGC | TGCAGTCTGC 4260 |
| GGCAGACCAG | AACGCACTGG | ACGGCATCGA | CCGCAACATG | CAGTACTGCA | GCAGCAGGTG 4320 |
| TCCACCATTG | TTTCAGGCTC | CTATCAAAGC | AACTATCACT | GGGGTGATCG | CTGATGCTTG 4380 |
| AGATATACAC | CATTTATGGC | GGGGGAATGT | GGAAAAACGC | GCTGGACGCC | GTTGTCACCC 4440 |
| TTGTCGGTCA | GAATACCTTC | CACACCTTAA | TGCGTATTCG | CCCGGCACCT | TCGGGGTGCT 4500 |
| GGCTGTATTG | CTCACTTTCA | TCAAACAACG | TAACCCGATG | GTCTTCGTCC | AGTGGCTGGC 4560 |
| GATCTTCATG | ATCCTGACGA | CCATCCTGCT | GGTACCGAAA | CGTTCAGTAC | AGATAATTGA 4620 |
| CCTCTCAGAC | CCCGGCTGCG | GTGTGGAAAA | CCGATAATGT | ACCGGTCGGT | CTGGCTGCCA 4680 |
| TCGCGTCACT | GACGACCAGC | ATCGGTTACA | AAATGGCATC | GGTGTACGAC | ATGCTGATGG 4740 |
| CCAGACCTGA | CTCGGTAACC | TACAGCAAGA | CCGGTATGCT | GTTTGGCTCG | CAGATTGTGG 4800 |
| CGGAAACCAG | TGACTTCACC | ACGCAAAACC | CGGAACTGGC | TCAGATGCTG | CCGGACTACG 4860 |
| TGGAAAACTG | TGTGATCGGC | GACATTCTGC | TGAACGGTAA | ATACACCATC | AATCAGCTGC 4920 |
| TCAATTCCAC | TGACCCGCTG | ACGTTGATAA | CCAGTAACCC | AAGCCCGCTG | CGGGGCATCT 4980 |
| TTAAGATGAC | CTCCACCTCG | CGCCAGTTCC | TGACCTGTCA | GCAGGCGGCA | ACGGAGATTA 5040 |
| AGACGCTGGC | GAATACCGAC | GTCAATCCGG | GCAGTGCGAC | GTTCACCTGG | CTGACGCGGA 5100 |
| AGGTATTCGG | CAACAAGCTG | AATGGTGCCT | CGCTTCTGCC | AACGCTATGG | GTGAGAGCTA 5160 |
| CGGATTCTTC | TATGCCGGGG | GAATGACGGC | TGCGCAGATC | ATGAAGAACA | ACATCACGAA 5220 |
| CAGTGCAGTT | CGGCAGGGGA | TTAAGGGTTT | CGCCGCTCGC | TCATCCGACA | CGGCTAACCT 5280 |
| GCTGAACCTG | GCCACCGAGA | ACGCTGCAAC | CAAACAGCGT | CTCAGCTGGG | CTGCGGGTAA 5340 |
| TGAGCTTGCC | ACCCGAACTC | TGCCGTTTGC | ACAGTCCCTG | CTGATGCTTA | TCCTGGTGTG 5400 |
| CCTGTTCCCG | TTGATGATTG | CGCTGGCCGC | ATCAAATCAC | ACTATGTTTG | GGCTGAACAC 5460 |
| CCTGAAAATA | TACATTTCCG | GTTTTATCTA | TTTCCAGATG | TGGCCGGTGA | TGTTCGCCAT 5520 |

| | | | | | | |
|---|---|---|---|---|---|---|
| CCTTAACTAT | GCTGCCAACT | ACTGGCTGCA | GAGTCAGTCC | GGGGGCACGC | CTCTGGTGCT | 5580 |
| GGCCAACAAG | GATGTAGTGG | CACTGCAGCA | TTCGGACGTG | GCGAATCTGG | CAGGGTATCT | 5640 |
| GTCGTTGTCC | ATTCCGGTGC | TGTCGTTCGT | ATCTGACCAA | GGGGGCTGCG | GCGATGGGCT | 5700 |
| CTCAGGTGGC | AGGCAGTGTC | CTCAGTTCGG | GCGCCTTCAC | GTCGGCAGGT | GTGGCAGCAA | 5760 |
| CCACGGCGGA | CGGGAACTGG | TCGTTTAACA | ACATGTCAAT | GGACAATGTC | AGCCAGAACA | 5820 |
| AGCTGGATAC | CAACCTGATG | CAGCGTCAGG | CCAGCAGACG | TGGCAGGCAG | ATAATGGTTC | 5880 |
| CACGCAGACG | CAGACGCCGG | TGGCCATACG | GTATCGACGG | CTCAGGCGCA | ATGTCGAATC | 5940 |
| TGCCGGTGAA | CATGAAGCTC | AGCCAGCTGG | CCAGCAGTGG | TTTCCAGGAG | TCTGCCCGCC | 6000 |
| AGTCGCAGGT | CCAGGCGCAG | ACGGCGCTCG | ATGGCTACAA | CCACAGTGTC | ACCAGTGGCT | 6060 |
| GGTCGCAGCT | CTCACAGCTG | TCTCACCAGA | CCGGTACCAG | CGACAGCCTG | ACCAGCGGCA | 6120 |
| GTGAAAACAG | CCAGGCCACT | AACTCAACGC | GCGGCGCGAG | CATGATGATG | TCGGCCGCTG | 6180 |
| AAAGCTATGC | GAAAGCTAAC | AATATCTCGA | CGCAGGAAGC | CTATAACAAG | CTGATGGATA | 6240 |
| TCAGTAATCA | GGGTTCTGTA | TCTGCAGGCA | TTAAAGGTAC | GGCCGGAGGG | GGACTTAATC | 6300 |
| TGGGCGTTGT | TAAGCTT | | | | | 6317 |

( 2 ) INFORMATION FOR SEQ ID NO:22:

( i ) SEQUENCE CHARACTERISTICS:
  ( A ) LENGTH: 6914 base pairs
  ( B ) TYPE: nucleic acid
  ( C ) STRANDEDNESS: double
  ( D ) TOPOLOGY: linear ( i i ) MOLECULE TYPE: Genomic DNA ( v i ) ORIGINAL SOURCE:
  ( A ) ORGANISM: Enterobacter cloacae
  ( B ) STRAIN: Clinical Isolate ET- 49

( x i ) SEQUENCE DESCRIPTION: SEQ ID NO:22:

| | | | | | | |
|---|---|---|---|---|---|---|
| AAGCTTTTCG | AGTTCGCCAT | CCGGCAACAG | CTCACTGAGC | TTTTACGCGC | CCAGGGTGCC | 60 |
| TTTGAACTCA | ATTCCCAGCT | CAGTAAGGCG | GTCCTGAATA | ATCTCTTTGC | GAGATTTTTC | 120 |
| ACTGGTACCG | GCATCAGGTG | TTGCAGGTTT | CAGCTCGCCA | CCAGCCTCGC | CCTTCATCAG | 180 |
| CCGGACGTTA | GACTTCAGCG | CCGGGTGAAG | ATCTTTCAAC | TCCACCACGT | CGCCAACCTT | 240 |
| TACGCCGAAC | CATGGGCGCA | CAACTTCGTA | TTTAGCCATG | CTGTTTCCTT | ACGCCAGGTT | 300 |
| AGCGCCGTAG | ACAACGCCAG | ACAGGCCTGA | TCGTCTGCAG | TAATTTGCAG | GCCTTCAGCA | 360 |
| GACATGATCT | GGAAGTTGTA | GTTAACGTTA | GGCAGTGGGC | GCGGCAGTGG | CACAACGCCA | 420 |
| ACAGCCATAC | CCACCAGTGG | GGAGATCACG | TCACGACGAC | GAACGTACGC | GATAAACTCG | 480 |
| TTACCGGTCA | GCGCGAAGTC | ATGCGGATTT | CTTTCACCGG | TGCGAATGGC | AGAACAGCCT | 540 |
| GCAGGAGAGT | GCCGCTCACC | ACACCATTAA | CTACGTATGG | CTGAGCCATA | TTTGCCCAGA | 600 |
| TCTCAGGGGA | AACCCACATC | ACATCATACT | GAGCTACTTT | GTTGGTGCGT | GCGGTGGTAC | 660 |
| CGAATGCTCC | TTTACCAAAG | AACTCAAAAT | ATTGAGTCGT | GGTTGCGCTG | GTCAGGTCGA | 720 |
| TGTTCGCACC | ACCAGCACCA | GAACCGAGGT | TAATCTTCTT | GGTGTTGCGG | TGGTTCTTGA | 780 |
| TGCCCTGCGC | CGGGTAGGAC | TGAACCTGAA | TTTTTGAATC | GCCGTTCAGG | TAGTAGTTGA | 840 |
| CGCGCTTCTG | GTTGAACTTG | CGCATCTTCG | CCATCTGCGA | ATCCAGAACC | AGATCAATGC | 900 |
| CTACAGAGTT | AAGGCCAGCA | GCATGACGCC | AGTTAACACC | GTAGCCAGCA | GTGAACACCG | 960 |
| GAATCGGGTC | GCCATCGCTC | GCGTAGTCAG | TGTGGTCGAA | GGAGAATGGC | GCCTGACCAT | 1020 |
| CGATGCTTAC | TGACACGTCG | TCAGCGATGT | CGCCGACCAC | GTTATACAGC | TTGGCGGTTT | 1080 |

| | | | | | | |
|---|---|---|---|---|---|---|
| TACCAACCGG | CAGCACGGTC | TGAACGCCGA | TCAGGTCGTT | TACGATTTCC | ATGCCAACTT | 1140 |
| CCTGATCCCG | CAGCTGCAGC | ACCTGGTTGT | CAATCTCAGC | CCAGAAGTCA | CGGGAGAAAC | 1200 |
| CGCCAACAGC | GTTACAAGCC | AGCATGTCAG | GCGTCATCAT | TGCGCGGTTA | GCTGCAATGA | 1260 |
| TGGAATCGTT | CTGTAGGTTC | CACATGTTGC | GGTTTGCCCA | CAGCTCACTC | CAGTGCCCGC | 1320 |
| CGAGGCGGGA | GTTAGTCGCC | AGCGTCTCTT | TAGAGAAGTA | CATATGTGTT | TGTCCTTTTG | 1380 |
| TTACGCGCCA | GCTGCGGCGA | CAGTGCCAAC | GCGCATACGC | ACGCGAATGA | AGTCAGTGGT | 1440 |
| GCTGGCCGCG | ATGGTGTATT | CATCCTGGCT | GTAGCCGATC | ACTGAATCAG | TGTCGGATGT | 1500 |
| GGCAAGGGTA | AACTGACCGG | CAGTTCCCAG | CTTGATCGGG | CTGTCTTTTT | TATACGCACC | 1560 |
| AGGCAGGCAG | CGCAGCGCCA | GCTCACGACC | TTCTTCGACG | TAGTTACCTA | CTGCCGAATC | 1620 |
| CCCGGCAGGG | ATTTCTTCGG | TGATTGTCAG | GCCCTGGTGA | TAACCGACAT | CGATGATGTA | 1680 |
| CAGGCGGCCG | GTTAGCGCGG | TGGCCTGAGC | GAATTTATCG | GATGAGTTGA | TGGTTGCGGC | 1740 |
| GGTGCCAGGA | AGCAACCCGG | CGGCCGTTGT | GCGGGTTTCG | GTCTTGTACA | GAGACTGACC | 1800 |
| GTCGATATTA | ACGCGACGAT | AACGTGGCAT | TATTCCGGCT | CCTTACTTGA | AGTGTTCGTC | 1860 |
| TGCGGCTGGT | GCGCCGGTTT | CTTTGTGCTG | CTGAGCATTG | TTGGTGCCCA | GCGACTTGAA | 1920 |
| CATCGCGTCC | AGAGCTTCGC | CTGACAGAGC | GTTCGCGAGC | GATATCGCCA | TGGACCTTCG | 1980 |
| CAACCGCTTC | GCGCTTTGCT | TTCTCTTCGG | CACGGGAGTT | CGCGGTAAGG | GTTTCCGCGA | 2040 |
| GTTGCTTCTG | ATTGGCCTGC | AGCGCATCAA | CCTTTTCCGC | GAGAGGCTTA | ATAGCCGCTT | 2100 |
| CAGTATTGGT | CGCAACAGCC | TGGCCGATCA | TGCTGCCGAT | TTGTTCCAGT | TCTTCTTTGG | 2160 |
| TTAAAGGCAT | GTCGCCTCCG | TTTTGTGGTT | TGGTGCAGGC | TGTTCCTGCG | GTGTGAATAG | 2220 |
| AGCTTTGAAT | TGTTAGCGAC | GACTGCCACC | CACGACTCCT | GGCGCGCTAC | TGCGGTTCCG | 2280 |
| GTATCGTCGA | TTGTGATCTT | CCCGCCATCA | GCGAATACCG | TAAACCTGAG | CATCACCGCC | 2340 |
| ATTTCGCACG | ATGACCACCT | GCGAGTCAGT | GAGTCAGCAA | CCCAGGCATA | TTCATCCGTG | 2400 |
| CCCGGCGCAA | ACTTGGCTTT | GGCTGCCCGA | TCGAGACGCT | GCTCGCGCTC | CCGGTAGGAT | 2460 |
| TCACCCACCA | GCGCGCCGGA | GTTCGCTTTA | AGCGGCTGCG | CCAGATCGGC | GTTTACCATC | 2520 |
| AGGCCAACGC | CCTGCTCAGG | GGTGGCGGCT | CCGACTTCGT | GCAGTAGGAT | CGCGTCGTGG | 2580 |
| TCCATGCTGT | GAATCTTCGC | CACCCACTCG | GCACCCGTAG | CTCTCTGTTG | TTCGTTAGGC | 2640 |
| TCAAGCTGGT | CGAGGAAAGC | GGCGACACTG | GTATGAATCG | GCGGAACGTC | ATCGCCGCGC | 2700 |
| TCGATGGCTG | CGACGCGCTC | AAGTAGTTCT | CGGCCACCTT | CAGACTCACC | GGCGCGGGCA | 2760 |
| ACATCAACCC | ACTTTTCGAG | GTAGATACGA | TTACCGGACT | TCTTAACGTT | GCGGTTCCAC | 2820 |
| GCGCCGATAT | GGCCTGCGTT | AATCCCCTCC | GGGGAGAAAG | CAGACACGAA | CTGACCATTA | 2880 |
| ACCTGAGGGT | GGCCCAGCGG | CGCCAGGGTA | CCTTCCAGCC | CCTTATAGTG | GGCGTCGATT | 2940 |
| TGCTCTTGCG | TGTACAAGCC | GCCATTCATG | ACGACGTTAG | CTGGAAGTGT | GTAGCTCGGC | 3000 |
| AGCACCAGGT | GCTCACGCCC | GTTGTATGTT | TCGCGCCGGA | TAGACTGGCT | GTTCACCTTT | 3060 |
| GTGGTGATGT | TGACCTGAAT | ATGCTCACCA | TGTTTCGGTG | CCTGGATTGG | ACGCTGTGCT | 3120 |
| TCGTGGTTTA | CCTGGAATTT | CATGAGTTAT | TTCTCCGCCC | AGGCGTAACC | GCTCGCCTGC | 3180 |
| ATCGATTTAT | ATTCCTGTTT | GAGTTTCGTG | ATGGTGTCCG | GGTATTCCGG | CTTGCCGTCC | 3240 |
| GCATCCACCA | GCACCGACTG | CTGGCTGCAT | TTGCAGTTGA | TGGAGTTGCC | ATCTTTGCTG | 3300 |
| TACCAGTCAC | GCACCTCTTC | GTTGGTGTAG | AGGTGGGCAT | GGGCGCACTG | CGTGGGTATG | 3360 |
| TCGCGTTGTC | GGCGACAGAG | CTGAGATGTG | AACCAGCAGC | GTTTAAGGC | CGAACAGGTC | 3420 |
| ATTCGCCTCT | TGGTCTTCAT | CCCACTTGGC | CCGGCGCAGC | GCGGTAGTCA | CTTCAGTGCG | 3480 |

```
TGCTATCCGG   TTAGCCCGGC   GTTTCTCGAT   GCCGGTCTGG   TCTGTCAGGT   TGCGGGCAAT   3540
GTCCAGAGGA   TTGAGCCCGC   GCCCAACACC   ATCAGTAAGA   CACGCGCCAT   GTCGCGCTTA   3600
ACGTCAGCCG   TCAGCCCCTT   CATTTCCTCA   AATACACGCG   CATGCACCAG   CGCCATGCGT   3660
TTCTGATACT   GGTCGCTTGC   GAGGATGGAG   GCCAGCGACT   CACGCCCGGC   TGCGTACACC   3720
GGGGATTGCT   GACTGAGGTT   GTAGAACGAC   TGCCCGGTCC   CTTTTTCCGA   AGCCAGATCG   3780
ATGTACTCGT   AAAACCACAG   GTCGTAATCG   CCACCTTCAA   GCAGTACCTG   ATCAACCAGG   3840
TAACTGGCAT   CGTTCAGGAT   GATGGAGAGT   AGCATTGGGT   TTAGCTGGTA   TTCGTATCTG   3900
GCGTTTACTG   CGAGGGAGGA   AGGTATTTTG   TTGAGTGCTG   ATTTGTACGC   CTTGCCAATC   3960
TTATTCATCC   GCCTGGCGAA   GTCTTTCATT   GCCCGGCGTT   CCAGCGCATC   GGCTCCGGTC   4020
GGATCCTGAT   AGTTACGCGG   CAGAATCGGT   GGCTTCGTCT   TCTTCGTCGC   CATCCTCTTC   4080
TCCTAATGGA   AATTCATCGA   CGTTTTCATA   ACCGGCAGCA   GTGCGGAATT   TCTTCACGAC   4140
TAAAGGCTGG   TTTTTCTCCG   CTCCCTGGA    ACGTCTGGTT   AATCTCTGCC   ATGGTTTTGG   4200
CATTTGCGAG   TTTCTCAGTT   CCAGTCTGTT   CGTTGAGGTC   ATCCAGATA    ACCGTCTTCT   4260
CGCTGACTGC   ATCAATAATT   TTCAGGTCGA   TGAGCTTGTC   ACTGAAGTCT   TCAATTTCGA   4320
ATGACAGGTC   ACCGCGCCGT   GACTGGCAGC   GCGCGTTGAA   ATATTTCTGA   TCCTCGGTGC   4380
TTGCCCTTTC   ACCCGTCTGC   ATCCCAACCA   GAACCTTCAC   AGGGATATCA   ACAGATGCAG   4440
CGAAGGTTTG   CAGGTTGACG   TTATAGGTCG   CTGACGGATC   CGCTACAGCT   GTGACCAGTG   4500
GTGTGACTGT   AGCCCCTTGG   GTTGTCATCA   GAACATCGTT   ACCACGGTTC   ATTTCCCCGG   4560
CAACTTCGTT   AAACTTATCC   TGCAACTCGT   CCATGTCACG   CCATAAAGTG   ACGCGAGATT   4620
GTTGAAATCG   ATTTCCTTCT   CAAAGTTGAC   ATTAAGCTGC   CGCGCGGCGT   TCTTTAGGAA   4680
TGACTCACCA   GAACCACCCT   CGACCTTCTC   AAGGCTGACG   CAGGCGTTAT   AGCCAGGCTC   4740
AAGGAAGCCA   ATAGCATCAT   TAGAATAGTC   ACCAAGGATA   AAGACGCGAT   CGGGATGTAC   4800
GAAGCGCTGA   TTAGTTCCAC   CGCTTGGAAG   GCTCTCAACA   TATTTCCACT   GCTTTGGCTG   4860
CCCGTAGCCT   GCCGATTTCT   GGTCAGTTAC   CCACTCGCTG   ACTGTTAATG   ACCCAGCCCA   4920
TGCGATCGTA   ACCTTTTTTA   GTGACTTGCC   ACGAACAACA   GGCTGATCCC   ATGTTCTGGA   4980
ATCATTGATA   TGCAGCAGGA   TACCCGCATA   ACGTCCGACC   TGTCGGCGGC   GGTCTGCTTC   5040
AGCAAAAGCC   CGCCAAAGGC   GCTTTGTGAA   AACCTTTTTG   GTGTTCTTCT   CCCAGGCAGT   5100
TTCATCCTTA   CTCTCGTCGG   CATCATCACC   CTCGATGATT   TCCGGGTTGG   TCTGCCAGCA   5160
CTTGCCCACC   AGCTTCTCTA   CTGCGCCGTG   GGCTATTCCA   CCGCGACGAT   ACAGTGCGTA   5220
GAGGTTTTCG   TAAGTGACCT   GCTCAGGGAA   TCCATACTCG   CACCATGCGG   AATGGCGCTT   5280
ATTGTCCAGC   CCCATTGTAG   GCGCCAACAG   CCCCATACGG   GCACGGGCCA   TCCGCGCATC   5340
GTTCAACGCA   TGGTTGACGG   CGAGAGTTAA   TTTGTCAGTC   ATGGTTTGTC   CGTTGGTGGA   5400
TTTAAGGCAT   AAAAAAAGGC   CGCTTTGGCG   ACCTTGTGGC   TATTTAAAAA   GCTAAACTCT   5460
GTTGAACGAA   ATAAACATAA   TCTGCTCAGG   CTTAACGCCA   TAATCACTTG   CCAACTTCTG   5520
AGTGCACTCA   ATTAAGACAG   TTGATGCAGA   TTTCGAAGAG   CTTGCACCAT   AAATTTCGAA   5580
GTTTTCAAAT   ACTCCGCCGT   TGGTGTGGTA   AATCTTATAT   GACATAAACC   AATCATTCAT   5640
AATATCTACT   CCCTTACAGA   ATTGAGTAGA   TATTATCGGC   AAGTGCATAT   GTTTCTTTAA   5700
ATTATCTCAA   CCTTTTCGGG   ATCATCATCC   CGGCCATCTG   GCCCTTACGT   TTAATGTGTC   5760
CGTCGAGGCT   GTAGCGAATA   CCGTCCCAGC   AGTGTTCGTA   ACCGTCTGCC   AGTTAGGCA   5820
ATACCTCGCC   GGTGATGCGG   TCCGTTTTGT   AGGACCACAT   GCGGGCCTCT   CTCGCCACAT   5880
```

| | | | | | | |
|---|---|---|---|---|---|---|
| TCTTGCAGCG | AGGATGGATA | ATGATTTCGT | CAAAGCCGCG | AAGATGCGCG | ATACCGTCCT | 5940 |
| CAACACTCCC | CTGCCATTTC | TCGGCAGCCG | AGATGTTGAA | GCCCTGGCGC | TTGAGATAGC | 6000 |
| TGATAGTCTC | GGGTCGGGCG | GAGTCGGCCT | TGATGGGCCA | GTCACGCGAT | CCGGGGATTG | 6060 |
| TGTCGTATAG | CTCTGGCATA | TGGTCGAGCT | CTGTCTGCTG | ACCGTATGCC | TCGTATTCGA | 6120 |
| TGTACAGCCG | GTTGTGCAGG | ATGAACGAGC | GCACCAGCGT | GTTAGGGTCT | TTGGCGAAAC | 6180 |
| CGAAGTCAGC | ACCGAAGAAA | AGGCGATCGG | CCTCTTTCCA | TAGCTGGTCC | GAGAACTCAG | 6240 |
| CGATCCGGTA | TTTACCGGCC | AGCACCTGCT | TATCAGAGTT | TTCGAGGTAA | GCACCTTCCC | 6300 |
| AAACCCACGC | GTATGTTGCC | GGGTCAAGGC | GGCGCTGATC | GTTCTGTCGC | TCACCTTCCA | 6360 |
| GCACGTCGGG | GAACCATGGA | TTATCCGTGT | AGTTCATCTC | AACGTGATAC | AGTCGTCGCC | 6420 |
| AGCCTCTTTA | CGGAAACGCT | TATCCGTGCG | CTGCCGTCGC | GCTCCGGGTT | CCATGTCACC | 6480 |
| CAAATCTCTG | AACCTTCCTC | ACGAACGGTC | GGGCTCAGCT | TCTGCCAGGC | TATTTCGCTG | 6540 |
| ACTGATTCAG | CCTCATCAAC | CCAACAGAGC | AAGATGCGCG | CTTTCGACTT | GATGCTGTCG | 6600 |
| AGGTTATGCC | GCAGACCGCA | GAACACGTAG | TTAACGCTCT | TGTCGATGGT | GCGGATGTAC | 6660 |
| TTCTCGCCGA | TATCAAAGTT | GGAAGCCAGC | CAGGGAACAG | ACAGGATAGC | CTGTTTCACC | 6720 |
| TCCTGCATAC | TCGACTCTTC | CAGTGAGTTC | ATGAATTCAC | GCGCACAGAG | CACCACGCCG | 6780 |
| CTTTCACCGT | TCATCATCGA | CTGATACGCC | TTTACGGCTG | TCATCAGCGC | AAAAGTGCGC | 6840 |
| GTCTTGGCAC | TACCACGCCC | ACCATGCGAG | CACCGGTAAC | GCTTATTCTC | GGCGATGAAC | 6900 |
| AGTGGCGCAA | GCTT | | | | | 6914 |

( 2 ) INFORMATION FOR SEQ ID NO:23:

( i ) SEQUENCE CHARACTERISTICS:
        ( A ) LENGTH: 5975 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Klebsiella pneumoniae
        ( B ) STRAIN: Clinical Isolate KI- 50

( x i ) SEQUENCE DESCRIPTION: SEQ ID NO:23:

| | | | | | | |
|---|---|---|---|---|---|---|
| AAGCTTATTC | CACGCTGGAG | GCGTCCGGGA | TTATCGGCGT | CAACGCTATC | GCCGGCATCG | 60 |
| CCGGGACCAT | CATCGCCGGC | ATGCTCTCCG | ACCGCTTTTT | CAAACGCAAC | CGCAGCGTGA | 120 |
| TGGCCGGATT | CATCAGCCTG | CTGAACACCG | CCGGCTTCGC | CCTGATGCTC | TGGTCGCCGC | 180 |
| ACAATTACTA | CACTGATATT | CTGGCGATGA | TTATCTTCGG | GGCCACCATT | GGCGCTCTGA | 240 |
| CCTGCTTCCT | TGGCGGGCTG | ATCGCCGTCG | ATATCTCTTC | GCGCAAGGCC | GCCGGGGCCG | 300 |
| CGCTCGGCAC | CATCGGCATC | GCAGCTACGC | CGGCGCCGGC | CTGGGCGAGT | TTCTCACCGG | 360 |
| GTTCATTATT | GATAAAACGG | CTATCCTTGA | AAACGGCAAA | ACGCTGTATG | ATTTCAGCAC | 420 |
| GTTGGCGCTG | TTCTGGGTGG | GTACGGTCTG | GGTTCNGCGC | TACTCTGTTT | TACCACTGCC | 480 |
| GCCATCGTCG | CCCGGCGCCA | TGCCGTCGAA | CGGCAGACCT | CGTTCTCCTC | ATAACCGATT | 540 |
| AACGAATAAG | GAAGAAGATA | TGATGCCTGC | AAGACATCAG | GGGCTGTTAC | GCCTGTTTAT | 600 |
| CGCCTGCGCG | CTGCCGCTGC | TGGCGCTGCA | ATCTGCCGCC | GCCGCGGACT | GGCAGCTGGA | 660 |
| GAAAGTGGTC | GAGCTCAGCC | GCCACGGTAT | TCGTCCGCCG | ACGGCCGGCA | ACCGGGAAGC | 720 |
| CATCGAGGCC | GCCACCGGCC | GACCGTGGAC | CGAGTGGACC | ACCCATGACG | GGGAGCTCAC | 780 |

| | | | | | |
|---|---|---|---|---|---|
| CGGCCATGGC | TATGCCGCCG | TGGTCAACAA | AGGGCGTGCG | GAAGGCCAGC | ATTACCGCCA | 840 |
| GCTCGGCCTG | CTGCAGGCCG | GATGCCCGAC | GGCGGAGTCG | ATATACGTGC | GCGCCAGCCC | 900 |
| GCTGCAGCGG | ACGCGAGCGA | CCGCCCAGGC | GCTGGTGGAT | GGCGCCTTCC | CCGGCTGCGG | 960 |
| CGTCGCTATC | CATTATGTCA | GCGGGGATGC | CGATCCCCTG | TTTCAGACCG | ACAAGTTCGC | 1020 |
| CGCCACGCAA | ACCGACCCCG | CCCGCCAGCT | GGCGCGGTGA | AAGAGAAGGC | CGGGGATCTG | 1080 |
| GCGCAGGTCG | GCAGGCGCTG | GCGCCGACCA | TCCAGCTATT | GAAACAGGCG | GTTTGTCAGG | 1140 |
| CCGATAAGCC | CTGCCCGATC | TTCGATACCC | CGTGGCAGGT | CGAGCAGAGC | AAAAGTGGGA | 1200 |
| AGACCACCAT | TAGCGGACTG | AGCGTGATGG | CCAATATGGT | GGAGACGCTG | CGTCTCGGCT | 1260 |
| GGAGTGAAAA | CCTGCCTCTC | AGCCAGCTGG | CGTGGGGCAA | GATCACCCAG | GCCAGGCAGA | 1320 |
| TCACCGCCCT | GCTGCCGCTG | TTAACGGAAA | ACTACGATCT | GAGTAACGAT | GTGTTGTATA | 1380 |
| CCGCGCAAAA | ACGCGGGTCG | GTGCTGCTCA | ACGCTATGCT | CGACGGCGTC | AAACCGGAGC | 1440 |
| GAATCGAACG | TACGCTGGCT | GCTGCTGGTG | GCCATGACAC | CAATATCGCC | ATGGTGCGCA | 1500 |
| CGCTGATGAA | CTTTAGCTGG | CAGCTGCCGG | GCTACAGCCG | GGGAAATATC | CGCCGGGCA | 1560 |
| GCAGCCTGGT | GCTGGAGCGC | TGGCGCAACG | CGAAGAGCGG | AGAACGCTAT | CTGCGGGTCT | 1620 |
| ATTTCCAGGC | CCAGGGCCTC | GACGACCTGC | GTCGTCTGCA | GACGCCGGAC | GCGCAGACCC | 1680 |
| CGATGCTGCG | TCAGGAGTGG | CATCAGCCGG | GCTGCCGTCA | GACCGATGTC | GGTACGCTGT | 1740 |
| GTCCCTTCCA | GGCGGCTATT | ACCGCCCTCG | GTCAGCGTAT | CGACCGATCA | TCCGCCCCGG | 1800 |
| CGGTAGCATG | GTCCTGCCGT | AGCGGCGCGG | TGTTTGTCCG | GGCCCGGGAA | AACCTTTTTT | 1860 |
| TCCAGGCCGG | CACGACGTCC | GTTATCCGTT | GTCCGGCGCA | AACGCCCCGG | CGGCGACCTG | 1920 |
| CGCCGGGGTG | ACACCCGCTG | TCCAGCACCC | AGCCGCTTAT | CAGCCCAGCA | GGCGTGACGT | 1980 |
| CGAACGCCGG | ATTGTAAACG | GTGGCCCCCG | TCGGCGCCCA | CTGTACCGCG | CCGAAGCTGC | 2040 |
| CCGCCACTCC | GGTCACTTCC | GCCGCCGCGC | GCTGCTCAAT | GGGGATCGCC | GCCCGTTCG | 2100 |
| GGCAATGGCG | GTCGAGGGTG | GTCTGCGGGG | CAGCGACGTA | AAACGGGATC | TGGTGATAAT | 2160 |
| GGGCCAAAAC | CGCCAGAGAA | TAGGTGCCGA | TTTTATTCGC | CACGTCGCCG | TTGGCGGCGA | 2220 |
| TACGGTCGGC | GCCGACCCAC | ACCGCATCCA | CCTGCCCCTG | CGCCATCAGG | CTGGCGGCCA | 2280 |
| TTGAATCGGC | GATCAGCTGA | TAGGGCACGC | CCAGCTCGCC | CAGCTCCCAG | GCGGTTAAAC | 2340 |
| GACCGCCCTG | CAGCAGCGGC | CGGGTTTCAT | CAACCCATAC | GTTGGTCACT | TTTCCCTGCC | 2400 |
| GGTGCGCCAG | CGCGATAACG | CCGAGGGCGG | TCCCTACCCC | GGCGGTCGCC | AGGCCACCGG | 2460 |
| TGTTGCAGTG | GGTCAGCAGT | CGACTGCCGG | GCTTCACCAG | CGCACTGCCC | GCCTCAGCGA | 2520 |
| TGCGGTCGCA | CAGCTGTTTA | TCTTCTTCGA | CCAGACGCAA | GGCTTCCGCT | TCCAGCGCCT | 2580 |
| GCGGGTAATC | TCCGGGCCAG | CGCTGCTTCA | TGCGATCAGA | TTATTCATCA | GGTTGACCGC | 2640 |
| CGTCGGCCGC | GCCGCGCGCA | GTCTCCAGCG | CCTGCTGGAG | TGCATCCCGG | TTCAGGCCGC | 2700 |
| GCTGGGCCAG | CAGGGCCAGC | AGCAGGCTGG | CGGACAGGCC | AATCAGCGGC | GCGCCGCGCA | 2760 |
| CCCCGCAGGT | ATGAATATGG | TCCACCAGCA | GCGCAACGTT | ATCCGCCGCC | AGCCAGCGTT | 2820 |
| TTTCCTGCGG | CAAGGCCTGC | TGGTCGAGAA | TAAAAGCTG | ATTTTCACTC | ACCCGCAGGC | 2880 |
| TGGTGGTCTG | TAATGTCTGC | ATGTCGTTAA | ATCCCTGTTG | CGTTGTTGTA | TCACATTGTG | 2940 |
| TCAGGATGGA | ATCCAGAAGT | ATAGACGTCT | GAACGGCTTA | ATCAGAATTC | GAGGATCGAG | 3000 |
| GCAATGTCGC | AATACCATAC | CTTCACCGCC | CACGATGCCG | TGGCTTACGC | GCAGAGTTTC | 3060 |
| GCCGGCATCG | ACANCCATCT | GAGCTGGTCA | GCGCGCAGGA | AGTGGGCGAT | GGCAACTCAA | 3120 |
| TCTGGTGTTT | AAAGTGTTCG | ATCGCCAGGG | CGTCACGGGC | GATCGTCAAA | CAGGCTCTGC | 3180 |

-continued

```
CCTACGTGCG CTGCGTCGGC GAATCCTGGC CGCTGACCCT CGACCGCGCC CGTCTCGAAG   3240
CGCAGACCCT GGTCGCCCAC TATCAGCACA GCCCGCAGCA CACGGTAAAA ATCCATCACT   3300
TTGATCCCGA GCTGGCGGTG ATGGTGATGG AAGATCTTTC CGACCACCGC ATCTTGCGCG   3360
GAGAGCTTAT CGCTAACGTC TACTATCCCC AGGCGGCCCG CCAGCTTGGC GACTATCTGG   3420
CGCAGGTGCT GTTTCACACC AGCGATTTCT ACCTCCATCC CCACGAGAAA AAGGCGCAGG   3480
TGGCGCAGTT TATTAACCCG GCGATGTGCG AGATCACCGA GGATCTGTTC TTTAACGACC   3540
CGTATCAGAT CCACGAGCGC AATAACTACC CGGCGGAGCT GGGAGGCCGA TGTCGCCGCC   3600
CTGCGCGACG ACGCTCAGCT TAAGCTGGCG GTGGCGGCGC TGAAGCACCG TTTCTTTGCC   3660
CATGCGGAAG CGCTGCTGCA CGGCGATATC CACAGCGGGT CGATCTTCGT TGCCGAAGGC   3720
AGCCTGAAGG CCATCGACGC CGAGTTCGGC TACTTCGGCC CCATTGGCTT CGATATCGGC   3780
ACCGCCATCG GCAACCTGCT GCTTAACTAC TGCGGCCTGC CGGGCCAGCT CGGCATTCGC   3840
GATGCCGCCG CCGCGCGCGA GCAGCGGCTG AACGACATCC ACCAGCTGTG GACCACCTTT   3900
GCCGAGCGCT TCCAGGCGCT GGCGGCGGAG AAAACCCGCG ACGCGGCGCT GGCTTACCCC   3960
GGCTATGCCT CCGCCTTTCT GAAAAAGGTG TGGGCGGACG CGGTCGGCTT CTGCGGCAGC   4020
GAACTGATCC GCCGCAGCGT CGGACTGTCG CACGTCGCGG ATATCGACAC TATCCAGGAC   4080
GACGCCATGC GTCATGAGTG CCTGCGCCAC GCCATTACCC TGGGCAGAGC GCTGATCGTG   4140
CTGGCCGAGC GTATCGACAG CGTCGACGAG CTGCTGGCGN GGGTACGCCA GTACAGCTGA   4200
GTGCGCCTGT TTCCCTCACC CCAACCCTCT CCCACAGGGA GAGGGAGCAC CCCCTAAAAA   4260
AGTGCCATTT TCTGGGATTG CCCGGCGNGN TGCGCTTGCC GGGCCTACAG ATAGCCGCAT   4320
AACGGTTTGA TCTTGCACTC TTTCGTAGGC CGGGTAAGGC GAAAGCCGCC ACCCGGCAGA   4380
CATGCGAGTA CAATTTTGCA TTTACCTTAC CCTCACCCCA GATACTCAAT CACCGATAGC   4440
CCGCCGTTGT AATCGGTGCT GTAGATAATG CCTTGCGCAT CGACAAACAC GTCACAGGAC   4500
TGGATCACCC GCGGGCGGCC GGGACGGGTA TCCATCATTC TCTCAGCGCA GCCGGCACCA   4560
GCGCCCCGGT CTCCAGCGGG CGATACGGGT TGGAAATGTC GTAAGCCCGC ACGCCGGCAT   4620
TCTGATACGT GGCAAAAATC AGCGTTGAGC TGACAAAGCT CCCCGGCCGG TTCTCATGCA   4680
GGTTGTGCGG ACCGAAATGC GCCCCTTTCG CCACGTAATC CGCTTCATCC GGCGGCGGGA   4740
AGGTGGCGAT GCTCACCGGG TTGGTTGGCT CGCGGATATC AAACAGCCAG ATCAGCTTCT   4800
CGCCGTCCTC CTGGTTATCG AGCACCGCTT CATCCAGCAC CACCAGCAGA TCGCGATCCG   4860
GCAGCGGCAG CGCGGTATGC GTTCCGCCGC CGAACGGCGG GCTCCAGTTG CGATGGCTAA   4920
TCAGCCTCGG CTGGGTACGG TCTTTGACAT CCAGCAGCGT CAGGCCGCCG TCGCGCCAGC   4980
TGCGTAGGCG TATCCCCGGC AATAATGGCG TGATGCAGCG CATAGCGTTT GCCCTGCGGC   5040
CAGTCCGGTG TTTCACCGCC CGCCTGGTGC ATCCCCGGCA GCCACCAGCG CCCGGCTACT   5100
TCGGGCTTAC GCGGATCGGC CAGATCGATG GTCAGGAAGA TGTAGTCGGT AAAACCGTCG   5160
ATCAGCGCAG ACACATACGC CCAGCGCCCG CCGACGTACC AGATGCGGTG AATACCGATG   5220
CCGTTAAGCG ACAGGAAACT GATTTCCGCG CTGCGCGGG AGTGGAAATA TCAAAGATGC   5280
GCAGCCCGGC GCTCCAGCCC CTGTCCTGCA CATCGCTGAC CGTGTCACCC ACCGAGCGGG   5340
TGTAGTACAC CTTCTCATCA GCAAACGGG CGTCAGCAAA CAGATCCCGG GCGTTGATCA   5400
CCAGCAGCAG ATCGTCATGC GCCTGGAGTG CACGTTCCAG GTGCCCGGCG GCGCGGCAAT   5460
ATAGTTGACG GTGGTGGGCC GGGTCGGATC GCGAACATCG ACCACGGAAA AACCCTGCGA   5520
CACCATATGG CCGATATAGG CGAATCCGCG GTGCACCATC AGCTGCACGC CGTCCGGACG   5580
```

-continued

| | | | | | | |
|---|---|---|---|---|---|---|
|ACCGCCCTGA|TCGCTATGGC|CAATCAGCCG|CATATTGCGG|CTGTATTCGG|GGGAAGGTAA|5640|
|TGCTGACATA|GGGGATCCCT|CTCGCCCGGT|GGCATGGTTT|TCCCCCCTCT|CCTGCGGAGA|5700|
|GGGCCGGGGC|GAGGGCACCA|GGCCGCCGCC|CACCGCCACC|CGGCTTGATT|TTATTTGTTC|5760|
|TTCGCTTCCA|GCGTCGCGAA|CCACGGCGCG|ATAAAGTCTT|CGGTCTGGCC|CCAGCCAGGG|5820|
|ATAATTTTCC|CCAGCGACGC|CACGTTTACC|GCTCCCGGCT|GGGCCGCCAG|CAGCGCCTGG|5880|
|GGAATCGCTG|CCGCCTTGAA|GTCGTAGGTG|GCTGGCGTCG|GCTCGCCGGC|GATCTTGTTG|5940|
|GCGATCAGCC|GCACGTTGGT|CGCGCCGATA|AGCTT| | |5975|

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:24:

CGACGTTGTA AAACGACGGC CAGT    24

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:25:

CAGGAAACAG CTATGAC    17